US010905777B2

(12) United States Patent
Debs et al.

(10) Patent No.: US 10,905,777 B2
(45) **Date of Patent: *Feb. 2, 2021**

(54) SYSTEMS AND METHODS FOR NUCLEIC ACID EXPRESSION IN VIVO

(71) Applicant: DNARx, San Francisco, CA (US)

(72) Inventors: Robert James Debs, San Francisco, CA (US); Timothy D. Heath, Madison, WI (US); Chakkrapong Handumrongkul, Richmond, VA (US)

(73) Assignee: DNARx, San Francisco, CA (US)

(*) Notice: Subject to any disclaimer, the term of this patent is extended or adjusted under 35 U.S.C. 154(b) by 9 days.

This patent is subject to a terminal disclaimer.

(21) Appl. No.: 16/171,020

(22) Filed: Oct. 25, 2018

(65) Prior Publication Data

US 2019/0046661 A1 Feb. 14, 2019

Related U.S. Application Data

(60) Continuation of application No. 16/140,086, filed on Sep. 24, 2018, which is a division of application No. 15/268,000, filed on Sep. 16, 2016, now Pat. No. 10,086,089.

(60) Provisional application No. 62/220,646, filed on Sep. 18, 2015.

(51) Int. Cl.

| | |
|---|---|
| ***A61K 48/00*** | (2006.01) |
| ***A61K 9/127*** | (2006.01) |
| ***A01N 61/00*** | (2006.01) |
| ***C12N 15/85*** | (2006.01) |
| ***C07H 21/04*** | (2006.01) |
| ***A61K 39/395*** | (2006.01) |
| ***C07K 16/00*** | (2006.01) |
| ***A61K 47/69*** | (2017.01) |
| ***A61K 31/19*** | (2006.01) |
| ***A61K 31/522*** | (2006.01) |
| ***A61K 31/573*** | (2006.01) |
| ***A61K 38/19*** | (2006.01) |
| ***A61K 38/48*** | (2006.01) |
| ***C07K 16/28*** | (2006.01) |
| *A61K 31/00* | (2006.01) |
| *A61K 39/00* | (2006.01) |

(52) U.S. Cl.

CPC ........ *A61K 48/0016* (2013.01); *A61K 9/1272* (2013.01); *A61K 31/19* (2013.01); *A61K 31/522* (2013.01); *A61K 31/573* (2013.01); *A61K 38/193* (2013.01); *A61K 38/4846* (2013.01); *A61K 39/395* (2013.01); *A61K 47/6911* (2017.08); *A61K 48/0066* (2013.01); *A61K 48/0083* (2013.01); *C07K 16/00* (2013.01); *C07K 16/2887* (2013.01); *C12Y 304/21022* (2013.01); *A61K 31/00* (2013.01); *A61K 48/005* (2013.01); *A61K 2039/505* (2013.01); *A61K 2039/53* (2013.01); *C07H 21/04* (2013.01); *C07K 2317/24* (2013.01); *C12N 15/85* (2013.01)

(58) Field of Classification Search

CPC .. A61K 48/0016; A61K 31/573; A61K 9/127; C12N 15/85; C07H 21/04

USPC ................ 514/44 R, 1; 424/450; 435/320.1; 536/23.53

See application file for complete search history.

(56) References Cited

U.S. PATENT DOCUMENTS

| | | | |
|---|---|---|---|
| 6,074,667 | A | 6/2000 | Kinnuen et al. |
| 6,133,026 | A | 10/2000 | Huang et al. |
| 6,806,084 | B1 | 10/2004 | Debs et al. |
| 7,244,609 | B2 | 7/2007 | Drocourt et al. |
| 7,592,010 | B2 | 9/2009 | Rosen et al. |
| 7,592,440 | B2 | 9/2009 | Freier et al. |
| 7,919,472 | B2 | 4/2011 | Monia et al. |
| 8,236,280 | B2 | 8/2012 | Reinke |
| 9,045,754 | B2 | 6/2015 | Bhanot et al. |
| 9,132,202 | B2 | 9/2015 | Tabor |
| 10,086,089 | B2 | 10/2018 | Debs et al. |
| 2002/0108132 | A1 | 8/2002 | Rapp |
| 2004/0219677 | A1 | 11/2004 | Drocourt et al. |
| 2005/0142109 | A1 | 6/2005 | Liu et al. |
| 2006/0160184 | A1 | 7/2006 | Hoogenboom et al. |

(Continued)

FOREIGN PATENT DOCUMENTS

| | | |
|---|---|---|
| CN | 101812177 | 8/2010 |
| CN | 102366411 | 3/2012 |

(Continued)

OTHER PUBLICATIONS

Bar et al., Effect of HIV Antibody VRC01 on Viral Rebound after Treatment Interruption. N Engl J Med. Nov. 24, 2016;375(21):2037-2050.

(Continued)

*Primary Examiner* — Shin Lin Chen

(74) *Attorney, Agent, or Firm* — Casimir Jones, S.C.; Jason R. Bond

(57) ABSTRACT

The present invention provides compositions, systems, kits, and methods for generating expression of one or more proteins and/or biologically active nucleic acid molecules in a subject (e.g., at therapeutic levels for extended periods required to produce therapeutic effects). In certain embodiments, systems and kits are provided that comprise a first composition comprising a first amount of polycationic structures, and a second composition comprising a therapeutically effective amount of expression vectors (e.g., non-viral expression vectors not associated with liposomes) that are CpG-free or CpG-reduced, where the expression vectors comprise a first nucleic acid sequence encoding: i) a first therapeutic protein or proteins, and/or ii) a first biologically active nucleic acid molecule or molecules.

28 Claims, 45 Drawing Sheets

Specification includes a Sequence Listing.

(56) References Cited

U.S. PATENT DOCUMENTS

| | | | |
|---|---|---|---|
| 2007/0003521 | A1 | 1/2007 | Yew |
| 2009/0252713 | A1 | 10/2009 | Soubrier |
| 2014/0120157 | A1 | 5/2014 | Chang et al. |
| 2015/0071903 | A1 | 3/2015 | Liu et al. |
| 2015/0079155 | A1 | 3/2015 | Jensen et al. |
| 2017/0080108 | A1 | 3/2017 | Debs et al. |
| 2019/0083653 | A1 | 3/2019 | Debs et al. |

FOREIGN PATENT DOCUMENTS

| | | |
|---|---|---|
| EP | 2061514 | 11/2014 |
| JP | 2002-524473 | 8/2002 |
| WO | WO 1998/07408 | 2/1998 |
| WO | WO 1999/065465 | 12/1999 |
| WO | WO 2000/014262 | 3/2000 |
| WO | WO 2001/075092 | 10/2001 |
| WO | WO 2014/100073 | 6/2014 |
| WO | WO 2016/028682 | 2/2016 |
| WO | WO 2017/049132 | 3/2017 |
| WO | WO 2018/175932 | 9/2018 |

OTHER PUBLICATIONS

Caskey et al., Antibody 10-1074 suppresses viremia in HIV-1-infected individuals. Nat Med. Feb. 2017;23(2):185-191.

Kroon et al., Liposomal delivery of dexamethasone attenuates prostate cancer bone metastatic tumor growth in vivo. Prostate. Jun. 2015;75(8):815-24.

Scheid et al., HIV-1 antibody 3BNC117 suppresses viral rebound in humans during treatment interruption. Nature. Jul. 28, 2016;535(7613):556-60.

International Search Report and Written Opinion for PCT/US2018/024096, dated Aug. 8, 2018, 14 pages.

Argyros et al., Development of S/MAR minicircles for enhanced and persistent transgene expression in the mouse liver. J Mol Med (Berl). May 2011;89(5):515-29.

Barrett et al., Regulation of eukaryotic gene expression by the untranslated gene regions and other non-coding elements. Cell Mol Life Sci. Nov. 2012;69(21):3613-34.

Bryan et al., Implications of protein fold switching. Curr Opin Struct Biol. Apr. 2013;23(2):314-6.

De Wolf et al., Plasmid CpG depletion improves degree and duration of tumor gene expression after intravenous administration of polyplexes. Pharm Res. Jul. 2008;25(7):1654-62.

Felgner et al., Enhanced gene delivery and mechanism studies with a novel series of cationic lipid formulations. J Biol Chem. Jan. 28, 1994;269(4):2550-61.

Gill et al., Progress and prospects: the design and production of plasmid vectors. Gene Ther. Feb. 2009;16(2):165-71.

Kaur et al., Addressing the challenge: current and future directions in ovarian cancer therapy. Curr Gene Ther. Dec. 2009;9(6):434-58.

Kotterman et al., Engineering adeno-associated viruses for clinical gene therapy. Nat Rev Genet. Jul. 2014;15(7):445-51.

Lenzi et al., Oversight and Review of Clinical Gene Transfer Protocols: Assessing the Role of the Recombinant DNA Advisory Committee. Committee on the Independent Review and Assessment of the Activities of the NIH Recombinant DNA Advisory Committee; Board on Health Sciences Policy; Institute of Medicine. Washington (DC): National Academies Press (US); Mar. 2014 16 pages.

Liu et al., Cationic liposome-mediated intravenous gene delivery. J Biol Chem. Oct. 20, 1995;270(42):24864-70.

Liu et al., Factors influencing the efficiency of cationic liposome-mediated intravenous gene delivery. Nat Biotechnol. Feb. 1997;15(2):167-73.

Maqbool et al., The substrate-binding protein in bacterial ABC transporters: dissecting roles in the evolution of substrate specificity. Biochem Soc Trans. Oct. 2015;43(5):1011-7.

Sellins et al., Type I interferons potently suppress gene expression following gene delivery using liposome(—)DNA complexes. Mol Ther. Sep. 2005;12(3):451-9.

Song et al., Free liposomes enhance the transfection activity of DNA/lipid complexes in vivo by intravenous administration. Biochim Biophys Acta. Jun. 24, 1998;1372(1):141-50.

Song et al., Enhanced gene expression in mouse lung by prolonging the retention time of intravenously injected plasmid DNA. Gene Ther. Nov. 1998;5(11):1531-7.

Tan et al., Sequential injection of cationic liposome and plasmid DNA effectively transfects the lung with minimal inflammatory toxicity. Mol Ther. May 2001;3(5 Pt 1):673-82.

Tu et al., Non-replicating Epstein-Barr virus-based plasmids extend gene expression and can improve gene therapy in vivo. J Biol Chem. Sep. 29, 2000;275(39):30408-16.

Zhang et al., Mechanistic studies of sequential injection of cationic liposome and plasmid DNA. Mol Ther. Feb. 2006;13(2):429-37.

International Search Report and Written Opinion for PCT/US2016/052205, dated Dec. 15, 2016, 17 pages.

Gao et al., Potentiation of cationic liposome-mediated gene delivery by polycations. Biochemistry. Jan. 23, 1996;35(3):1027-36.

Extended European Search Report for EP16847422.9 dated Apr. 10, 2019, 11 pages.

Lee et al., Dexamethasone-loaded peptide micelles for delivery of the heme oxygenase-1 gene to ischemic brain. Control Release. Feb. 28, 2014;158(1):131-8.

Mishra et al., Dexamethasone-loaded reconstitutable charged polymeric (PLGA)n-b-bPEI micelles for enhanced nuclear delivery of gene therapeutics. Macromol Biosci. Jun. 2014;14(6):831-41.

Extended European Search Report for EP18770192.5, dated Jul. 29, 2020, 11 pages.

Bauer et al., The impact of intragenic CpG content on gene expression. Nucleic Acids Res. Jul. 2010;38(12):3891-908.

Davies et al., The use of CpG-free plasmids to mediate persistent gene expression following repeated aerosol delivery of pDNA/PEI complexes. Biomaterials. Aug. 2012;33(22):5618-27.

FIG. 2

CpG free hG-CSF nucleic acid Sequence (SEQ ID NO:1)

Atggctggacctgccacccagagccccatgaagctgatggccctgcagctgctgctgtggcacagtgcactctggac
agtgcaggaagccaccccccctgggccctgccagctccctgccccagagcttcctgctcaagtgcttagagcaagtga
ggaagatccaggggggatggggcagctctccaggagaagctgtgtgccacctacaagctgtgccaccctgaggagctg
gtgctgctgggacactctctgggcatcccctgggctcccctgagcagctgccccagccaggccctgcagctggcagg
ctgcttgagccaactccatagtggccttttcctctaccaggggctcctgcaggccctggaagggatctcccctgagt
tgggtcccaccttggacacactgcagctggatgttgctgactttgccaccaccatctggcagcagatggaagaactg
ggaatggcccctgccctgcagcccacccagggtgccatgcctgcctttgcctctgctttccagagaagggcaggagg
ggtcctggttgcctcccatctgcagagcttcctggaggtgtcctacagagttctaagacaccttgcccagccctga

CpG free hG-CSF Protein (SEQ ID NO:2)

MAGPATQSPMKLMALQLLLWHSALWTVQEATPLGPASSLPQSFLLKCLEQVRKIQGDGAALQEKLVSECATYKLCHP
EELVLLGHSLGIPWAPLSSCPSQALQLAGCLSQLHSGLFLYQGLLQALEGISPELGPTLDTLQLDVADFATTIWQQM
EELGMAPALQPTQGAMPAFASAFQRRAGGVLVASHLQSFLEVSYRVLRHLAQP

062316 # 4 | Kozak2 | mCMVEF1I126 | hFIX | pA

063016 # 5 | M1 | Kozak2 | mCMVEF1I126 | hFIX | pA | M3

FIG. 39

Bicistronic antiCD20 (SEQ ID NO:5)

8 : RINhe-ΔmCMVΔEFI126-BstEII-GAK-ΔantiCD20-H –F2(RAKR)-F2A -ΔantiCD20-L-BglII-MixpA-BV2

CACTATGTGGACATGAATTCAATTGGCTAGCAGGAGTCAATGGGAAAAACCCATTGGAGCCAAGTACACTGACTCAATAGGGACTTTCCATTGGGTTTTGCCCA
GTACATAAGGTCAATAGGGGGTGAGTCAACAGGAAAGTCCCATTGGAGCCAAGTACATTGAGTCAATAGGGACTTTCCAATGGGTTTTGCCCAGTACATAAGG
TCAATGGGAGGTAAGCCAATGGGTTTTTCCCATTACTGACATGTATACTGAGTCATTAGGGACTTTCCAATGGGTTTTGCCCAGTACATAAGGTCAATAGGGGTG
AATCAACAGGAAAGTCCCATTGGAGCCAAGTACACTGAGTCAATAGGGACTTTCCATTGGGTTTTGCCCAGTACAAAAGGTCAATAGGGGGTGAGTCAATGGG
TTTTTCCCATTATTGGCACATACATAAGGTCAATAGGGGTGACTAGTGGAGAAGAGCATGCTTGAGGGCTGAGTGCCCCTCAGTGGGCAGAGAGCACATGGCC
CACAGTCCCTGAGAAGTTGGGGGGAGGGGTGGGCAATTGAACTGGTGCCTAGAGAAGGTGGGGCTTGGGTAAACTGGGAAAGTGATGTGGTGTACTGGCTC
CACCTTTTTCCCCAGGGTGGGGGAGAACCATATATAAGTGCAGTAGTCTCTGTGAACATTCAAGCTTCTGCCTTCTCCCTCCTGTGAGTTTGgtaagtcactgactgtct
atgcctgggaaagggtgggcaggagatggggcagtgcaggaaaagtggcactatgaacccTGCAGCCCTAGAcaattgtactaaccttcttctctttcctctcctgacagGTTGGTAACCAAGCCAC
CATGGGCTGGTCCCTGATCCTGCTGTTCCTGGTGGCTGTGGCCACCAGAGTGCTGAGCCAGGTGCAGCTGCAGCAGCCTGGGGCTGAGCTTGTGAAACCTGGG
GCCTCTGTGAAGATGAGCTGCAAGGCCTCTGGCTACACCTTCACCAGCTACAACATGCACTGGGTCAAGCAGACCCCTGGCAGAGGCCTGGAATGGATTGGAG
CCATCTACCCTGGCAATGGGGACACCTCCTACAACCAGAAGTTCAAGGGCAAGGCCACCCTGACAGCTGACAAGAGCAGCAGCACAGCCTACATGCAGCTGTC
CAGCCTGACCTCTGAGGACTCTGCTGTGTACTACTGTGCCAGGTCCACCTACTATGGGGGAGACTGGTACTTCAATGTGTGGGGAGCTGGCACCACAGTGACAG
TGTCTGCTGCCAGCACCAAGGGCCCCTCTGTGTTTCCTCTGGCCCCCAGCAGCAAGAGCACCTCTGGGGGAACAGCTGCCCTGGGCTGCCTTGTGAAGGACTAC
TTCCCTGAGCCTGTGACTGTGTCCTGGAACTCTGGGGCCCTGACATCTGGGGTGCACACCTTCCCTGCAGTGCTGCAGTCCAGTGGCCTGTACTCCCTGTCCTCT
GTTGTGACAGTGCCCAGCTCCAGCCTGGGCACCCAGACCTACATCTGCAATGTGAACCACAAGCCCAGCAACACCAAGGTGGACAAGAAGGCTGAGCCCAAGA
GCTGTGACAAGACCCACACCTGTCCCCCCTGTCCTGCCCCTGAACTGCTGGGAGGACCTTCTGTGTTCCTGTTCCCACCCAAGCCCAAGGATACCCTGATGATCA
GCAGAACCCCTGAAGTGACCTGTGTGGTGGTGGATGTGTCCCATGAGGACCCAGAAGTGAAGTTCAATTGGTATGTGGATGGGGTGGAAGTGCACAATGCCA
AGACCAAGCCCAGAGAGGAACAGTACAACAGCACCTACAGAGTGGTGTCTGTGCTGACTGTGCTGCACCAGGACTGGCTGAATGGCAAAGAGTACAAGTGCA
AGGTGTCCAACAAGGCCCTGCCAGCCCCCATTGAGAAAACCATCAGCAAGGCCAAGGGCCAGCCTAGAGAACCCCAGGTGTACACACTGCCCCCTAGCAGGGA
TGAGCTGACCAAGAACCAGGTGTCCCTGACATGCCTTGTGAAAGGCTTCTACCCCTCTGACATTGCTGTGGAATGGGAGAGCAATGGACAGCCTGAGAACAACT
ACAAGACCACCCCCCCTGTGCTGGACTCTGATGGCTCATTCTTCCTGTACAGCAAGCTGACAGTGGACAAGTCCAGATGGCAGCAGGGCAATGTGTTCAGCTGC
TCTGTGATGCATGAGGCCCTGCACAACCACTACACCCAGAAAAGCCTGTCCCTGTCCCCTGGCAAGAGAGCAAAGAGGGCACCAGTGAAACAGACTTTGAATTT
TGACCTTCTCAAGTTGGCAGGAGATGTGGAGTCCAACCCTGGACCTATGGACTTCCAGGTGCAGATCATCAGCTTTCTGCTGATCTCTGCCTCTGTGATCATGAG
CAGAGGCCAGATTGTGCTGAGCCAGAGCCCTGCCATCCTGTCTGCAAGCCCTGGGGAGAAAGTGACCATGACCTGCAGAGCCAGCAGCTCTGTGTCCTACATCC
ACTGGTTCCAGCAGAAGCCTGGCAGCAGCCCCAAGCCTTGGATCTATGCCACCAGCAACCTGGCATCTGGGGTGCCAGTCAGATTCTCTGGCTCTGGATCTGGC
ACCAGCTACAGCCTGACCATCAGCAGAGTGGAAGCTGAGGATGCTGCCACCTACTACTGCCAGCAGTGGACCAGCAATCCCCCCACCTTTGGAGGGGGCACCA
AGCTGGAAATCAAGAGAACAGTGGCTGCCCCCTCTGTGTTCATCTTCCCACCCTCTGATGAGCAGCTGAAGTCTGGAACAGCCTCTGTTGTGTGCCTGCTGAACA
ACTTCTACCCCAGAGAAGCCAAGGTGCAGTGGAAGGTGGACAATGCCCTGCAGTCTGGCAACTCCCAGGAATCTGTGACAGAGCAGGACAGCAAGGACTCCAC
CTACTCCCTGAGCAGCACCCTGACCCTGAGCAAGGCTGACTATGAGAAGCACAAAGTGTATGCCTGTGAAGTGACCCACCAGGGCCTGTCCAGCCCTGTGACCA
AGAGCTTCAACAGAGGGGAGAGCTGAAGATCTACTTCTGGCTAATAAAAGATCAGAGCTCTAGTGATCTGTGTGTTGGTTTTTTGTGTCTGCATTCTAGCTCTAG
TGATCAGCAGTTCAACCTGTTGATAGTATGTACTAAGCTCTCATGTTTAATGTACTAAGCTCTCATGTTTAATGAACTAAACCCTCATGGCTAATGTACTAAGCTCT
CATGGCTAATGTACTAAGCTCTCATGTTTCATGTACTAAGCTCTCATGTTTGAACAATAAAATTAATATAAATCAGCAACTTAAATAGCCTCTAAGGTTTTAAGTTT
TATAAGAAAAAAAAGAATATATAAGGCTTTTAAAGGTTTTAAGGTTTCCTAGGTTATCCTCATATGAGCTCTTAGAAAAACTCATCCAGCATCAAATGAAACTGC
AATTTATTCATATCAGGATTATCAATACCATATTTTTGAAAAAGTCTTTTCTGTAATGAAGGAGAAAACTCACCCAGGCAGTTCCATAGGATGGCAAGATCCTGGT
ATCTGTCTGCAATTCCAACTCTTCCAACATCAATACAACCTATTAATTTCCCCTCATCAAAAATAAGGTTATCAAGTGAGAAATCACCATGAGTGACCACTGAATCT
GGTGAGAATGGCAAAAGATTATGCATTTCTTTCCAGACTTGTTCAACAGGCCAGCCATTTCTCTCATCATCAAAATCACTGGCATCAACCAAACCATTATTCATTC
TTGATTGGGCCTGAGCCAGTCTAAATACTCTATCAGAGTTAAAAGGACAATTACAAACAGGAATGGAATGCAATCTTCTCAGGAACACTGCCAGGGCATCAACA
ATATTTTCACCTGAATCAGGATATTCTTCCAATACCTGGAATGCTGTTTTCCCTGGGATGGCAGTGGTGAGTAACCATGCATCATCAGGAGTTCTGATAAAATGCT
TGATGGTTGGAAGAGGCATAAATTCAGTCAGCCAGTTTAGTCTGACCATCTCATCTGTAACATCATTGGCAACAGAACCTTTGCCATGTTTCAGAAACAACTCTG
GGCATCTGGCTTCCCATACAATCTATAGATTGTGGCACCTGATTGCCCAACATTATCTCTAGCCCATTTATACCCATATAAATCAGCATCCATGTTGGAATTTAAT
CTTGGCCTGGAGCAAGAGGTTTCTCTTTGAATATGGCTCATACATGTGCACCTCCTATAGTGAGTTGTATTATACTATGCAGATATACTATGCCAATGTTTAATTG
TCAG

FIG. 40

Dual Cassette CpG-Free Non-Optimized anti-CD20 plasmids construct (SEQ ID NO:6)

2 : DraIII-RINhe-ΔmCMVΔEF1I126-BstEII-ΔantiCD20-H-BglII-MixpA -ΔmCMVΔEF1I126-BstEII-ΔantiCD20-L-BglII-MixpA/BV2 : 5131bp CACTATGTGGACATGAATTCAATTGGCTAGCAGGAGTCAATGGGAAAAACCCATTGGAGCCAAGTACACTGACTCAATAGGGACTTTCCATTGGGTTTTGCCCA
GTACATAAGGTCAATAGGGGGTGAGTCAACAGGAAAGTCCCATTGGAGCCAAGTACATTGAGTCAATAGGGACTTTCCAATGGGTTTTGCCCAGTACATAAGG
TCAATGGGAGGTAAGCCAATGGGTTTTTCCCATTACTGACATGTATACTGAGTCATTAGGGACTTTCCAATGGGTTTTGCCCAGTACATAAGGTCAATAGGGGTG
AATCAACAGGAAAGTCCCATTGGAGCCAAGTACACTGAGTCAATAGGGACTTTCCATTGGGTTTTGCCCAGTACAAAAGGTCAATAGGGGGTGAGTCAATGGG
TTTTTCCCATTATTGGCACATACATAAGGTCAATAGGGGTGACTAGTGGAGAAGAGCATGCTTGAGGGCTGAGTGCCCCTCAGTGGGCAGAGAGCACATGGCC
CACAGTCCCTGAGAAGTTGGGGGGAGGGGTGGGCAATTGAACTGGTGCCTAGAGAAGGTGGGGCTTGGGTAAACTGGGAAAGTGATGTGGTGTACTGGCTC
CACCTTTTTCCCCAGGGTGGGGGAGAACCATATATAAGTGCAGTAGTCTCTGTGAACATTCAAGCTTCTGCCTTCTCCCTCCTGTGAGTTTGGTAAGTCACTGACT
GTCTATGCCTGGGAAAGGGTGGGCAGGAGATGGGGCAGTGCAGGAAAAGTGGCACTATGAACCCTGCAGCCCTAGACAATTGTACTAACCTTCTTCTCTTTCCT
CTCCTGACAGGTTGGTAACCAAGCTTTCCATGGGTTGGAGCCTCATCTTGCTCTTCCTTGTAGCTGTTGCTACTAGAGTCCTGTCCCAGGTACAACTGCAGCAGCC
TGGGGCTGAGCTGGTGAAGCCTGGGGCCTCAGTGAAGATGTCCTGCAAGGCTTCTGGCTACACATTTACCAGTTACAATATGCACTGGGTAAAACAGACACCTG
GTAGGGGCCTGGAATGGATTGGAGCTATTTATCCTGGAAATGGTGATACTTCCTACAATCAGAAGTTCAAAGGCAAGGCCACATTGACTGCAGACAAATCCTCC
AGCACAGCCTACATGCAGCTCAGCAGCCTGACATCTGAGGACTCTGCAGTCTATTACTGTGCAAGATCAACTTACTATGGTGGTGACTGGTACTTCAATGTCTGG
GGTGCAGGGACCACAGTCACAGTCTCTGCAGCAAGCACCAAGGGCCCATCTGTCTTCCCCCTGGCACCCTCCTCCAAGAGCACCTCTGGGGGCACAGCTGCCCT
GGGCTGCCTGGTCAAGGACTACTTCCCTGAACCTGTGACAGTGTCATGGAACTCAGGAGCCCTGACCAGTGGTGTGCACACCTTCCCTGCTGTCCTACAGTCCTC
AGGACTCTACTCCCTCAGCAGTGTGGTGACTGTGCCCTCCAGCAGCTTGGGCACCCAGACCTACATCTGCAATGTGAATCACAAGCCCAGCAACACCAAGGTGG
ACAAGAAAGCAGAGCCCAAATCTTGTGACAAAACTCACACATGCCCACCTTGCCCAGCACCTGAACTCCTGGGGGGACCTTCAGTCTTCCTCTTCCCCCCAAAAC
CCAAGGACACCCTCATGATCTCCAGGACCCCTGAGGTCACATGTGTGGTGGTGGATGTGAGCCATGAAGACCCTGAGGTCAAGTTCAACTGGTATGTGGATGG
TGTGGAGGTGCATAATGCCAAGACAAAGCCAAGGGAGGAGCAGTACAACAGCACTTACAGAGTGGTCAGTGTCCTCACTGTCCTGCACCAGGACTGGCTGAAT
GGCAAGGAGTACAAGTGCAAGGTCTCCAACAAAGCCCTCCCAGCCCCCATAGAGAAAACCATCTCCAAAGCCAAAGGGCAGCCCAGAGAACCACAGGTGTACA
CCCTGCCCCCATCCAGGGATGAGCTGACCAAGAACCAGGTCAGCCTGACCTGCCTGGTCAAAGGCTTCTATCCCAGTGACATTGCTGTGGAGTGGGAGAGCAAT
GGGCAGCCTGAGAACAACTACAAGACCACTCCTCCTGTGCTGGACTCTGATGGCTCCTTCTTCCTCTACAGCAAGCTCACAGTGGACAAGAGCAGGTGGCAGCA
GGGGAATGTCTTCTCATGCTCAGTCATGCATGAGGCTCTGCACAACCACTACACACAGAAGAGCCTCTCCCTGTCTCCAGGTAAATGATAGATCTACTTCTGGCT
AATAAAAGATCAGAGCTCTAGTGATCTGTGTGTTGGTTTTTTGTGTCTGCATTCTAGCAGGAGTCAATGGGAAAAACCCATTGGAGCCAAGTACACTGACTCAAT
AGGGACTTTCCATTGGGTTTTGCCCAGTACATAAGGTCAATAGGGGGTGAGTCAACAGGAAAGTCCCATTGGAGCCAAGTACATTGAGTCAATAGGGACTTTCC
AATGGGTTTTGCCCAGTACATAAGGTCAATGGGAGGTAAGCCAATGGGTTTTTCCCATTACTGACATGTATACTGAGTCATTAGGGACTTTCCAATGGGTTTTGC
CCAGTACATAAGGTCAATAGGGGTGAATCAACAGGAAAGTCCCATTGGAGCCAAGTACACTGAGTCAATAGGGACTTTCCATTGGGTTTTGCCCAGTACAAAAG
GTCAATAGGGGGTGAGTCAATGGGTTTTTCCCATTATTGGCACATACATAAGGTCAATAGGGGTGACTAGTGGAGAAGAGCATGCTTGAGGGCTGAGTGCCCC
TCAGTGGGCAGAGAGCACATGGCCCACAGTCCCTGAGAAGTTGGGGGGAGGGGTGGGCAATTGAACTGGTGCCTAGAGAAGGTGGGGCTTGGGTAAACTGG
GAAAGTGATGTGGTGTACTGGCTCCACCTTTTTCCCCAGGGTGGGGGAGAACCATATATAAGTGCAGTAGTCTCTGTGAACATTCAAGCTTCTGCCTTCTCCCTC
CTGTGAGTTTGGTAAGTCACTGACTGTCTATGCCTGGGAAAGGGTGGGCAGGAGATGGGGCAGTGCAGGAAAAGTGGCACTATGAACCCTGCAGCCCTAGAC
AATTGTACTAACCTTCTTCTCTTTCCTCTCCTGACAGGTTGGTAACCAAGCTTTCCATGGATTTTCAGGTGCAGATTATCAGCTTCCTCCTAATCAGTGCTTCAGTC
ATAATGTCCAGAGGACAAATTGTTCTCTCCCAGTCTCCAGCAATCCTGTCTGCATCTCCAGGGGAGAAGGTCACAATGACTTGCAGGGCCAGCTCAAGTGTAAG
TTACATCCACTGGTTCCAGCAGAAGCCAGGATCCTCCCCCAAACCCTGGATTTATGCCACATCCAACCTGGCTTCTGGAGTCCCTGTTAGATTCAGTGGCAGTGG
GTCTGGGACTTCTTACTCTCTCACCATCAGCAGAGTGGAGGCTGAAGATGCTGCCACTTATTACTGCCAGCAGTGGACTAGTAACCCACCCACTTTTGGAGGGG
GGACCAAGCTGGAAATCAAAAGAACAGTGGCTGCACCATCTGTCTTCATCTTCCCTCCATCTGATGAGCAGTTGAAATCTGGAACTGCCTCTGTTGTGTGCCTGC
TGAATAACTTCTATCCCAGAGAGGCCAAAGTACAGTGGAAGGTGGATAATGCCCTCCAATCAGGTAACTCCCAGGAGAGTGTCACAGAGCAGGACAGCAAGGA
CAGCACCTACAGCCTCAGCAGCACCCTGACACTGAGCAAAGCAGACTATGAGAAACACAAAGTCTATGCCTGTGAAGTCACCCATCAGGGCCTGAGCTCTCCTG
TCACAAAGAGCTTCAACAGGGGAGAGTCTTGATAGATCTACTTCTGGCTAATAAAAGATCAGAGCTCTAGTGATCTGTGTGTTGGTTTTTTGTGTCTGCATTCTA
GCTCTAGTGATCAGCAGTTCAACCTGTTGATAGTATGTACTAAGCTCTCATGTTTAATGTACTAAGCTCTCATGTTTAATGAACTAAACCCTCATGGCTAATGTACT
AAGCTCTCATGGCTAATGTACTAAGCTCTCATGTTTCATGTACTAAGCTCTCATGTTTGAACAATAAAATTAATATAAATCAGCAACTTAAATAGCCTCTAAGGTTT
TAAGTTTTATAAGAAAAAAAAGAATATATAAGGCTTTTAAAGGTTTTAAGGTTTCCTAGGTTATCCTCATATGAGCTCTTAGAAAAACTCATCCAGCATCAAATGA
AACTGCAATTTATTCATATCAGGATTATCAATACCATATTTTTGAAAAAGTCTTTTCTGTAATGAAGGAGAAAACTCACCCAGGCAGTTCCATAGGATGGCAAGA
TCCTGGTATCTGTCTGCAATTCCAACTCTTCCAACATCAATACAACCTATTAATTTCCCCTCATCAAAAATAAGGTTATCAAGTGAGAAATCACCATGAGTGACCAC
TGAATCTGGTGAGAATGGCAAAAGATTATGCATTTCTTTCCAGACTTGTTCAACAGGCCAGCCATTTCTCTCATCATCAAAATCACTGGCATCAACCAAACCATTA
TTCATTCTTGATTGGGCCTGAGCCAGTCTAAATACTCTATCAGAGTTAAAAGGACAATTACAAACAGGAATGGAATGCAATCTTCTCAGGAACACTGCCAGGGC
ATCAACAATATTTTCACCTGAATCAGGATATTCTTCCAATACCTGGAATGCTGTTTTCCCTGGGATGGCAGTGGTGAGTAACCATGCATCATCAGGAGTTCTGATA
AAATGCTTGATGGTTGGAAGAGGCATAAATTCAGTCAGCCAGTTTAGTCTGACCATCTCATCTGTAACATCATTGGCAACAGAACCTTTGCCATGTTTCAGAAAC
AACTCTGGGGCATCTGGCTTCCCATACAATCTATAGATTGTGGCACCTGATTGCCCAACATTATCTCTAGCCCATTTATACCCATATAAATCAGCATCCATGTTGG
AATTTAATCTTGGCCTGGAGCAAGAGGTTTCTCTTTGAATATGGCTCATACATGTGCACCTCCTATAGTGAGTTGTATTATACTATGCAGATATACTATGCCAATG
TTTAATTGTCAG

FIG. 41

Dual Cassette CpG-Free Non-Optimized anti-CD20 plasmids construct (SEQ ID NO:7)

4 : DraIII-RINhe-ΔmCMVΔEF1I126-antiCD20-H-BglII-MixpA -ΔmCMVΔEF1I126-BstEII-antiCD20-L-BglII-MixpA/BV2

CACTATGTGGACATGAATTCAATTGGCTAGCAGGAGTCAATGGGAAAAACCCATTGGAGCCAAGTACACTGACTCAATAGGGACTTTCCATTGGGTTTTGCCCA
GTACATAAGGTCAATAGGGGGTGAGTCAACAGGAAAGTCCCATTGGAGCCAAGTACATTGAGTCAATAGGGACTTTCCAATGGGTTTTGCCCAGTACATAAGG
TCAATGGGAGGTAAGCCAATGGGTTTTTCCCATTACTGACATGTATACTGAGTCATTAGGGACTTTCCAATGGGTTTTGCCCAGTACATAAGGTCAATAGGGGTG
AATCAACAGGAAAGTCCCATTGGAGCCAAGTACACTGAGTCAATAGGGACTTTCCATTGGGTTTTGCCCAGTACAAAAGGTCAATAGGGGGTGAGTCAATGGG
TTTTTCCCATTATTGGCACATACATAAGGTCAATAGGGGTGACTAGTGGAGAAGAGCATGCTTGAGGGCTGAGTGCCCCTCAGTGGGCAGAGAGCACATGGCC
CACAGTCCCTGAGAAGTTGGGGGGAGGGGTGGGCAATTGAACTGGTGCCTAGAGAAGGTGGGGCTTGGGTAAACTGGGAAAGTGATGTGGTGTACTGGCTC
CACCTTTTTCCCCAGGGTGGGGGAGAACCATATATAAGTGCAGTAGTCTCTGTGAACATTCAAGCTTCTGCCTTCTCCCTCCTGTGAGTTTGGTAAGTCACTGACT
GTCTATGCCTGGGAAAGGGTGGGCAGGAGATGGGGCAGTGCAGGAAAAGTGGCACTATGAACCCTGCAGCCCTAGACAATTGTACTAACCTTCTTCTCTTTCCT
CTCCTGACAGGTTGGTAACCTGACAGGTTGGTAACCAAGCTTTCCATGGGTTGGAGCCTCATCTTGCTCTTCCTTGTCGCTGTTGCTACGCGTGTCCTGTCCCAGG
TACAACTGCAGCAGCCTGGGGCTGAGCTGGTGAAGCCTGGGGCCTCAGTGAAGATGTCCTGCAAGGCTTCTGGCTACACATTTACCAGTTACAATATGCACTGG
GTAAAACAGACACCTGGTCGGGGCCTGGAATGGATTGGAGCTATTTATCCCGGAAATGGTGATACTTCCTACAATCAGAAGTTCAAAGGCAAGGCCACATTGAC
TGCAGACAAATCCTCCAGCACAGCCTACATGCAGCTCAGCAGCCTGACATCTGAGGACTCTGCGGTCTATTACTGTGCAAGATCGACTTACTACGGCGGTGACT
GGTACTTCAATGTCTGGGGCGCAGGGACCACGGTCACCGTCTCTGCAGCTAGCACCAAGGGCCCATCGGTCTTCCCCCTGGCACCCTCCTCCAAGAGCACCTCT
GGGGGCACAGCGGCCCTGGGCTGCCTGGTCAAGGACTACTTCCCCGAACCGGTGACGGTGTCGTGGAACTCAGGCGCCCTGACCAGCGGCGTGCACACCTTCC
CGGCTGTCCTACAGTCCTCAGGACTCTACTCCCTCAGCAGCGTGGTGACCGTGCCCTCCAGCAGCTTGGGCACCCAGACCTACATCTGCAACGTGAATCACAAGC
CCAGCAACACCAAGGTGGACAAGAAAGCAGAGCCCAAATCTTGTGACAAAACTCACACATGCCCACCGTGCCCAGCACCTGAACTCCTGGGGGGACCGTCAGT
CTTCCTCTTCCCCCCAAAACCCAAGGACACCCTCATGATCTCCCGGACCCCTGAGGTCACATGCGTGGTGGTGGACGTGAGCCACGAAGACCCTGAGGTCAAGT
TCAACTGGTACGTGGACGGCGTGGAGGTGCATAATGCCAAGACAAAGCCGCGGGAGGAGCAGTACAACAGCACGTACCGTGTGGTCAGCGTCCTCACCGTCCT
GCACCAGGACTGGCTGAATGGCAAGGAGTACAAGTGCAAGGTCTCCAACAAAGCCCTCCCAGCCCCCATCGAGAAAACCATCTCCAAAGCCAAAGGGCAGCCC
CGAGAACCACAGGTGTACACCCTGCCCCCATCCCGGGATGAGCTGACCAAGAACCAGGTCAGCCTGACCTGCCTGGTCAAAGGCTTCTATCCCAGCGACATCGC
CGTGGAGTGGGAGAGCAATGGGCAGCCGGAGAACAACTACAAGACCACGCCTCCCGTGCTGGACTCCGACGGCTCCTTCTTCCTCTACAGCAAGCTCACCGTG
GACAAGAGCAGGTGGCAGCAGGGGAACGTCTTCTCATGCTCCGTCATGCATGAGGCTCTGCACAACCACTACACGCAGAAGAGCCTCTCCCTGTCTCCGGGTAA
ATGATAGATCTACTTCTGGCTAATAAAAGATCAGAGCTCTAGTGATCTGTGTGTTGGTTTTTTGTGTCTGCATTCTAGCAGGAGTCAATGGGAAAAACCCATTGG
AGCCAAGTACACTGACTCAATAGGGACTTTCCATTGGGTTTTGCCCAGTACATAAGGTCAATAGGGGGTGAGTCAACAGGAAAGTCCCATTGGAGCCAAGTACA
TTGAGTCAATAGGGACTTTCCAATGGGTTTTGCCCAGTACATAAGGTCAATGGGAGGTAAGCCAATGGGTTTTTCCCATTACTGACATGTATACTGAGTCATTAG
GGACTTTCCAATGGGTTTTGCCCAGTACATAAGGTCAATAGGGGTGAATCAACAGGAAAGTCCCATTGGAGCCAAGTACACTGAGTCAATAGGGACTTTCCATT
GGGTTTTGCCCAGTACAAAAGGTCAATAGGGGGTGAGTCAATGGGTTTTTCCCATTATTGGCACATACATAAGGTCAATAGGGGTGACTAGTGGAGAAGAGCA
TGCTTGAGGGCTGAGTGCCCCTCAGTGGGCAGAGAGCACATGGCCCACAGTCCCTGAGAAGTTGGGGGGAGGGGTGGGCAATTGAACTGGTGCCTAGAGAA
GGTGGGGCTTGGGTAAACTGGGAAAGTGATGTGGTGTACTGGCTCCACCTTTTTCCCCAGGGTGGGGGAGAACCATATATAAGTGCAGTAGTCTCTGTGAACA
TTCAAGCTTCTGCCTTCTCCCTCCTGTGAGTTTGGTAAGTCACTGACTGTCTATGCCTGGGAAAGGGTGGGCAGGAGATGGGGCAGTGCAGGAAAAGTGGCACT
ATGAACCCTGCAGCCCTAGACAATTGTACTAACCTTCTTCTCTTTCCTCTCCTGACAGGTTGGTAACCAAGCTTTCCATGGATTTTCAGGTGCAGATTATCAGCTTC
CTCCTAATCAGTGCTTCAGTCATAATGTCCAGAGGACAAATTGTTCTCTCCCAGTCTCCAGCAATCCTGTCTGCATCTCCAGGGGAGAAGGTCACAATGACTTGC
AGGGCCAGCTCAAGTGTAAGTTACATCCACTGGTTCCAGCAGAAGCCAGGATCCTCCCCCAAACCCTGGATTTATGCCACATCCAACCTGGCTTCTGGAGTCCCT
GTTCGCTTCAGTGGCAGTGGGTCTGGGACTTCTTACTCTCTCACCATCAGCAGAGTGGAGGCTGAAGATGCTGCCACTTATTACTGCCAGCAGTGGACTAGTAA
CCCACCCACGTTCGGAGGGGGGACCAAGCTGGAAATCAAACGTACGGTGGCTGCACCATCTGTCTTCATCTTCCCGCCATCTGATGAGCAGTTGAAATCTGGAA
CTGCCTCTGTTGTGTGCCTGCTGAATAACTTCTATCCCAGAGAGGCCAAAGTACAGTGGAAGGTGGATAACGCCCTCCAATCGGGTAACTCCCAGGAGAGTGTC
ACAGAGCAGGACAGCAAGGACAGCACCTACAGCCTCAGCAGCACCCTGACGCTGAGCAAAGCAGACTACGAGAAACACAAAGTCTACGCCTGCGAAGTCACCC
ATCAGGGCCTGAGCTCGCCCGTCACAAAGAGCTTCAACAGGGGAGAGTCTTGATAGATCTACTTCTGGCTAATAAAAGATCAGAGCTCTAGTGATCTGTGTGTT
GGTTTTTTGTGTCTGCATTCTAGCTCTAGTGATCAGCAGTTCAACCTGTTGATAGTATGTACTAAGCTCTCATGTTTAATGTACTAAGCTCTCATGTTTAATGAACT
AAACCCTCATGGCTAATGTACTAAGCTCTCATGGCTAATGTACTAAGCTCTCATGTTTCATGTACTAAGCTCTCATGTTTGAACAATAAAATTAATATAAATCAGC
AACTTAAATAGCCTCTAAGGTTTTAAGTTTTATAAGAAAAAAAAGAATATATAAGGCTTTTAAAGGTTTTAAGGTTTCCTAGGTTATCCTCATATGAGCTCTTAGA
AAAACTCATCCAGCATCAAATGAAACTGCAATTTATTCATATCAGGATTATCAATACCATATTTTTGAAAAAGTCTTTTCTGTAATGAAGGAGAAAACTCACCCAG
GCAGTTCCATAGGATGGCAAGATCCTGGTATCTGTCTGCAATTCCAACTCTTCCAACATCAATACAACCTATTAATTTCCCCTCATCAAAAATAAGGTTATCAAGT
GAGAAATCACCATGAGTGACCACTGAATCTGGTGAGAATGGCAAAAGATTATGCATTTCTTTCCAGACTTGTTCAACAGGCCAGCCATTTCTCTCATCATCAAAA
TCACTGGCATCAACCAAACCATTATTCATTCTTGATTGGGCCTGAGCCAGTCTAAATACTCTATCAGAGTTAAAAGGACAATTACAAACAGGAATGGAATGCAAT
CTTCTCAGGAACACTGCCAGGGCATCAACAATATTTTCACCTGAATCAGGATATTCTTCCAATACCTGGAATGCTGTTTTCCCTGGGATGGCAGTGGTGAGTAAC
CATGCATCATCAGGAGTTCTGATAAAATGCTTGATGGTTGGAAGAGGCATAAATTCAGTCAGCCAGTTTAGTCTGACCATCTCATCTGTAACATCATTGGCAACA
GAACCTTTGCCATGTTTCAGAAACAACTCTGGGGCATCTGGCTTCCCATACAATCTATAGATTGTGGCACCTGATTGCCCAACATTATCTCTAGCCCATTTATACCC
ATATAAATCAGCATCCATGTTGGAATTTAATCTTGGCCTGGAGCAAGAGGTTTCTCTTTGAATATGGCTCATACATGTGCACCTCCTATAGTGAGTTGTATTATAC
TATGCAGATATACTATGCCAATGTTTAATTGTCAG

FIG. 42

Dual Cassette MAR-less Optimized anti-CD20 plasmids construct (SEQ ID NO:8)

4 : DraIII-RINhe-ΔmCMVΔEF1I126-BstEII-OurKΔantiCD20-H-BglII-MixpA -ΔmCMVΔEF1I126-BstEII-GAKΔantiCD20-L-BglII-MixpA/BV2

CACTATGTGGACATGAATTCAATTGGCTAGCAGGAGTCAATGGGAAAAACCCATTGGAGCCAAGTACACTGACTCAATAGGGACTTTCCATTGGGTTTTGCCCA
GTACATAAGGTCAATAGGGGGTGAGTCAACAGGAAAGTCCCATTGGAGCCAAGTACATTGAGTCAATAGGGACTTTCCAATGGGTTTTGCCCAGTACATAAGG
TCAATGGGAGGTAAGCCAATGGGTTTTTCCCATTACTGACATGTATACTGAGTCATTAGGGACTTTCCAATGGGTTTTGCCCAGTACATAAGGTCAATAGGGGTG
AATCAACAGGAAAGTCCCATTGGAGCCAAGTACACTGAGTCAATAGGGACTTTCCATTGGGTTTTGCCCAGTACAAAAGGTCAATAGGGGGTGAGTCAATGGG
TTTTTCCCATTATTGGCACATACATAAGGTCAATAGGGGTGACTAGTGGAGAAGAGCATGCTTGAGGGCTGAGTGCCCCTCAGTGGGCAGAGAGCACATGGCC
CACAGTCCCTGAGAAGTTGGGGGGAGGGGTGGGCAATTGAACTGGTGCCTAGAGAAGGTGGGGCTTGGGTAAACTGGGAAAGTGATGTGGTGTACTGGCTC
CACCTTTTTCCCCAGGGTGGGGGAGAACCATATATAAGTGCAGTAGTCTCTGTGAACATTCAAGCTTCTGCCTTCTCCCTCCTGTGAGTTTGGTAAGTCACTGACT
GTCTATGCCTGGGAAAGGGTGGGCAGGAGATGGGGCAGTGCAGGAAAAGTGGCACTATGAACCCTGCAGCCCTAGACAATTGTACTAACCTTCTTCTCTTTCCT
CTCCTGACAGGTTGGTAACCAAGCTTTCCATGGGCTGGTCCCTGATCCTGCTGTTCCTGGTGGCTGTGGCCACCAGAGTGCTGAGCCAGGTGCAGCTGCAGCAG
CCTGGGGCTGAGCTTGTGAAACCTGGGGCCTCTGTGAAGATGAGCTGCAAGGCCTCTGGCTACACCTTCACCAGCTACAACATGCACTGGGTCAAGCAGACCCC
TGGCAGAGGCCTGGAATGGATTGGAGCCATCTACCCTGGCAATGGGGACACCTCCTACAACCAGAAGTTCAAGGGCAAGGCCACCCTGACAGCTGACAAGAGC
AGCAGCACAGCCTACATGCAGCTGTCCAGCCTGACCTCTGAGGACTCTGCTGTGTACTACTGTGCCAGGTCCACCTACTATGGGGGAGACTGGTACTTCAATGT
GTGGGGAGCTGGCACCACAGTGACAGTGTCTGCTGCCAGCACCAAGGGCCCCTCTGTGTTTCCTCTGGCCCCCAGCAGCAAGAGCACCTCTGGGGGAACAGCT
GCCCTGGGCTGCCTTGTGAAGGACTACTTCCCTGAGCCTGTGACTGTGTCCTGGAACTCTGGGGCCCTGACATCTGGGGTGCACACCTTCCCTGCAGTGCTGCA
GTCCAGTGGCCTGTACTCCCTGTCCTCTGTTGTGACAGTGCCCAGCTCCAGCCTGGGCACCCAGACCTACATCTGCAATGTGAACCACAAGCCCAGCAACACCAA
GGTGGACAAGAAGGCTGAGCCCAAGAGCTGTGACAAGACCCACACCTGTCCCCCCTGTCCTGCCCCTGAACTGCTGGGAGGACCTTCTGTGTTCCTGTTCCCAC
CCAAGCCCAAGGATACCCTGATGATCAGCAGAACCCCTGAAGTGACCTGTGTGGTGGTGGATGTGTCCCATGAGGACCCAGAAGTGAAGTTCAATTGGTATGT
GGATGGGGTGGAAGTGCACAATGCCAAGACCAAGCCCAGAGAGGAACAGTACAACAGCACCTACAGAGTGGTGTCTGTGCTGACTGTGCTGCACCAGGACTG
GCTGAATGGCAAAGAGTACAAGTGCAAGGTGTCCAACAAGGCCCTGCCAGCCCCCATTGAGAAAACCATCAGCAAGGCCAAGGGCCAGCCTAGAGAACCCCA
GGTGTACACACTGCCCCCTAGCAGGGATGAGCTGACCAAGAACCAGGTGTCCCTGACATGCCTTGTGAAAGGCTTCTACCCCTCTGACATTGCTGTGGAATGGG
AGAGCAATGGACAGCCTGAGAACAACTACAAGACCACCCCCCCTGTGCTGGACTCTGATGGCTCATTCTTCCTGTACAGCAAGCTGACAGTGGACAAGTCCAGA
TGGCAGCAGGGCAATGTGTTCAGCTGCTCTGTGATGCATGAGGCCCTGCACAACCACTACACCCAGAAAAGCCTGTCCCTGTCCCCTGGCAAGTGAAGATCTAC
TTCTGGCTAATAAAAGATCAGAGCTCTAGTGATCTGTGTGTTGGTTTTTTGTGTCTGCATTCTAGCAGGAGTCAATGGGAAAAACCCATTGGAGCCAAGTACACT
GACTCAATAGGGACTTTCCATTGGGTTTTGCCCAGTACATAAGGTCAATAGGGGGTGAGTCAACAGGAAAGTCCCATTGGAGCCAAGTACATTGAGTCAATAG
GGACTTTCCAATGGGTTTTGCCCAGTACATAAGGTCAATGGGAGGTAAGCCAATGGGTTTTTCCCATTACTGACATGTATACTGAGTCATTAGGGACTTTCCAAT
GGGTTTTGCCCAGTACATAAGGTCAATAGGGGTGAATCAACAGGAAAGTCCCATTGGAGCCAAGTACACTGAGTCAATAGGGACTTTCCATTGGGTTTTGCCCA
GTACAAAAGGTCAATAGGGGGTGAGTCAATGGGTTTTTCCCATTATTGGCACATACATAAGGTCAATAGGGGTGACTAGTGGAGAAGAGCATGCTTGAGGGCT
GAGTGCCCCTCAGTGGGCAGAGAGCACATGGCCCACAGTCCCTGAGAAGTTGGGGGGAGGGGTGGGCAATTGAACTGGTGCCTAGAGAAGGTGGGGCTTGG
GTAAACTGGGAAAGTGATGTGGTGTACTGGCTCCACCTTTTTCCCCAGGGTGGGGGAGAACCATATATAAGTGCAGTAGTCTCTGTGAACATTCAAGCTTCTGC
CTTCTCCCTCCTGTGAGTTTGGTAAGTCACTGACTGTCTATGCCTGGGAAAGGGTGGGCAGGAGATGGGGCAGTGCAGGAAAAGTGGCACTATGAACCCTGCA
GCCCTAGACAATTGTACTAACCTTCTTCTCTTTCCTCTCCTGACAGGTTGGTAACCAAGCCACCATGGACTTCCAGGTGCAGATCATCAGCTTTCTGCTGATCTCTG
CCTCTGTGATCATGAGCAGAGGCCAGATTGTGCTGAGCCAGAGCCCTGCCATCCTGTCTGCAAGCCCTGGGGAGAAAGTGACCATGACCTGCAGAGCCAGCAG
CTCTGTGTCCTACATCCACTGGTTCCAGCAGAAGCCTGGCAGCAGCCCCAAGCCTTGGATCTATGCCACCAGCAACCTGGCATCTGGGGTGCCAGTCAGATTCTC
TGGCTCTGGATCTGGCACCAGCTACAGCCTGACCATCAGCAGAGTGGAAGCTGAGGATGCTGCCACCTACTACTGCCAGCAGTGGACCAGCAATCCCCCCACCT
TTGGAGGGGGCACCAAGCTGGAAATCAAGAGAACAGTGGCTGCCCCCTCTGTGTTCATCTTCCCACCCTCTGATGAGCAGCTGAAGTCTGGAACAGCCTCTGTT
GTGTGCCTGCTGAACAACTTCTACCCCAGAGAAGCCAAGGTGCAGTGGAAGGTGGACAATGCCCTGCAGTCTGGCAACTCCCAGGAATCTGTGACAGAGCAGG
ACAGCAAGGACTCCACCTACTCCCTGAGCAGCACCCTGACCCTGAGCAAGGCTGACTATGAGAAGCACAAAGTGTATGCCTGTGAAGTGACCCACCAGGGCCT
GTCCAGCCCTGTGACCAAGAGCTTCAACAGAGGGGAGAGCTGAAGATCTACTTCTGGCTAATAAAAGATCAGAGCTCTAGTGATCTGTGTGTTGGTTTTTTGTG
TCTGCATTCTAGCTCTAGTGATCAGCAGTTCAACCTGTTGATAGTATGTACTAAGCTCTCATGTTTAATGTACTAAGCTCTCATGTTTAATGAACTAAACCCTCATG
GCTAATGTACTAAGCTCTCATGGCTAATGTACTAAGCTCTCATGTTTCATGTACTAAGCTCTCATGTTTGAACAATAAAATTAATATAAATCAGCAACTTAAATAG
CCTCTAAGGTTTTAAGTTTTATAAGAAAAAAAAGAATATATAAGGCTTTTAAAGGTTTTAAGGTTTCCTAGGTTATCCTCATATGAGCTCTTAGAAAAACTCATCC
AGCATCAAATGAAACTGCAATTTATTCATATCAGGATTATCAATACCATATTTTTGAAAAAGTCTTTTCTGTAATGAAGGAGAAAACTCACCCAGGCAGTTCCATA
GGATGGCAAGATCCTGGTATCTGTCTGCAATTCCAACTCTTCCAACATCAATACAACCTATTAATTTCCCCTCATCAAAAATAAGGTTATCAAGTGAGAAATCACC
ATGAGTGACCACTGAATCTGGTGAGAATGGCAAAAGATTATGCATTTCTTTCCAGACTTGTTCAACAGGCCAGCCATTTCTCTCATCATCAAAATCACTGGCATCA
ACCAAACCATTATTCATTCTTGATTGGGCCTGAGCCAGTCTAAATACTCTATCAGAGTTAAAAGGACAATTACAAACAGGAATGGAATGCAATCTTCTCAGGAAC
ACTGCCAGGGCATCAACAATATTTTCACCTGAATCAGGATATTCTTCCAATACCTGGAATGCTGTTTTCCCTGGGATGGCAGTGGTGAGTAACCATGCATCATCA
GGAGTTCTGATAAAATGCTTGATGGTTGGAAGAGGCATAAATTCAGTCAGCCAGTTTAGTCTGACCATCTCATCTGTAACATCATTGGCAACAGAACCTTTGCCA
TGTTTCAGAAACAACTCTGGGGCATCTGGCTTCCCATACAATCTATAGATTGTGGCACCTGATTGCCCAACATTATCTCTAGCCCATTTATACCCATATAAATCAG
CATCCATGTTGGAATTTAATCTTGGCCTGGAGCAAGAGGTTTCTCTTTGAATATGGCTCATACATGTGCACCTCCTATAGTGAGTTGTATTATACTATGCAGATAT
ACTATGCCAATGTTTAATTGTCAG

FIG. 43

Dual Cassette MAR-Containing Optimized anti-CD20 plasmids construct (SEQ ID NO:9)

6 : DraIII-βGlo-RINhe-ΔmCMVΔEF1I126-BstEII-GAKΔantiCD20-H-BglII-MixpA-21q21- -ΔmCMVΔEF1I126-BstEII-GAKΔantiCD20-L-BglII-MixpA-IFN-/BV3 : 7413bp

CACTATGTGTTAATTAAAATTATCTCTAAGGCATGTGAACTGGCTGTCTTGGTTTTCATCTGTACTTCATCTGCTACCTCTGTGACCTGAAACATATTTATAATTCCA
TTAAGCTGTGCATATGATAGATTTATCATATGTATTTTCCTTAAAGGATTTTTGTAAGAACTAATTGAATTGATACCTGTAAAGTCTTTATCACACTACCCAATAAA
TAATAAATCTCTTTGTTCAGCTCTCTGTTTCTATAAATATGTACCAGTTTTATTGTTTTTAGTGGTAGTGATTTTATTCTCTTTCTATATATATACACACACATGTGTG
CATTCATAAATATATACAATTTTTATGAATAAAAAATTATTAGCAATCAATATTGAAAACCACTGATTTTTGTTTATGTGAGCAAACAGCAGATTAAAAGGAATTT
GAATTCTCATAGCTAGCAGGAGTCAATGGGAAAAACCCATTGGAGCCAAGTACACTGACTCAATAGGGACTTTCCATTGGGTTTTGCCCAGTACATAAGGTCAA
TAGGGGGTGAGTCAACAGGAAAGTCCCATTGGAGCCAAGTACATTGAGTCAATAGGGACTTTCCAATGGGTTTTGCCCAGTACATAAGGTCAATGGGAGGTAA
GCCAATGGGTTTTTCCCATTACTGACATGTATACTGAGTCATTAGGGACTTTCCAATGGGTTTTGCCCAGTACATAAGGTCAATAGGGGTGAATCAACAGGAAA
GTCCCATTGGAGCCAAGTACACTGAGTCAATAGGGACTTTCCATTGGGTTTTGCCCAGTACAAAAGGTCAATAGGGGGTGAGTCAATGGGTTTTTCCCATTATTG
GCACATACATAAGGTCAATAGGGGTGACTAGTGGAGAAGAGCATGCTTGAGGGCTGAGTGCCCCTCAGTGGGCAGAGAGCACATGGCCCACAGTCCCTGAGA
AGTTGGGGGGAGGGGTGGGCAATTGAACTGGTGCCTAGAGAAGGTGGGGCTTGGGTAAACTGGGAAAGTGATGTGGTGTACTGGCTCCACCTTTTTCCCCAG
GGTGGGGGAGAACCATATATAAGTGCAGTAGTCTCTGTGAACATTCAAGCTTCTGCCTTCTCCCTCCTGTGAGTTTGGTAAGTCACTGACTGTCTATGCCTGGGA
AAGGGTGGGCAGGAGATGGGGCAGTGCAGGAAAAGTGGCACTATGAACCCTGCAGCCCTAGACAATTGTACTAACCTTCTTCTCTTTCCTCTCCTGACAGGTTG
GTAACCAAGCCACCATGGGCTGGTCCCTGATCCTGCTGTTCCTGGTGGCTGTGGCCACCAGAGTGCTGAGCCAGGTGCAGCTGCAGCAGCCTGGGGCTGAGCT
TGTGAAACCTGGGGCCTCTGTGAAGATGAGCTGCAAGGCCTCTGGCTACACCTTCACCAGCTACAACATGCACTGGGTCAAGCAGACCCCTGGCAGAGGCCTG
GAATGGATTGGAGCCATCTACCCTGGCAATGGGGACACCTCCTACAACCAGAAGTTCAAGGGCAAGGCCACCCTGACAGCTGACAAGAGCAGCAGCACAGCCT
ACATGCAGCTGTCCAGCCTGACCTCTGAGGACTCTGCTGTGTACTACTGTGCCAGGTCCACCTACTATGGGGGAGACTGGTACTTCAATGTGTGGGGAGCTGGC
ACCACAGTGACAGTGTCTGCTGCCAGCACCAAGGGCCCCTCTGTGTTTCCTCTGGCCCCCAGCAGCAAGAGCACCTCTGGGGGAACAGCTGCCCTGGGCTGCCT
TGTGAAGGACTACTTCCCTGAGCCTGTGACTGTGTCCTGGAACTCTGGGGCCCTGACATCTGGGGTGCACACCTTCCCTGCAGTGCTGCAGTCCAGTGGCCTGT
ACTCCCTGTCCTCTGTTGTGACAGTGCCCAGCTCCAGCCTGGGCACCCAGACCTACATCTGCAATGTGAACCACAAGCCCAGCAACACCAAGGTGGACAAGAAG
GCTGAGCCCAAGAGCTGTGACAAGACCCACACCTGTCCCCCCTGTCCTGCCCCTGAACTGCTGGGAGGACCTTCTGTGTTCCTGTTCCCACCCAAGCCCAAGGAT
ACCCTGATGATCAGCAGAACCCCTGAAGTGACCTGTGTGGTGGTGGATGTGTCCCATGAGGACCCAGAAGTGAAGTTCAATTGGTATGTGGATGGGGTGGAAG
TGCACAATGCCAAGACCAAGCCCAGAGAGGAACAGTACAACAGCACCTACAGAGTGGTGTCTGTGCTGACTGTGCTGCACCAGGACTGGCTGAATGGCAAAGA
GTACAAGTGCAAGGTGTCCAACAAGGCCCTGCCAGCCCCCATTGAGAAAACCATCAGCAAGGCCAAGGGCCAGCCTAGAGAACCCCAGGTGTACACACTGCCC
CCTAGCAGGGATGAGCTGACCAAGAACCAGGTGTCCCTGACATGCCTTGTGAAAGGCTTCTACCCCTCTGACATTGCTGTGGAATGGGAGAGCAATGGACAGC
CTGAGAACAACTACAAGACCACCCCCCCTGTGCTGGACTCTGATGGCTCATTCTTCCTGTACAGCAAGCTGACAGTGGACAAGTCCAGATGGCAGCAGGGCAAT
GTGTTCAGCTGCTCTGTGATGCATGAGGCCCTGCACAACCACTACACCCAGAAAAGCCTGTCCCTGTCCCCTGGCAAGTGAAGATCTACTTCTGGCTAATAAAAG
ATCAGAGCTCTAGTGATCTGTGTGTTGGTTTTTTGTGTCTGCATTCTAGCAGAGCCCCACTGTGTTCATCTTACAGATGGAAATACTGACATTCAGAGGAGT
TAGTTAACTTGCCTAGGTGATTCAGCTAATAAGTGCAAGAAAGATTTCAATCCAAGGTGATTTGATTCTGAAGCCTGTGCTAATCACATTACACCAA
GCTACAACTTCATTTATAAATAATAAGTCAGCTTTCAAGGGCCTTTCAGGTGTCCTGCACTTCTACAAGCTGTGCCATTTAGTGAACACAAAATGAG
CCTTCTGATGAAGTAGTCTTTTCATTATTTCAGATATTAGAACACTAAAATTCTTAGCTGCCAGCTGATTGAAGGCTGGGACAAAATTCAAACATGC
ATCTACAACAATATATATCTCAATGTTAGTCTCCAAATTCTATTGACTTCAACTCAAGAGAATATAAAGAGCTAGTCTTTATACACTCTTTAAGGTA
TGATATCATCTGGAAAGTAACAAAATTGATGCAAATTTGAATGAACTTTATCATGGTGTATTTACACAATGTGTTTCTTCTCCCTGCAATGTATTTC
TTTCTCTAATTCCTTCCATTTGATCTTTCATACACAATCTGGTTCTGATGTATGTTTTTTGGATGCACTTTTCAACTCCAAAAGACAGAGCTAGTTA
CTTTCTTCCTGGTGCTCCAAGCACTGTATTTGTATCTGTATTCAAGCCCTTTGCAATATTGTACTGGATCATTATTTCACCTCTAGGATGGCTTCCC
CAGGCAACTTGTGTTCACCCAGAGACTACATTTTGTATCTTGTTGACCTTTGAACTTCCACCAGTGTCTAAAAATAATATGTATGCAAAATTACTTG
CTATGAGAATGTATAATTAAACAATATAAAAAGGAGAAGCAAGGAGAGAAACACAGGTGTGTATTTGTGTTTGTGTGCTTAAAAGGCAGTGTGGAAA
AGGAAGAAATGCCATTTATAGTGAGGAGACAAAGTTATATTACCTCTTATCTGGCTTTTAAGGAGATTTTGCTGAGCTAAAAATCCTATATTCATAG
AAAAGCCTTACCTGAGTTGCCAATACCTCAATTCAGTCTAGCAGGAGTCAATGGGAAAAACCCATTGGAGCCAAGTACACTGACTCAATAGGGACTTTCCA
TTGGGTTTTGCCCAGTACATAAGGTCAATAGGGGGTGAGTCAACAGGAAAGTCCCATTGGAGCCAAGTACATTGAGTCAATAGGGACTTTCCAATGGGTTTTGC
CCAGTACATAAGGTCAATGGGAGGTAAGCCAATGGGTTTTTCCCATTACTGACATGTATACTGAGTCATTAGGGACTTTCCAATGGGTTTTGCCCAGTACATAAG
GTCAATAGGGGTGAATCAACAGGAAAGTCCCATTGGAGCCAAGTACACTGAGTCAATAGGGACTTTCCATTGGGTTTTGCCCAGTACAAAAGGTCAATAGGGG
GTGAGTCAATGGGTTTTTCCCATTATTGGCACATACATAAGGTCAATAGGGGTGACTAGTGGAGAAGAGCATGCTTGAGGGCTGAGTGCCCCTCAGTGGGCAG
AGAGCACATGGCCCACAGTCCCTGAGAAGTTGGGGGGAGGGGTGGGCAATTGAACTGGTGCCTAGAGAAGGTGGGGCTTGGGTAAACTGGGAAAGTGATGT
GGTGTACTGGCTCCACCTTTTTCCCCAGGGTGGGGGAGAACCATATATAAGTGCAGTAGTCTCTGTGAACATTCAAGCTTCTGCCTTCTCCCTCCTGTGAGTTTG
GTAAGTCACTGACTGTCTATGCCTGGGAAAGGGTGGGCAGGAGATGGGGCAGTGCAGGAAAAGTGGCACTATGAACCCTGCAGCCCTAGACAATTGTACTAA
CCTTCTTCTCTTTCCTCTCCTGACAGGTTGGTAACCAAGCCACCATGGACTTCCAGGTGCAGATCATCAGCTTTCTGCTGATCTCTGCCTCTGTGATCATGAGCAGA
GGCCAGATTGTGCTGAGCCAGAGCCCTGCCATCCTGTCTGCAAGCCCTGGGGAGAAAGTGACCATGACCTGCAGAGCCAGCAGCTCTGTGTCCTACATCCACTG
GTTCCAGCAGAAGCCTGGCAGCAGCCCCAAGCCTTGGATCTATGCCACCAGCAACCTGGCATCTGGGGTGCCAGTCAGATTCTCTGGCTCTGGATCTGGCACCA
GCTACAGCCTGACCATCAGCAGAGTGGAAGCTGAGGATGCTGCCACCTACTACTGCCAGCAGTGGACCAGCAATCCCCCCACCTTTGGAGGGGGCACCAAGCT
GGAAATCAAGAGAACAGTGGCTGCCCCCTCTGTGTTCATCTTCCCACCCTCTGATGAGCAGCTGAAGTCTGGAACAGCCTCTGTTGTGTGCCTGCTGAACAACTT
CTACCCCAGAGAAGCCAAGGTGCAGTGGAAGGTGGACAATGCCCTGCAGTCTGGCAACTCCCAGGAATCTGTGACAGAGCAGGACAGCAAGGACTCCACCTAC

FIG. 43 (cont.)

TCCCTGAGCAGCACCCTGACCCTGAGCAAGGCTGACTATGAGAAGCACAAAGTGTATGCCTGTGAAGTGACCCACCAGGGCCTGTCCAGCCCTGTGACCAAGA
GCTTCAACAGAGGGGAGAGCTGAAGATCTACTTCTGGCTAATAAAAGATCAGAGCTCTAGTGATCTGTGTGTTGGTTTTTTGTGTCTGCATTCTAGCAGTCAAT
ATGTTCACCCCAAAAAAGCTGTTTGTTAACTTGTCAACCTCATTCTAAAATGTATATAGAAGCCCAAAAGACAATAACAAAAATATTCTTGTAGAAC
AAAATGGGAAAGAATGTTCCACTAAATATCAAGATTTAGAGCAAAGCATGAGATGTGTGGGGATAGACAGTGAGGCTGATAAAATAGAGTAGAGCTC
AGAAACAGACCCATTGATATATGTAAGTGACCTATGAAAAAAATATGGCATTTTACAATGGGAAAATGATGGTCTTTTTCTTTTTTAGAAAAACAGG
GAAATATATTTATATGTAAAAAATAAAAGGGAACCCATATGTCATACCATACACACAAAAAAATTCCAGTGAATTATAAGTCTAAATGGAGAAGGCA
AAACTTTAAATCTTTTAGAAAATAATATAGAAGCATGCCATCAAGACTTCAGTGTAGAGAAAAATTTCTTATGACTCAAAGTCCTAACCACAAAGAA
AAGATTGTTAATTAGATTGCATGAATATTAAGACTTATTTTTAAAATTAAAAAACCATTAAGAAAAGTCAGGCCATAGAATGACAGAAAATATTTGC
AACACCCCAGTAAAGAGAATTGTAATATGCAGATTATAAAAAGAAGTCTTACAAATCAGTAAAAAATAAAACTAGACAAAAATTTGAACAGATGAAA
GAGAAACTCTAAATAATCATTACACATGAGAAACTCAATCTCAGAAATCAGAGAACTATCATTGCATATACACTAAATTAGAGAAATATTAAAAGGC
TAAGTAACATCTGTGGCTCTAGCTCTAGTGATCAGCAGTTCAACCTGTTGATAGTATGTACTAAGCTCTCATGTTTAATGTACTAAGCTCTCATGTTTAATGAAC
TAAACCCTCATGGCTAATGTACTAAGCTCTCATGGCTAATGTACTAAGCTCTCATGTTTCATGTACTAAGCTCTCATGTTTGAACAATAAAATTAATATAAATCAGC
AACTTAAATAGCCTCTAAGGTTTTAAGTTTTATAAGAAAAAAAAGAATATATAAGGCTTTTAAAGGTTTTAAGGTTTCCTAGGTTATCCTCATATGAGCTCTTAGA
AAAACTCATCCAGCATCAAATGAAACTGCAATTTATTCATATCAGGATTATCAATACCATATTTTTGAAAAAGTCTTTTCTGTAATGAAGGAGAAAACTCACCCAG
GCAGTTCCATAGGATGGCAAGATCCTGGTATCTGTCTGCAATTCCAACTCTTCCAACATCAATACAACCTATTAATTTCCCCTCATCAAAAATAAGGTTATCAAGT
GAGAAATCACCATGAGTGACCACTGAATCTGGTGAGAATGGCAAAAGATTATGCATTTCTTTCCAGACTTGTTCAACAGGCCAGCCATTTCTCTCATCATCAAAA
TCACTGGCATCAACCAAACCATTATTCATTCTTGATTGGGCCTGAGCCAGTCTAAATACTCTATCAGAGTTAAAAGGACAATTACAAACAGGAATGGAATGCAAT
CTTCTCAGGAACACTGCCAGGGCATCAACAATATTTTCACCTGAATCAGGATATTCTTCCAATACCTGGAATGCTGTTTTCCCTGGGATGGCAGTGGTGAGTAAC
CATGCATCATCAGGAGTTCTGATAAAATGCTTGATGGTTGGAAGAGGCATAAATTCAGTCAGCCAGTTTAGTCTGACCATCTCATCTGTAACATCATTGGCAACA
GAACCTTTGCCATGTTTCAGAAACAACTCTGGGGCATCTGGCTTCCCATACAATCTATAGATTGTGGCACCTGATTGCCCAACATTATCTCTAGCCCATTTATACCC
ATATAAATCAGCATCCATGTTGGAATTTAATCTTGGCCTGGAGCAAGAGGTTTCTCTTTGAATATGGCTCATACATGTGCACCTCCTATAGTGAGTTGTATTATAC
TATGCAGATATACTATGCCAATGTTTAATTGTCAG

FIG. 44

Codon Optimized human FIX (SEQ ID NO:10)

4 : ΔmCMV-EF1-I126- BstEII - ΔhFIX (opt) - BglII -polyA- BV2 (3492 bp)

CACTATGTGGACATGAATTCAATTGGCTAGCAGGAGTCAATGGGAAAAACCCATTGGAGCCAAGTACACTGACTCAATAGGGACTTTCCATT
GGGTTTTGCCCAGTACATAAGGTCAATAGGGGGTGAGTCAACAGGAAAGTCCCATTGGAGCCAAGTACATTGAGTCAATAGGGACTTTCCAA
TGGGTTTTGCCCAGTACATAAGGTCAATGGGAGGTAAGCCAATGGGTTTTTCCCATTACTGACATGTATACTGAGTCATTAGGGACTTTCCAA
TGGGTTTTGCCCAGTACATAAGGTCAATAGGGGTGAATCAACAGGAAAGTCCCATTGGAGCCAAGTACACTGAGTCAATAGGGACTTTCCAT
TGGGTTTTGCCCAGTACAAAAGGTCAATAGGGGGTGAGTCAATGGGTTTTTCCCATTATTGGCACATACATAAGGTCAATAGGGGTGACTAG
TGGAGAAGAGCATGCTTGAGGGCTGAGTGCCCCTCAGTGGGCAGAGAGCACATGGCCCACAGTCCCTGAGAAGTTGGGGGGAGGGGTGG
GCAATTGAACTGGTGCCTAGAGAAGGTGGGGCTTGGGTAAACTGGGAAAGTGATGTGGTGTACTGGCTCCACCTTTTTCCCCAGGGTGGGG
GAGAACCATATATAAGTGCAGTAGTCTCTGTGAACATTCAAGCTTCTGCCTTCTCCCTCCTGTGAGTTTGgtaagtcactgactgtctatgcctgggaaag
ggtgggcaggagatggggcagtgcaggaaaagtggcactatgaacccTGCAGCCCTAGAcaattgtactaaccttcttctctttcctctcctgacagGTTGGTAACCAAGCC
ACCATGCAGAGAGTGAATATGATCATGGCTGAGAGCCCTGGCCTGATCACCATCTGCCTGCTGGGCTACCTGCTGTCTGCTGAGTGCACAGT
GTTTCTGGACCATGAGAATGCCAACAAGATCCTGAACAGGCCCAAGAGGTACAACTCTGGCAAGCTGGAAGAGTTTGTGCAGGGCAACCTG
GAAAGGGAATGCATGGAAGAGAAGTGCAGCTTTGAAGAGGCCAGGGAAGTGTTTGAGAACACAGAGAGAACCACAGAGTTCTGGAAGCA
GTATGTGGATGGGGACCAGTGTGAAAGCAACCCCTGCCTGAATGGGGGCAGCTGCAAGGATGACATCAACAGCTATGAGTGCTGGTGCCCC
TTTGGCTTTGAGGGCAAGAACTGTGAACTGGATGTGACCTGCAACATCAAGAATGGCAGATGTGAACAGTTCTGCAAGAACTCTGCTGACAA
CAAGGTTGTGTGCTCCTGCACAGAGGGCTACAGACTGGCTGAGAACCAGAAAAGCTGTGAACCTGCTGTGCCCTTCCCATGTGGCAGAGTGT
CTGTGTCCCAGACCAGCAAGCTGACCAGAGCTGAGACAGTGTTCCCTGATGTGGACTATGTGAACTCCACAGAGGCTGAAACCATCCTGGAC
AACATCACCCAGAGCACCCAGTCCTTCAATGACTTCACCAGAGTTGTGGGAGGGGAGGATGCCAAGCCTGGCCAGTTCCCATGGCAAGTGGT
GCTGAATGGCAAAGTGGATGCCTTCTGTGGGGGCTCCATTGTGAATGAGAAGTGGATTGTGACAGCTGCCCACTGTGTGGAAACTGGAGTG
AAGATCACAGTGGTGGCTGGGGAGCACAACATTGAGGAAACAGAGCACACAGAGCAGAAAAGAAATGTGATCAGGATCATCCCCCACCACA
ACTACAATGCTGCCATCAACAAGTACAACCATGACATTGCCCTGCTGGAACTGGATGAGCCCCTGGTGCTGAACAGCTATGTGACCCCCATCT
GCATTGCTGACAAAGAGTACACCAACATCTTTCTGAAGTTTGGCTCTGGCTATGTGTCTGGCTGGGGCAGGGTGTTCCACAAGGGAAGGAGT
GCTCTGGTGCTGCAGTACCTGAGAGTGCCACTGGTGGACAGAGCCACCTGTCTGAGAAGCACCAAGTTCACCATCTACAACAACATGTTCTGT
GCTGGCTTCCATGAGGGGGGCAGAGACTCCTGCCAGGGGGATTCTGGGGGCCCTCATGTGACAGAGGTGGAAGGCACCAGCTTTCTGACAG
GCATCATCAGCTGGGGAGAGGAATGTGCCATGAAGGGCAAATATGGCATCTACACCAAGGTGTCCAGATATGTGAATTGGATCAAAGAAAA
GACCAAGCTGACATGAAGATCTACTTCTGGCTAATAAAAGATCAGAGCTCTAGTGATCTGTGTGTTGGTTTTTTGTGTCTGCATTCTAGCTCTA
GTGATCAGCAGTTCAACCTGTTGATAGTATGTACTAAGCTCTCATGTTTAATGTACTAAGCTCTCATGTTTAATGAACTAAACCCTCATGGCTA
ATGTACTAAGCTCTCATGGCTAATGTACTAAGCTCTCATGTTTCATGTACTAAGCTCTCATGTTTGAACAATAAAATTAATATAAATCAGCAACT
TAAATAGCCTCTAAGGTTTTAAGTTTTATAAGAAAAAAAAGAATATATAAGGCTTTTAAAGGTTTTAAGGTTTCCTAGGTTATCCTCATATGAG
CTCTTAGAAAAACTCATCCAGCATCAAATGAAACTGCAATTTATTCATATCAGGATTATCAATACCATATTTTTGAAAAAGTCTTTTCTGTAATG
AAGGAGAAAACTCACCCAGGCAGTTCCATAGGATGGCAAGATCCTGGTATCTGTCTGCAATTCCAACTCTTCCAACATCAATACAACCTATTA
ATTTCCCCTCATCAAAAATAAGGTTATCAAGTGAGAAATCACCATGAGTGACCACTGAATCTGGTGAGAATGGCAAAAGATTATGCATTTCTT
TCCAGACTTGTTCAACAGGCCAGCCATTTCTCTCATCATCAAAATCACTGGCATCAACCAAACCATTATTCATTCTTGATTGGGCCTGAGCCAGT
CTAAATACTCTATCAGAGTTAAAAGGACAATTACAAACAGGAATGGAATGCAATCTTCTCAGGAACACTGCCAGGGCATCAACAATATTTTCA
CCTGAATCAGGATATTCTTCCAATACCTGGAATGCTGTTTTCCCTGGGATGGCAGTGGTGAGTAACCATGCATCATCAGGAGTTCTGATAAAA
TGCTTGATGGTTGGAAGAGGCATAAATTCAGTCAGCCAGTTTAGTCTGACCATCTCATCTGTAACATCATTGGCAACAGAACCTTTGCCATGTT
TCAGAAACAACTCTGGGGCATCTGGCTTCCCATACAATCTATAGATTGTGGCACCTGATTGCCCAACATTATCTCTAGCCCATTTATACCCATAT
AAATCAGCATCCATGTTGGAATTTAATCTTGGCCTGGAGCAAGAGGTTTCTCTTTGAATATGGCTCATACATGTGCACCTCCTATAGTGAGTTG
TATTATACTATGCAGATATACTATGCCAATGTTTAATTGTCAG

SYSTEMS AND METHODS FOR NUCLEIC ACID EXPRESSION IN VIVO

The present application is a continuation of U.S. patent application Ser. No. 16/140,086, filed Sep. 24, 2018, which is a divisional of U.S. patent application Ser. No. 15/268,000, filed Sep. 16, 2016, now U.S. Pat. No. 10,086,089, which claims priority to U.S. Provisional Application Ser. No. 62/220,646 filed Sep. 18, 2015, each of which is herein incorporated by reference.

FIELD OF THE INVENTION

The present invention provides compositions, systems, kits, and methods for expression of one or more proteins or biologically active nucleic acid molecules in a subject, human or non-human mammal, (e.g., at therapeutic levels for the extended periods of time required to produce therapeutic effects). In certain embodiments, systems and kits are provided that comprise a first composition comprising polycationic structures (e.g., empty cationic liposomes, cationic micelles, cationic emulsions, or cationic polymers) and a second composition comprising expression vectors (e.g., non-viral expression vectors not associated with liposomes or other carriers) that are CpG-free or CpG-reduced, that comprise a first nucleic acid sequence encoding: i) a first therapeutic protein or proteins, and/or ii) a first biologically active nucleic acid molecule or molecules. In other embodiments, such first and second compositions are sequentially administered (e.g., systemically) to a subject such that the therapeutic protein and/or the biologically active nucleic acid molecule is/are expressed in the subject (e.g., at a therapeutic level, for at least 5 or at least 50 days, such that a disease or condition is treated or a physiological or disease trait is altered).

BACKGROUND

The simplest non-viral gene delivery system uses naked expression vector DNA. Direct injection of free DNA into certain tissues, particularly muscle, has been shown to produce high levels of gene expression, and the simplicity of this approach has led to its adoption in a number of clinical protocols. In particular, this approach has been applied to the gene therapy of cancer where the DNA can be injected either directly into the tumor or can be injected into muscle cells in order to express tumor antigens that might function as a cancer vaccine.

Although direct injection of plasmid DNA has been shown to lead to gene expression, the overall level of expression is much lower than with either viral or liposomal vectors. Naked DNA is also generally thought to be unsuitable for systemic administration due to the presence of serum nucleases. As a result, direct injection of plasmid DNA appears to be limited to only a few applications involving tissues that are easily accessible to direct injection such as skin and muscle cells.

SUMMARY OF THE INVENTION

The present invention provides compositions, systems, kits, and methods for expression of a protein or proteins and/or biologically active nucleic acid molecule(s) in a subject (e.g., at therapeutic levels for the extended periods of time required to produce therapeutic effects in the host). In certain embodiments, systems and kits are provided that comprise a first composition comprising a first amount of polycationic structures (e.g., empty cationic liposomes, empty cationic micelles, or empty cationic emulsions), and a second composition comprising a therapeutically effective amount of expression vector(s) (e.g., non-viral expression vectors not associated with liposomes) that are CpG-free or CpG-reduced, where the expression vectors comprise a first nucleic acid sequence encoding: i) a first therapeutic protein (or non-therapeutic protein, such as a marker protein), and/or ii) a first biologically active nucleic acid molecule. In certain embodiments, the expression vector comprises a second, third, or fourth nucleic acid sequence encoding a second, third, and/or fourth therapeutic or non-therapeutic protein, and/or a second, third, or fourth biologically active nucleic acid molecule. In some embodiments, the first nucleic acid sequences further encode a second, third, fourth, fifth, and/or sixth therapeutic protein, and/or a second, third, fourth, fifth, and/or sixth biologically active nucleic acid molecule. In other embodiments, such first and second compositions are sequentially administered (e.g., systemically) to a subject such that the therapeutic protein(s) and/or the biologically active nucleic acid molecule(s) is/are expressed in the subject (e.g., at a therapeutic level, for at least 5 or at least 50 days, or at least 100 . . . 200 . . . or at least 400 days, such that disease(s) or condition(s) is/are treated or physiological trait(s) is/are altered).

In some embodiments, provided herein are methods of expressing a first therapeutic protein and/or a biologically active nucleic acid molecule in a subject (e.g., human or non-human mammal) comprising: a) administering (e.g., systemically) a first composition to a subject, wherein the first composition comprises first amount of polycationic structures (e.g., empty cationic liposomes, empty cationic micelles, or empty cationic emulsions) and wherein the first composition is free, or essentially free, of nucleic acid molecules (e.g., nucleic acid is un-detectable or barely detectable in the composition); and b) administering (e.g., systemically, intravascularly, etc.) a second composition to the subject (e.g., initiating within about 2 . . . 10 . . . 50 . . . 100 . . . 200 . . . 300 . . . 400 minutes of administering the first composition), wherein the second composition comprises an amount of expression vectors (e.g., non-viral expression vectors not associated with liposomes or any other carrier), wherein the expression vectors are CpG-free or CpG-reduced, wherein each of the expression vectors comprise nucleic acid sequence(s) encoding: i) first, second, third, fourth, fifth, and/or sixth therapeutic protein(s) or non-therapeutic, and/or ii) first, second, third, fourth, fifth, and/or sixth biologically active nucleic acid molecule(s). In certain embodiments, as a result of the administering the first composition and the administering the second composition, the first therapeutic or non-therapeutic protein and/or the biologically active nucleic acid molecule is/are expressed in the subject (e.g., at a therapeutic level, for at least 5 . . . 50 . . . 100 . . . 300 days . . . 400 days or longer, with respect to a disease or condition, or at an effective level sufficient to alter a physiological or disease trait). In certain embodiments, the polycationic structures (e.g., empty liposomes) present in the first composition have a z-average diameter of about 20-85 nm (e.g., 20 . . . 25 . . . 30 . . . 40 . . . 45 . . . 50 . . . 55 . . . 60 . . . 65 . . . 70 . . . 75 . . . 80 . . . 85 nm). In certain embodiments, the polycationic structures are empty liposomes with a z-average diameter of about 72-76 nm, and are small uni-lammellar vesicles.

In some embodiments, provided herein are methods of expressing a first therapeutic or non-therapeutic protein and/or a biologically active nucleic acid molecule in a subject comprising: a) administering a first composition to a subject, wherein the subject has at least one symptom of a disease or condition, or has at least physiological trait to be altered, wherein the first composition comprises a first amount of polycationic structures (e.g., empty cationic liposomes, empty cationic micelles, or empty cationic emulsions), and wherein the first composition is free, or essentially free, of nucleic acid molecules; and b) administering (or initiating administration of) a second composition to the subject within about 100 minutes or about 200 . . . or 400 minutes of administering said first composition, wherein the second composition comprises a therapeutically effective amount of expression vectors, wherein the expression vectors are CpG-free or CpG-reduced, wherein the expression vectors each comprise a first nucleic acid sequence encoding: i) a first therapeutic or non-therapeutic protein, and/or ii) a first biologically active nucleic acid molecule, c) administering dexamethasone palmitate and/or neutral lipids to the subject, either in said first and/or second composition, or present in a third composition (e.g., within 100 or 200 . . . or 400 minutes of administration of the first or second compositions). In some embodiments, as a result of the administering the first composition, the administering the second composition, and the administering of the dexamethasone palmitate and/or neutral lipids, the first therapeutic protein and/or the biologically active nucleic acid molecule is/are expressed in the subject at a therapeutic level with respect to the disease or condition, or at an effective level sufficient to alter the physiological or disease trait.

In certain embodiments, dexamethasone palmitate is in the first composition, and wherein 2.0% to 6.0% (e.g., 2.0% . . . 2.5% . . . 3.0%) of the first composition comprises the dexamethasone palmitate. In certain embodiments, the dexamethasone palmitate is administered in the third composition, which is administered before the first and/or second composition is administered, or is administered after the first and/or second composition, but within 100 . . . 400 minutes thereof. In certain embodiments, the methods further comprise d) administering dexamethasone to the subject, either in the first and/or second and/or third composition, or present in a fourth composition (e.g., initiating within 100 or 300 minutes of administration of the first or second or third compositions, such as before any of the administrations or after the other administrations). In certain embodiments, the polycationic structures (e.g., empty liposomes) present in the first composition have a z-average diameter of about 20-85 nm (e.g., 20 . . . 25 . . . 30 . . . 40 . . . 45 . . . 50 . . . 55 . . . 60 . . . 65 . . . 70 . . . 75 . . . 80 . . . 85 nm). In certain embodiments, the polycationic structures are empty liposomes with a z-average diameter of about 72-76 nm, and are small uni-lammellar vesicles. In some embodiments, A) the ratio is 10:1 to 18:1; B) 2.0% to 6.0% of the first composition comprises dexamethasone or dexamethasone palmitate; and/or C) each of the expression vectors each comprise only a single expression cassette (i.e., no other expression cassettes are present in each vector), wherein the expression cassette comprises the first nucleic acid sequence encoding the first therapeutic protein and a second nucleic acid sequence encoding a second therapeutic protein, and wherein the expression cassette encodes a self-cleaving peptide sequence (or other cleavage sequence) between the first and second nucleic acid sequences. In certain embodiments, the self-cleaving peptide comprises FMDV 2A. In particular embodiments, the first therapeutic protein comprises a monoclonal antibody light chain and the second therapeutic protein comprises a heavy chain of said monoclonal antibody (e.g., the light and heavy chains combine to form an monoclonal antibody fragment (e.g., Fab) or monoclonal antibody when expresses in a subject). In certain embodiments, the polycationic structures comprise empty liposomes. In particular embodiments, the empty liposomes present in said first composition have an average diameter of about 50-85 nm. In certain embodiments, the methods further comprise administering an agent or additional regulating expression vectors, either in said first and/or second composition, or present in a third composition, wherein the agent increases or decreases the expression at the therapeutic or effective level, and/or the length of time of the expression at said therapeutic or effective level, compared to when the drug agent is not administered to said subject (e.g., for therapeutics that need to be expressed for only a certain, limited amount of time). In particular embodiments, the agent is selected from colchicine, dexamethasone, dexamethasone palmitate, neutral lipids, valproic acid, theophylline, sildenafil, amlexanox, chloroquine, SAHA, and L-arginine+sildenafil.

In some embodiments, the expression vectors each further comprise a regulating nucleic acid sequence, wherein the regulating nucleic acid sequence reduces the duration of expression of the first nucleic acid sequence that would occur in the absence of said regulating nucleic acid sequence. In other embodiments, the regulating nucleic acid sequence is selected from the group consisting of: a promoter, an enhancer, a second nucleic acid sequence encoding a second protein, and/or a second biologically active nucleic acid molecule. In additional embodiments, the first amount of polycationic structures in the first composition comprises a mixture of at least a first and second different types of cationic liposomes that reduces the expression of the first therapeutic protein and/or first biologically active nucleic acid molecule compared to such expression when only said first or only said second type of cationic liposomes are employed in said method. In particular embodiments, the therapeutic protein is expressed at a level that is above 1 ug/ml (e.g., 1.1-1.5 ug/ml), and wherein said therapeutic protein is expressed at the level in said subject for at least 7 consecutive days (e.g., at least 7 . . . 21 . . . 50 . . . 100 . . . or 400 days).

In certain embodiments, provided herein are methods of expressing a first therapeutic protein and/or a biologically active nucleic acid molecule in a subject comprising: a) administering (e.g., systemically) a first composition to a subject, wherein the subject has at least one symptom of a disease or condition, or has at least physiological trait to be altered (e.g., level of hematopoietic stem cells), wherein the first composition comprises a first amount of polycationic structures (e.g., empty cationic liposomes, empty cationic micelles, or empty cationic emulsions), and wherein the first composition is free, or essentially free, of nucleic acid molecules; and b) administering (e.g., systemically) a second composition to the subject be initiated (or completed) within about 2 . . . 10 . . . 25 . . . 100 . . . 200 or 400 minutes of administering the first composition, wherein the second composition comprises a therapeutically effective amount of expression vectors (e.g., plasmid), wherein the expression vectors are CpG-free or CpG-reduced (e.g., the nucleic acid sequence of the expression vector has been altered to contain fewer CpG di-nucleotides than normally present in the wild-type version of the sequences in the vector), wherein the expression vectors each comprise nucleic acid sequence(s) encoding: i) a first therapeutic protein (or first and second therapeutic proteins, or first, second, and third therapeutic proteins, etc.), and/or ii) a first biologically active nucleic acid molecule (or first and second or more biologically active nucleic acid molecules), and wherein, as a result of the administering the first composition and the administering the second composition, and wherein, as a result of administering the first and second compositions, the therapeutic protein(s) and/or the biologically active nucleic acid molecule(s) is/are expressed in the subject at a therapeutic level with respect to the disease or condition, or at an effective level sufficient to alter the physiological or disease trait.

In certain embodiments, the expression vectors are not associated with polycationic structures (e.g., empty cationic liposomes, empty cationic micelles, or empty cationic emulsions)), or other molecules, in the second composition (and there are no detectable polycationic structures present in the second composition). In other embodiments, the expression vectors are naked, non-viral, expression vectors (e.g., plasmids). In certain embodiments, the expression vectors are viral expression vectors (e.g., adeno-associated viral vector or adenovirus vector or synthetic mRNA, miRNA, ribozyme or shRNA nucleic acid vectors). In particular embodiments, the first and/or second composition is administered systemically, regionally, transcutaneously, intradermally, orally, intramuscularly, intravenously, into the gastrointestinal tract, bladder or by pulmonary inhalation, or by an intrathecal or intraventricular route.

In certain embodiments, the therapeutic protein or proteins and/or biologically active nucleic acid molecule or molecules is/are expressed at the therapeutic or effective level in the subject on consecutive days for at least 5 . . . 20 . . . 63 . . . 100 . . . 200 . . . 300 days . . . 1 year or more. In some embodiments, the methods further comprise: c) testing the subject (e.g., body imaging or scanning), or a sample (e.g., blood, serum, plasma, tissue, urine, etc.) from the subject, after at least 5 . . . 20 . . . 63 . . . 100 . . . 200 . . . 300 days . . . or 1 year from the administering the first and second compositions, and determining that the therapeutic protein(s) and/or biologically active nucleic acid molecule(s) is/are being expressed in the subject at the therapeutic or effective level (e.g., therapeutic levels have been sustained in the subject for a time period required to produce therapeutic effects in the subject due the single treatment of the first and second compositions). In additional embodiments, the methods further comprise: d) generating a written and/or electronic report that indicates the therapeutic protein and/or biologically active nucleic acid molecule is/are being expressed in the subject at the therapeutic or effective level (e.g., for a certain amount of time). In other embodiments, the report is sent to the treating clinician or practitioner and/or patient from a lab that conducted the test.

In some embodiments, the therapeutic protein and/or biologically active nucleic acid molecule is/are expressed at a level of at least 50 pg/ml . . . 100 . . . 500 . . . 1000 . . . 1500 . . . 4000 . . . 8000 . . . 9500 . . . 1,000,000 pg/ml (1 ug/ml) . . . 1.5 ug/ml or higher, and wherein a blood, serum, or plasma sample (or other biological sample) from the subject is assayed to determine that the therapeutic or effective level is achieved for at least 5 . . . 7 . . . 10 . . . 25 . . . 45 . . . 63 . . . 150 . . . 300 days, or longer, after the administration of the first and second compositions. In other embodiments, the therapeutic protein(s) is/are expressed at a level that is at least 50 pg/ml or at least 100 pg/ml or at least 500, 1,000,000 pg/ml (1 ug/ml) . . . 1.5 ug/ml or higher, and wherein the therapeutic protein is expressed at the level in the subject for at least 5 . . . 7 . . . 10 . . . 25 . . . 45 . . . 63 . . . 150 . . . 300 . . . 350 consecutive days. In certain embodiments, the therapeutic protein and/or biologically active nucleic acid molecule is expressed (e.g., at therapeutic levels) in the subject without clinically significant elevated toxicity (e.g., as measured by ALT (alanine aminotransferase) and/or AST (aspartate aminotransferase)) after at least 48 hours following the administration of the first and second compositions.

In certain embodiments, the therapeutic protein is human G-CSF (e.g., as encoded by SEQ ID NO:1, or sequence with at least 98% identity with SEQ ID NO:1) and is expressed in the subject at a therapeutic level of at least 100 pg/ml as measured in a blood, serum, or plasma sample, wherein the therapeutic protein is expressed in the subject for at least seven days, and wherein the disease, condition, or physiological trait is selected from the group consisting of: neutropenia caused by chemotherapy, non-elevated levels of hematopoietic stem cells in blood of a stem cell donor or recipient, heart degeneration, cerebral ischemia, amyotrophic lateral sclerosis, neutrophil deficiency diseases, and radiation exposure. In particular embodiments, the G-CSF is expressed for at least 5, or 6, or 7 days, but no more than about 10 days (e.g., using drugs, promoter/enhancer combinations, additional expression cassette within the nucleic acid vector or additional expressed proteins to limit production to about 10 days to avoid any toxic neutrophilia-related side effects by expression beyond about 10 days). In other embodiments, the therapeutic protein is Rituximab or similar anti-CD20 antibody or antibody fragment. In some embodiments, the therapeutic protein is human Factor IX or similar protein.

In particular embodiments, the therapeutic protein or proteins and/or biologically active nucleic acid molecule or molecules is/are expressed in the subject for a sufficient amount of time at the therapeutic level to reduce or eliminate the at least one symptom (or all symptoms) without the subject having to receive any other treatment that provides the therapeutic protein(s) and/or biologically active nucleic acid molecule(s) to the subject. In further embodiments, during the sufficient time, the subject does not receive any other specific treatment (e.g., no other specific therapeutic treatment that provides the therapeutic protein or biologically active nucleic acid molecule(s) to the subject). In certain embodiments, the subject has multiple symptoms of a disease or diseases, and wherein the sufficient amount of time is such that all or substantially all of the multiple symptoms of the disease(s) and/or the condition(s) are reduced or eliminated in the subject (e.g., permanently, or for at least 20 days . . . 50 days . . . 200 days . . . 1 year or longer). In other embodiments, during the sufficient time, the subject does not receive the any other disease-specific treatment.

In some embodiments, the first amount of the polycationic structures (e.g., empty cationic liposomes, empty cationic micelles, or empty cationic emulsions) is about 0.01-70, 30-50, or 20-60, μmoles per 1 kilogram of the subject (e.g., 0.01 . . . 1 . . . 10 . . . 20 . . . 40 . . . or 60 μmoles per kilogram). In other embodiments, the ratio of the first amount of the polycationic structures (e.g., empty cationic lipids) to the therapeutically effective amount of the expression vectors is 0.5:1 to 25:1, nmoles of polycationic structures (e.g., empty cationic lipids) to 1 μg of expression vectors (e.g., 0.5:1 . . . 1:1 . . . 4:1 . . . 8:1 . . . 12:1 . . . 17:1 . . . 21:1 . . . or 25:1). In certain embodiments, the ratio of the first amount of the polycationic structures (e.g., empty cationic lipids) to the therapeutically effective amount of the expression vectors is 7:1 to 13:1, nmoles of polycationic structures (e.g., empty cationic lipids) to 1 μg of expression vectors. In particular embodiments, the therapeutically effective amount of the expression vectors is 0.001-8.0 milligrams of the expression vectors per 1 kilogram of the subject (e.g., 0.001 . . . 0.1 . . . 3.0 . . . 4.5 . . . 5.7 . . . 7.1 . . . 8.0 milligrams per kilogram). In some embodiments, the therapeutically effective amount of expression vectors is 0.001 to 1 μg per 1 kilogram of the subject (e.g., 0.001 . . . 0.01 . . . 0.1 . . . 1 μg per kilogram of subject). In certain embodiments, the therapeutically effective amount of the expression vectors is about 0.01-4.0 milligrams of the expression vectors per 1 kilogram of the subject.

In some embodiments, the first nucleic acid sequence encodes the first or first and second, or first, second, and third, therapeutic protein(s). In additional embodiments, the first nucleic acid sequence encodes the biologically active nucleic acid molecule(s). In other embodiments, the subject is a human. In additional embodiments, the expression vectors are CpG-free. In other embodiments, the expression vectors are CpG-reduced. In other embodiments, the therapeutic protein(s) is/are human protein(s) or animal protein(s).

In some embodiments, the polycationic structures do not contain cholesterol (e.g., cholesterol free empty cationic micelles or liposomes). In certain embodiments, the cationic liposomes each comprise at least 60% DOTAP and/or DPTAP (e.g., 60% . . . 75% . . . 85% . . . 95% . . . 98% . . . 100% DOTAP and/or DPTAP). In other embodiments, all or substantially all of the cationic liposomes are multi-lamellar vesicles. In further embodiments, all or substantially all of the cationic liposomes are uni-lamellar vesicles. In further embodiments, the cationic liposomes each comprise at least 99% DOTAP or 99% DPTAP. In further embodiments, the empty cationic liposomes each comprise DOTAP and cholesterol. In additional embodiments, the cationic liposomes each comprise about one-third cholesterol and about two-thirds DOTAP and/or DPTAP. In further embodiments, the first nucleic acid sequence encodes human G-CSF (e.g., as shown in SEQ ID NO:1).

In certain embodiments, the biologically active nucleic acid molecule(s) comprises sequence(s) selected from: shRNA sequence(s), miRNA sequence(s), antisense sequence(s), ribozyme(s), and/or CRISPR single guide RNA sequence(s) (sgRNA). In other embodiments, the CRISPR sgRNA comprises: i) a Cas9 nuclease-recruiting sequence (tracRNA), and ii) a target-specific sequence (crRNA) that hybridizes to a sgRNA target site. In particular embodiments, the biologically active nucleic acid molecule targets human p65 (aka, NF-kappa-B p65 or RELA).

In further embodiments, each of the expression vectors further comprises a second nucleic acid sequence encoding: i) a second therapeutic protein, and/or ii) a second biologically active nucleic acid molecule. In some embodiments, each of the expression vectors further comprises a third nucleic acid sequence encoding: i) a third, and/or fourth therapeutic protein, and/or ii) a third, and/or fourth biologically active nucleic acid molecule. In further embodiments, each of the expression vectors further comprise a first promoter associated with the first nucleic acid sequence, and a second promoter associated with the second nucleic acid sequence, and wherein the first and second promoters are the same or different. In other embodiments, the therapeutic or effective expression level of the first nucleic acid sequence and/or the length of time of the therapeutic or effective expression level, is reduced compared to the expression level or the length of time, when the second nucleic acid is not present and/or expressed from the expression vectors. In other embodiments, the first nucleic acid sequence is expressed at the therapeutic level for at least 5 days, but less than 21 days (e.g., 5 . . . 7 . . . 13 . . . 16 . . . 20 . . . and 21 days). In certain embodiments, the first nucleic acid sequence encodes the therapeutic protein, and wherein the therapeutic protein comprises human G-CSF.

In other embodiments, the expression vector provides the expression at the therapeutic or effective level for a first length of time and/or at a first level of expression when each of the expression vectors comprises a first promoter and first enhancer associated with the first nucleic acid sequence, and wherein the first length of time and/or expression level is altered when a second promoter, different from the first promoter, replaces the first promoter, and/or a second enhancer, different from the second enhancer, replaces the second promoter, on the expression vectors. In other embodiments, the expression at the therapeutic or effective level for a first length of time is for at least 10 . . . 15 . . . 45 . . . 100 . . . 200 . . . 300 days, and wherein replacement with the second promoter and/or second enhancer reduces expression at the therapeutic or effective level to a second length of time that is less than 10 . . . 15 . . . 45 . . . 100 . . . 200 days. In other embodiments, each of the expression vectors comprises a first promoter and a first enhancer, and wherein the first promoter and the first enhancer cause expression at the therapeutic level for at least 5 days, but less than 21 . . . 15 . . . or 10 days. In particular embodiments, the first nucleic acid sequence encodes the therapeutic protein, and wherein the therapeutic protein comprises human G-CSF.

In some embodiments, the methods further comprise administering a drug agent or agents, either in the first and/or second composition, or present in a third composition, wherein the drug agent or agents increase or decrease the expression of the first nucleic acid (e.g., at the therapeutic or effective level, and/or the length of time of the expression at the therapeutic or effective level), compared to when the drug agent or agents are not administered to the subject. In particular embodiments, the drug agent increases the expression level of the first nucleic acid in the subject, and wherein the drug is selected from colchicine, an immunosuppressant, dexamethasone, dexamethasone palmitate, sildenafil, or L-arginine +sildenafil. In certain embodiments, the drug (e.g., dexamethasone or dexamethasone palmitate) is present at between 2.0% and 6.0% of a polycationic structure (e.g., empty cationic lipid composition), such as at 2.0% . . . 2.5% . . . 3.5% . . . 4.5% or 6.0%. In other embodiments, the drug (e.g., dexamethasone or dexamethasone palmitate), is administered to the subject before or after the polycationic structure and vector compositions are administered. In certain embodiments, the polycationic structures (e.g., empty liposomes) present in the first composition have a z-average diameter of about 20-85 nm (e.g., 20 . . . 25 . . . 30 . . . 40 . . . 45 . . . 50 . . . 55 . . . 60 . . . 65 . . . 70 . . . 75 . . . 80 . . . 85 nm). In certain embodiments, the polycationic structures are empty liposomes with a z-average diameter of about 72-76 nm, and are small uni-lammellar vesicles.

In other embodiments, the therapeutic protein is expressed at a level of at least two times higher (or at least 3 or 4 or 5 times higher) when the drug agent is administered to the subject compared to when the drug agent is not administered to the subject. In particular embodiments, the drug agent decreases the expression level of the first nucleic acid sequence, and wherein the drug agent is L-arginine. In further embodiments, the therapeutic protein is expressed at a level of at least two times (or at least three times or four times) lower when the drug agent is administered to the subject compared to when the drug agent is not administered to the subject.

In some embodiments, the drug agent comprises an anti-inflammatory agent. In additional embodiments, the drug agent is selected from the group consisting of: amlexanox, chloroquine, valproic acid, theophylline, DHA, prostaglandin, and SAHA.

In further embodiments, the expression vectors are free of operable matrix attachment region (MAR) sequences. In certain embodiments, the expression vectors are free of operable EBNA-1 and/or EBV viral sequences. In certain embodiments the subject's blood pressure, immediately prior to said administering said first and second compositions, is not altered (e.g., no physical transfection aids are applied to the subject to attempt to increase expression of the first nucleic acid sequence).

In particular embodiments, the therapeutic level and/or effective level is at least 150 . . . 100 . . . 500 . . . 1000 . . . 1500 . . . 5000 . . . 1,000,000 pg/ml (1 ug/ml) . . . 1.5 ug/ml or higher, and wherein a blood, serum, or plasma sample (or other biological sample) from the subject is determined to be at the therapeutic level and/or effective level at least 7 . . . 10 . . . 25 . . . 45 . . . 63 . . . 150 . . . 300 . . . 400 days or more after the administration of the first and second compositions. In particular embodiments, the sample from the subject is tested with an ELISA assay or by mass spectrometry to determine the expression level.

In some embodiments, the methods further comprise administering a therapeutically effective amount of neutral liposomes to the subject, wherein the neutral liposomes are present in the first and/or second composition, and/are administered in a third composition, and wherein the therapeutically effective amount of neutral liposomes are administered to the subject prior to the administering the second composition. In certain embodiments, the neutral liposomes comprise at least material selected from: phospholipon 90H, hydrogenated soy PC, stearic and palmitic. In other embodiments, the therapeutically effective amount of neutral liposomes are present in the first composition or present in a third composition administered to the subject. In further embodiments, the neutral liposomes are multilamellar vesicles or extruded to 0.2 or 0.1 um. In particular embodiments, administering the therapeutically effective amount of the neutral liposomes causes expression of the first therapeutic protein and/or the biologically active nucleic acid molecule in the subject that is at least 3 . . . 4 . . . 25 . . . 100 . . . 350 . . . or 600 times higher than occurs when the neutral liposomes are not administered to the subject. In certain embodiments, the ratio of empty cationic liposomes to the neutral liposomes administered to the subject is between about 2:1 and 1:5 (e.g., 2:1 . . . 1:1 . . . 2:5 . . . 1:5).

In some embodiments, provided herein are methods of expressing a first therapeutic protein and/or a biologically active nucleic acid molecule in a subject comprising: a) administering a first composition to a subject, wherein the first composition comprises an anti-inflammatory agent; and b) administering or initiating administration of, a second composition to the subject within about 2 minutes . . . 20 minutes . . . 1 hour . . . 24 hours . . . 5 days . . . 7 days . . . 9 days or more of administering the first composition, wherein the second composition comprises a therapeutically effective amount of polyplexes, wherein each polyplex comprises an expression vector and polyethylenimine, wherein the expression vector is CpG-free or CpG-reduced, wherein each expression vector comprises a first nucleic acid sequence encoding: i) a first therapeutic protein (and/or first and second proteins), and/or ii) a first (and/or first and second) biologically active nucleic acid molecule, and wherein, as a result of administering the first composition and administering the second composition, the first therapeutic protein and/or the biologically active nucleic acid molecule is/are expressed in the subject. In further embodiments, the subject has at least one symptom of a disease or condition, or has at least one physiological trait desired to be altered, and wherein the first therapeutic protein and/or the biologically active nucleic acid molecule is expressed at a therapeutic level with respect to the disease, condition, or physiological trait to be altered. In some embodiments, the anti-inflammatory agent is selected from the group consisting of amlexanox, chloroquine, and suberanilohydroxamic acid (SAHA).

In some embodiments, the expression vector comprises a plasmid or other non-viral vector. In further certain embodiments, the administration in step b) is accomplished by systemically administering the second composition.

In some embodiments, provided herein are systems or kits comprising: a) a first composition comprising a first amount of polycationic structures (e.g., empty cationic liposomes, empty cationic micelles, or empty cationic emulsions), wherein the first composition is free, or essentially free, of nucleic acid molecules; and b) a second composition comprises a therapeutically effective amount of expression vectors (e.g., non-viral and not associated with liposomes or other carrier molecules), wherein the expression vectors are CpG-free or CpG-reduced, wherein each of the expression vectors comprises a first nucleic acid sequence encoding: i) a first therapeutic protein or non-therapeutic protein, and/or ii) a first biologically active nucleic acid molecule. In other embodiments, the expression vectors are a naked, non-viral expression vectors (e.g., plasmid). In certain embodiments, at least one of the following applies: i) wherein the ratio of the first amount of the polycationic structure (e.g., empty cationic liposome) to the therapeutically effective amount of expression vectors is 2:1 to 25:1 or 5:1 to 25:1; ii) wherein 2.0% to 6.0% of the first composition comprises dexamethasone palmitate; iii) wherein the first composition further comprises neutral lipid, and iv) wherein the polycationic structures comprise empty liposomes, and wherein the empty liposomes present in the first composition have a z-average diameter of about 20-85 nm (e.g., 20 . . . 25 . . . 30 . . . 40 . . . 45 . . . 50 . . . 55 . . . 60 . . . 65 . . . 70 . . . 75 . . . 80 . . . 85 nm). In certain embodiments, the vectors are viral vectors (e.g., AAV or adeno viral vectors). In particular embodiments, the therapeutic protein is human G-CSF (e.g., as shown in SEQ ID NO:1).

In particular embodiments, the first amount of the polycationic structure (e.g., empty cationic liposomes) is between 0.1 to 7.0 millimoles (e.g., 0.1 . . . 5.0 . . . 7.0 millimoles) or 1.5 and 5.0 millimoles (e.g., suitable amount for administration to a human subject). In other embodiments, the ratio of the first amount of the polycationic structure (e.g., empty cationic liposome) to the therapeutically effective amount of the expression vectors is 0.5:1 to 25:1, nmoles of empty cationic lipid to 1 μg of expression vectors (e.g., 0.5:1 . . . 1:1 . . . 5:1 . . . 10:1 . . . 15:1 . . . 25:1). In some embodiments, the ratio of the first amount of the polycationic structure (e.g., empty cationic lipid) to the therapeutically effective amount of the expression vectors is 7:1 to 13:1, nmoles of polycationic structure to 1 μg of expression vectors (e.g., 7:1 . . . 10:1 . . . or 13:1). In other embodiments, the therapeutically effective amount of the expression vectors is between 0.1 and 800 milligrams (e.g., suitable amount for administration to a human subject, such as when the vector is a plasmid). In certain embodiments, the amount is 1 . . . 25 . . . 400 . . . or 800 milligrams of expression vectors for human administration.

In other embodiments, the first nucleic acid sequence encodes the first therapeutic protein. In additional embodiments, the first nucleic acid sequence encodes the biologically active nucleic acid molecule. In particular embodiments, the expression vectors are CpG-free. In other embodiments, the expression vectors are CpG-reduced. In further embodiments, the first therapeutic protein is a human protein. In other embodiments, the first nucleic acid sequence encodes the therapeutic protein, and wherein the therapeutic protein comprises human G-CSF, Rituximab, a monoclonal antibody or monoclonal antibody fragment (e.g., Fab), or human Factor IX.

In certain embodiments, the empty cationic liposomes, micelles, or emulsions, each comprise at least 60% DOTAP and/or DPTAP (e.g., 60% . . . 75% . . . 85% . . . 95% . . . 98% . . . 100% DOTAP and/or DPTAP), and may be cholesterol-free (e.g., no detectable cholesterol in the composition). In other embodiments, all or substantially all of the empty cationic liposomes, micelles, or emulsions are multilamellar vesicles. In further embodiments, all or substantially all of the empty cationic liposomes, micelles, or emulsions are either unilamellar, multilamellar, or oligolamellar vesicles. In further embodiments, the empty cationic liposomes, micelle, or emulsions each comprise at least 99% DOTAP or at least 99% DPTAP, and may be cholesterol free. In further embodiments, the empty cationic liposomes each comprise DOTAP and/or DPTAP and cholesterol. In additional embodiments, the empty cationic liposomes, micelles, or emulsions each comprise about one-third cholesterol and about two-thirds DOTAP and/or DPTAP.

In certain embodiments, the first biologically active nucleic acid molecule comprises a sequence selected from: an siRNA or shRNA sequence, a miRNA sequence, an antisense sequence, and a CRISPR single guide RNA sequence (sgRNA). In other embodiments, the CRISPR sgRNA comprises: i) a Cas9 nuclease-recruiting sequence (tracRNA), and ii) a target-specific sequence (crRNA) that hybridizes to a sgRNA target site.

In further embodiments, each of the expression vectors further comprises a second nucleic acid sequence encoding: i) a second therapeutic protein, and/or ii) a second biologically active nucleic acid molecule. In further embodiments, each of the expression vectors further comprise a first promoter associated with the first nucleic acid sequence, and a second promoter associated with the second nucleic acid sequence, and wherein the first and second promoters are the same or different.

In some embodiments, the kits and systems further comprise a first container and a second container, and wherein the first composition is present in the first container and the second composition is present in the second container. In other embodiments, kits and systems further comprise a packaging component (e.g., cardboard box, plastic pouch, etc.), wherein the first container and the second container are inside the packaging component.

In certain embodiments, the kits and systems further comprise a drug agent or drug agents, wherein the drug agent(s) are present in the first and/or second compositions, or is present in a third composition. In additional embodiments, the drug agent is selected from colchicine, an immunosuppressant, dexamethasone, sildenafil, L-arginine, or L-arginine+sildenafil. In further embodiments, the drug agent comprises an anti-inflammatory agent. In further embodiments, the drug agent is selected from the group consisting of: amlexanox, valproic acid, theophylline, chloroquine, and SAHA.

In particular embodiments, the expression vectors are free of operable matrix attachment region (MAR) sequences. In additional embodiments, the expression vectors are free of operable EBNA-1 and/or EBV viral sequences.

In certain embodiments, the kits and systems further comprise a therapeutically effective amount of neutral liposomes, wherein the neutral liposomes are present in the first and/or second compositions, or is present in a third composition. In additional embodiments, the therapeutically effective amount of neutral liposomes are present in the first composition. In other embodiments, the neutral liposomes are multilamellar or oligo- or uni-lamellar vesicles. In further embodiments, the ratio of empty cationic liposomes or micelles to the neutral liposomes is between about 2:1 and 1:5 (e.g., 2:1 . . . 1:1 . . . 3:5 . . . 1:5).

In some embodiments, provided herein are a first composition and a second, separate, composition for combined use in the treatment of a disease amenable to treatment with in vivo expression of a first therapeutic protein and/or biologically active nucleic acid molecule, wherein the first composition comprises a first amount of polycationic structures (e.g., empty cationic liposomes, empty cationic micelles, or empty cationic emulsions), wherein the first composition is free, or essentially free, of nucleic acid molecules; and b) a second composition that comprises a therapeutically effective amount of expression vectors, wherein the expression vectors are CpG-free or CpG-reduced, wherein each of the expression vectors comprises a first nucleic acid sequence encoding: i) a first therapeutic protein, and/or ii) a first biologically active nucleic acid molecule.

In certain embodiments, provided herein are methods of expressing a first therapeutic protein and/or a biologically active nucleic acid molecule in a subject comprising: a) administering a first composition to a subject, wherein the first composition comprises a first amount of polycationic structures (e.g., empty cationic liposomes, empty cationic micelles, or empty cationic emulsions), and wherein the first composition is free, or essentially free, of nucleic acid molecules; and b) administering a second composition to the subject within about 100 minutes or 200 minutes of administering the first composition, wherein the second composition comprises a therapeutically effective amount of non-viral expression vectors, wherein the expression vectors are CpG-free or CpG-reduced, wherein the expression vectors each comprise a first nucleic acid sequence encoding: i) a first therapeutic protein, and/or ii) a first biologically active nucleic acid molecule, and wherein, as a result of administering the first composition and administering about the second composition, the first therapeutic protein and/or the biologically active nucleic acid molecule is/are expressed in the subject at a level above (e.g., at least 150 . . . 300 . . . 575 . . . 1000 . . . 1500 . . . 2000 . . . 5000 . . . or 1,000,000 pg/ml) (e.g., as measured in a serum sample from the subject (e.g., after 7 . . . 25 . . . 50 days from the first and second administrations).

In certain embodiments, provided herein are methods comprising: administering a composition to a subject comprising a therapeutically effective amount of non-viral expression vectors that are CpG-free or CpG-reduced and comprise a first nucleic acid sequence encoding: i) a first therapeutic protein, and/or ii) a first biologically active nucleic acid molecule, and wherein, as a result of administering the first and second compositions, the first therapeutic protein and/or the biologically active nucleic acid molecule is/are expressed in the subject at a level above 100 pg/ml (e.g., at least 150 . . . 400 . . . 1200 . . . 2000 . . . 5000 . . . or more than 1,000,000 pg/ml) (e.g., as measured in a serum sample from the subject (e.g., after 7 . . . 25 . . . 50 days from the first and second administrations).

In certain embodiments, the polycationic structures comprises empty cationic liposomes, micelles, or emulsions. In other embodiments, the polycationic structures comprises one or more of the following, either alone or combined with polycationic structures: linear or branched polyethyleneimine, dendrimers (e.g., 4th generation pamaam dendrimer based on ethylene diamine, polylysine, polyarginine, and protamine sulfate), poly-lysine, and protamine sulfate. In certain embodiments, the polycationic structures are provided as a cationic emulsion. In particular embodiments, the surfactants in the emulsions are selected from: cetylpyridinium chloride, cetyltrimethylammonium bromide or the like. In other embodiments, the emulsions further comprise a neutral component, such as tweens, spans and triglycerides. In particular embodiments, the emulsions comprises a cationic lipid, such as, for example, DOTAP, DPTAP, DOTMA, or DDAB. In some embodiments, the emulsions are self-emulsifying emulsions or microemulsions (SEDDS, SMEDDS).

In some embodiments, provided herein are methods of expressing a first and second proteins and/or first and second biologically active nucleic acid molecules in a subject comprising: a) administering a first composition to a subject, wherein the subject has at least one symptom of a disease or condition, or has at least physiological trait to be altered, wherein said first composition comprises a first amount of polycationic structures, and wherein said first composition is free, or essentially free, of nucleic acid molecules; and b) administering a second composition to said subject within about 100 minutes of administering the first composition, wherein the second composition comprises a therapeutically effective amount of expression vectors, wherein the expression vectors are non-viral and are CpG-free or CpG-reduced, wherein the expression vectors each comprise: i) a first expression cassette encoding: A) a first protein, and/or B) a first biologically active nucleic acid molecule, and ii) a second expression cassette encoding: A) a second protein and/or B) a second biologically active nucleic acid molecule. In certain embodiments, as a result of the administering the first composition and the administering the second composition, the first and second proteins and/or said first and second biologically active nucleic acid molecule is/are expressed in the subject at a therapeutic level with respect to the disease or condition, or at an effective level sufficient to alter said physiological or disease trait.

In particular embodiments, the first protein comprises a monoclonal antibody light chain, and the second protein comprises a heavy chain of said monoclonal antibody. In other embodiments, the first and second expression cassettes both comprise regulatory elements. In additional embodiments, the regulatory elements are the same or different in said first and second expression cassettes.

DESCRIPTION OF THE FIGURES

FIG. 2 shows the CpG-free modified nucleic sequence of h-GCSF (SEQ ID NO:1) and the amino acid sequence of h-GCSF (SEQ ID NO:2). The positions where CpG dinucleotides have been eliminated are shown in underline in SEQ ID NO:1.

FIG. 36 shows the arrangement of the Rituximab (anti-CD20) dual cassette plasmids used in the Examples. In this figure, the following abbreviations apply: M: Mar (M1:β-Glo, M2:21q21 and M3:IFNβ); K: Kozak Sequence (K1: AAGCTTTCC, SEQ ID NO:3; K2:AAGCCACC, SEQ ID NO:4); Enhancer: mCMV or hCMV; Promoter: CMV or EF1; 5'UTR: I126 or htlv; H: Chimeric Heavy Chain cDNA; L: Chimeric Light Chain cDNA; and pA: polyA

FIG. 38 shows the arrangement of the human Factor IX plasmids used in the Examples.

The following abbreviations apply in this figure: M: Mar (M1: β-Glo, and M3: IFNβ); Kozak2: Kozak Sequence2 (AAGCCACC, SEQ ID NO:4); Enhancer: mCMV; Promoter: EF1; 5'UTR: I126; hFIX: human Factor XI cDNA; and pA: polyA FIG. 39 shows one example (No. 8, G4) of a bicistronic, single cassette plasmid construct (SEQ ID NO:5) used in the Examples below that expresses the heavy and light chains (underlined) of Rituximab.

FIG. 40 shows one example (No. 2) of a dual cassette non-optimized anti-CD20 CpG free plasmid construct (SEQ ID NO:6) used in the Examples below that expresses the heavy and light chains (underlined) of Rituximab.

FIG. 41 shows one example (No. 4) of a dual cassette non-optimized anti-CD20 CpG free plasmid construct (SEQ ID NO:7) used in the Examples below that expresses the heavy and light chains (underlined) of Rituximab.

FIG. 42 shows one example (No. 4) of a dual cassette MAR-less optimized anti-CD20 plasmid construct (SEQ ID NO:8) used in the Examples below that expresses the heavy and light chains (underlined) of Rituximab.

FIG. 43 shows one example (No. 6) of a dual cassette MAR-containing optimized anti-CD20 plasmid construct (SEQ ID NO:9) used in the Examples below that expresses the heavy and light chains (underlined) of Rituximab.

FIG. 44 shows one example (No. 4) of a plasmid construct (SEQ ID NO:10) used in the Examples below that expresses human Factor IX.

DEFINITIONS

Figure 1:
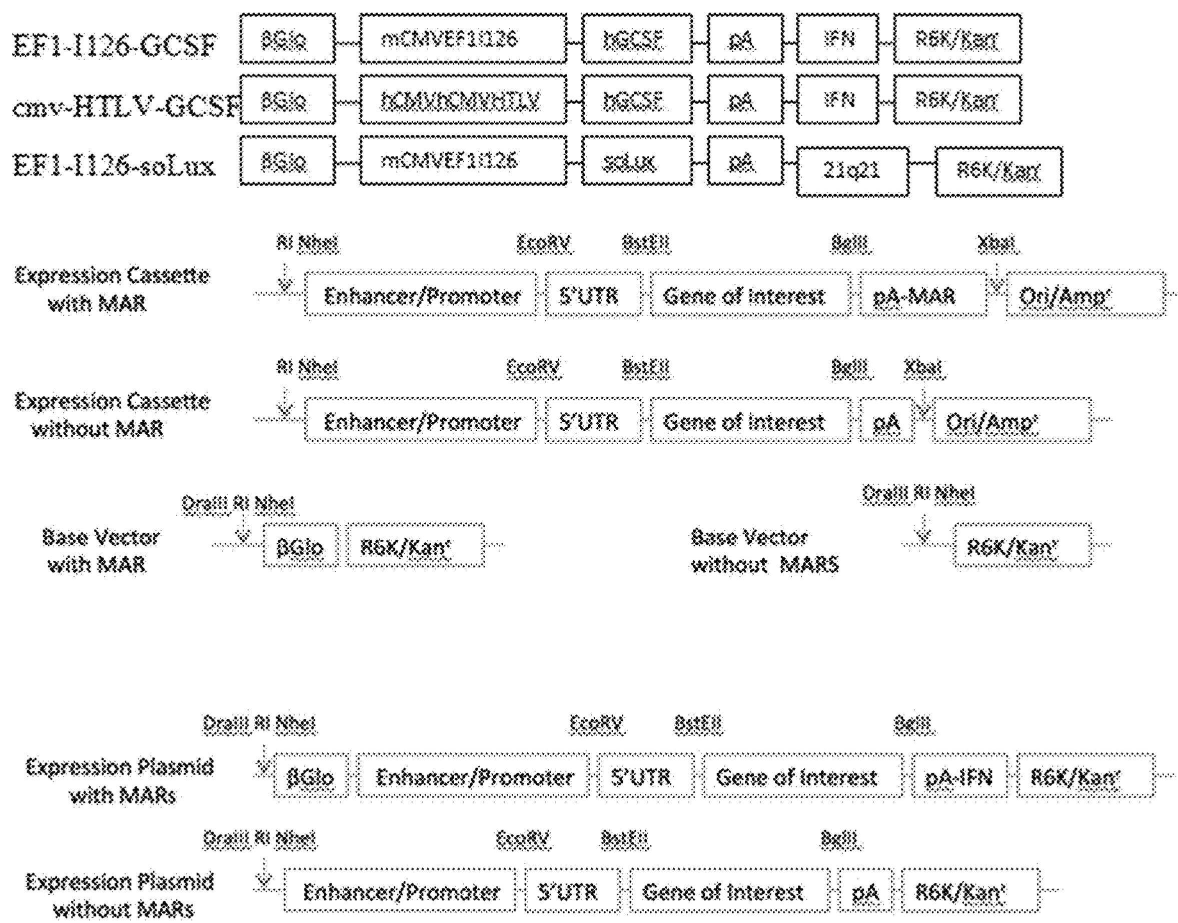
FIG. 1 shows a schematic representation of the various CPG-free plasmid constructs used in Example 1.

As used herein, the phrase "CpG-reduced" refers to a nucleic acid sequence or expression vector that has less CpG di-nucleotides than present in the wild-type versions of the sequence or vector. "CpG-free" means the subject nucleic acid sequence or vector does not have any CpG di-nucleotides. An initial sequence, that contains CpG dinucleotides (e.g., wild-type version of human G-CSF), may be modified to remove CpG dinucleotides by altering the nucleic acid sequence. Such CpG di-nucleotides can be suitably reduced or eliminated not just in a coding sequence, but also in the non-coding sequences, including, e.g., 5' and 3' untranslated regions (UTRs), promoter, enhancer, polyA, ITRs, introns, and any other sequences present in the nucleic acid molecule or vector.

As used herein, "empty liposomes" refers to liposomes that do not contain nucleic acid molecules but that may contain other bioactive molecules (e.g., liposomes that are only composed of the lipid molecules themselves, or only lipid molecules and a small molecule drug).

As used herein, "empty cationic micelles" refers to cationic micelles that do not contain nucleic acid molecules but that may contain other bioactive molecules (e.g., micelles that are only composed of lipid and surfactant molecules themselves, or only lipid and surfactant molecules and a small molecule drug).

As used herein, "empty cationic emulsions" refers to cationic emulsions or micro-emulsions that do not contain nucleic acid molecules but that may contain other bioactive molecules.

DETAILED DESCRIPTION

The present invention provides compositions, systems, kits, and methods for generating expression of a protein or biologically active nucleic acid molecule in a subject (e.g., at therapeutic levels for extended periods of time). In certain embodiments, systems and kits are provided that comprise a first composition comprising a first amount polycationic structures (e.g., empty cationic liposomes, empty cationic micelles, or empty cationic emulsions), and a second composition comprising a therapeutically effective amount of expression vectors (e.g., non-viral expression vectors not associated with liposomes) that are CpG-free or CpG-reduced, where the expression vectors comprise a first nucleic acid sequence encoding: i) a first therapeutic protein, and/or ii) a first biologically active nucleic acid molecule. In other embodiments, such first and second compositions are sequentially administered (e.g., systemically) to a subject such that the first therapeutic protein and/or the biologically active nucleic acid molecule is/are expressed in the subject (e.g., at a therapeutic level, for at least 5 or at least 50 days, such that a disease or condition is treated or a physiological trait is altered).

Work conducted during the development of embodiments of the present disclosure has shown that a single injection (e.g., intravenous injection) of cationic liposomes, followed shortly thereafter by injection (e.g., intravenous injection) of CpG-free vectors encoding a therapeutic protein produces circulating protein levels many times (e.g., 10-20 times higher) than the therapeutic serum level for the protein for a prolonged period. Such administration also increased circulating neutrophil counts many fold weeks after the treatment.

Work conducted during the development of embodiments of the present disclosure (e.g., as shown in Example 1 below) has shown that a single intravenous injection of cationic liposomes, followed two minutes later by intravenous injection of CpG-free plasmid vectors encoding human granulocyte-colony stimulating factor (hG-CSF) produces circulating hG-CSF protein levels 10-20 times higher than the therapeutic serum hG-CSF level (greater than or equal to 100 pg/ml) for at least 63 days (see, FIG. 3). Such administration also increased circulating neutrophil counts 10 fold, 3 weeks following intravenous injection into mice (FIG. 4). In contrast, one systemic injection of cationic liposome-DNA complexes containing a similar, but CpG-containing) hG-CSF plasmid vector was unable to produce detectable (>20 pg/ml) hG-CSF protein levels even at day 3 after injection, and failed to increase neutrophil counts at any point after injection (see, Tu et al., JBC, 275 (39):30408-30416, 2000; herein incorporated by reference in its entirety). Moreover, the approach presented in Example 1 that was used to prolong expression at therapeutic levels of human G-CSF did not appear to cause significant toxicity in the mice.

Thus, the approach provided herein for expression in vivo overcomes the critical limitation that has up to now precluded the successful therapeutic application of systemic non-viral gene delivery. Namely, its inability to express delivered genes at therapeutic levels for the extended periods generally required to produce important therapeutic or physiological endpoints. As shown in Example 1, embodiments of the methods provided herein accomplish such long lasting expression of a therapeutic protein with non-viral vectors without having to incorporate viral genes into the vectors. This is important as other approaches relied on the insertion of at least one viral gene plus the viral DNA sequence to which its protein product binds (the EBNA-1 gene together with the EBV family of repeat sequences inserted into the DNA vector) has been required in order to overcome this transient gene expression limitation (see, Tu et al., above). Moreover, in addition to the high hG-CSF protein levels found after 63 days in Example 1 (FIG. 1), similar high levels of expression were measured and found on days 14, 21, 28, and 49 after injection, indicating that once achieved, these high therapeutic levels are maintained longer term. Also, Example 2 shows, in FIG. 17, over 400 days of high levels of expression. This high level and long term expression is significantly better than the mRNA approach provided by MODERNA, which, as shown in FIG. 3 of U.S. Pat. No. 8,754,062 for hG-CSF, only produced therapeutic levels of up to 4 days after a single IV injection.

In addition, the systems, methods, and compositions provided herein provide a versatile (e.g., non-viral) gene delivery and expression platform that can much more precisely control the duration of expression of delivered genes at therapeutic levels. This ability to control the duration of expression of delivered genes addresses another up to now critical unmet need within the gene therapy field, the ability to control the duration at which proteins are expressed at therapeutic levels. Specifically, there is now a wide and expanding spectrum of FDA-approved, recombinant, secreted human protein therapies. Different approved protein therapies must be present at therapeutic levels for very different durations in order to both effectively and safely treat patients. Recommended treatment durations of different protein therapies vary from less than two weeks (hG-CSF) to the lifetime of the patient (factor IX). For example, recombinant human G-CSF protein, Neupogen, is given daily for only the first 10 days of each three-week chemotherapy cycle. Serum hG-CSF levels return to baseline approximately 14 hours after each daily Neupogen dose. This 10 day treatment schedule is used because its neutrophil increasing effect is indicated only during this approximately 10 day period of chemotherapy-induced neutropenia. G-CSF elevation from days 11 to 21 is generally not beneficial, as the patient's own neutrophil producing capacity returns. Giving Neupogen beyond day 10 can cause toxic, neutrophilia-related side effects. In contrast, anti-TNF antibodies are routinely administered for months or years, and factor IX replacement for the lifetime of the patient. Thus, different proteins must be produced at therapeutic levels for different durations, from less than two weeks to the lifetime of the patient. Therefore, a gene therapy approach that can control the duration of gene expression at therapeutic levels it produces in patients achieves therapeutic endpoints while avoiding toxic side effects for a wide spectrum of now FDA-approved, human therapeutic proteins. Provided herein are various technologies that can be employed to provide this control. Five exemplary approaches are described below.

Figure 5:
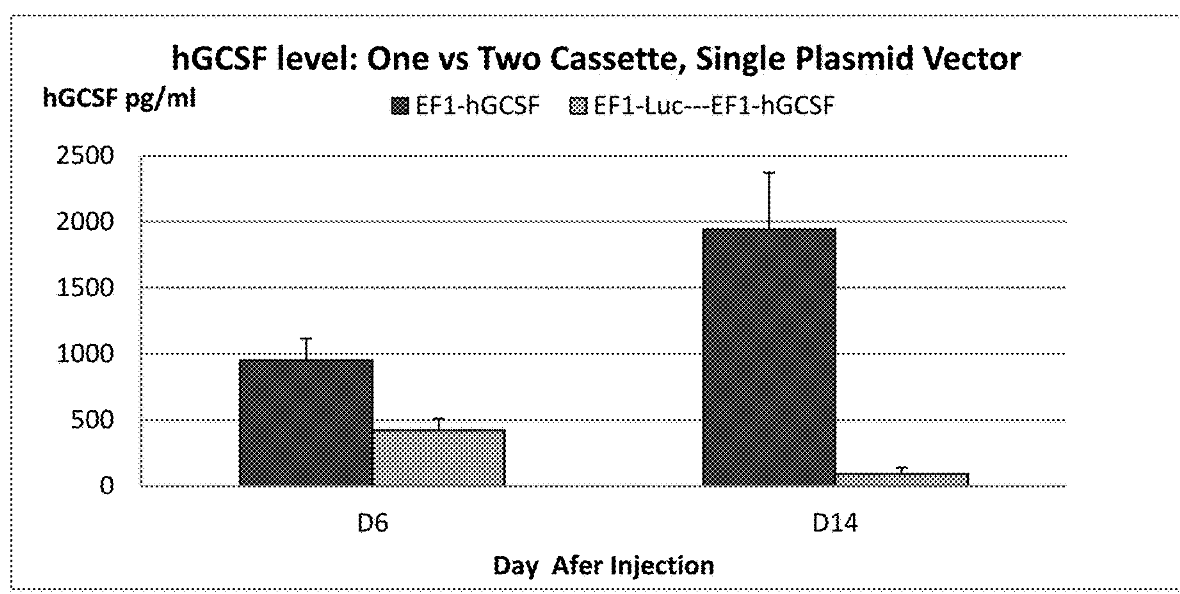
FIG. 5 shows serum human G-CSF levels produced in mice by sequential IV injection of either single or dual cassette, hG-CSF single plasmid vectors.

First, in certain embodiments, a second expression cassette is inserted into a single plasmid DNA vector or other vector. As shown in Example 1, in contrast to the single expression cassette hG-CSF plasmid vector that was used, which produces therapeutic hG-CSF levels for at least 63 days (FIG. 3), adding the second cassette limited therapeutic levels of hG-CSF protein produced to less than two weeks in mice (FIG. 5). Of note, the second expression cassette which drives the luciferase gene, is also expressed at high, controllable levels in IV injected mice.

Figure 6:
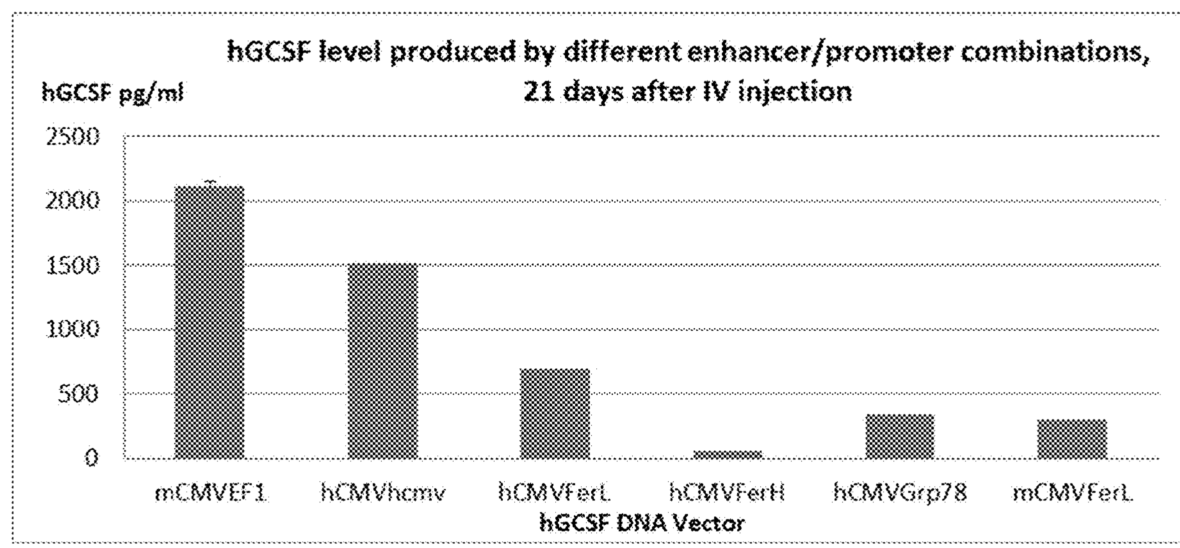
FIG. 6 shows serum hG-CSF levels in mice, 21 days after IV injection of cationic liposomes, then DNA containing different promoter-enhancer combinations linked to the hG-CSF gene.

Second, as shown in Example 1, a series of different, CPG-free promoter-enhancer combinations were generated in single cassette plasmid vectors that express hG-CSF at therapeutic levels for a range of different durations following a single IV injection in mice (FIG. 6). Of note, multi-expression cassette, single plasmid DNA vectors that contain different cassettes incorporating different promoter enhancer combinations are capable of expressing different therapeutic proteins at different levels for different durations from a single DNA vector. This allows a single DNA vector to express multiple different therapeutic proteins (e.g., one, two, three, four, five, six or more therapeutic proteins). Each individual protein is then expressed for the required duration at its appropriate therapeutic level. Such an approach is one way to overcome the prohibitive costs now incurred by combining two or more recombinant protein therapies in a single patient.

Figure 7:
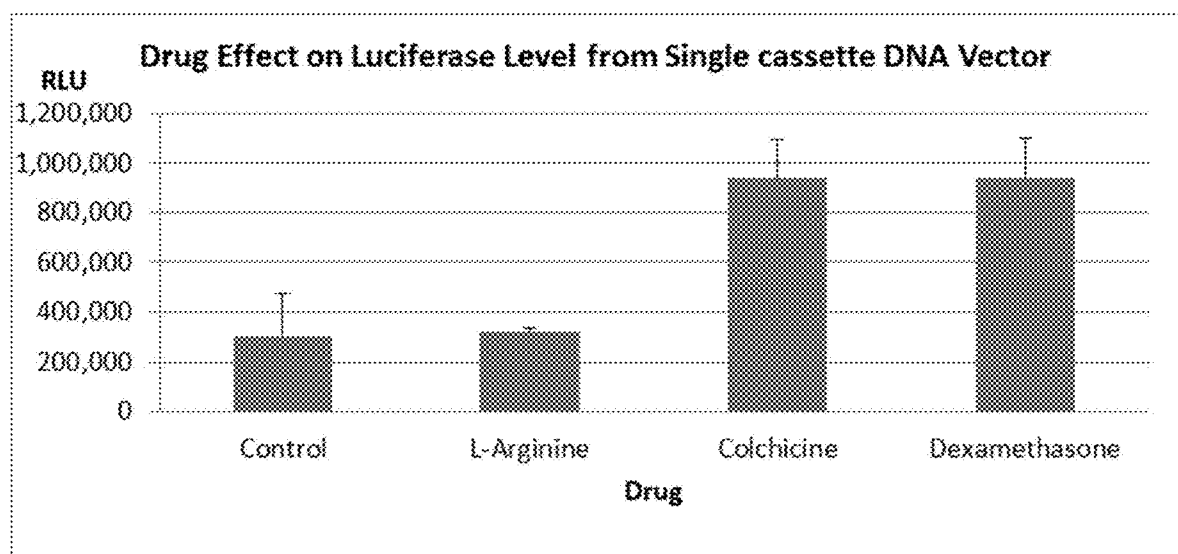
FIG. 7 shows mouse lung luciferase levels, 7 days after sequential IV injection of cationic liposomes, then single cassette, EF1-luciferase DNA alone or together with a particular drug.
Figure 8:
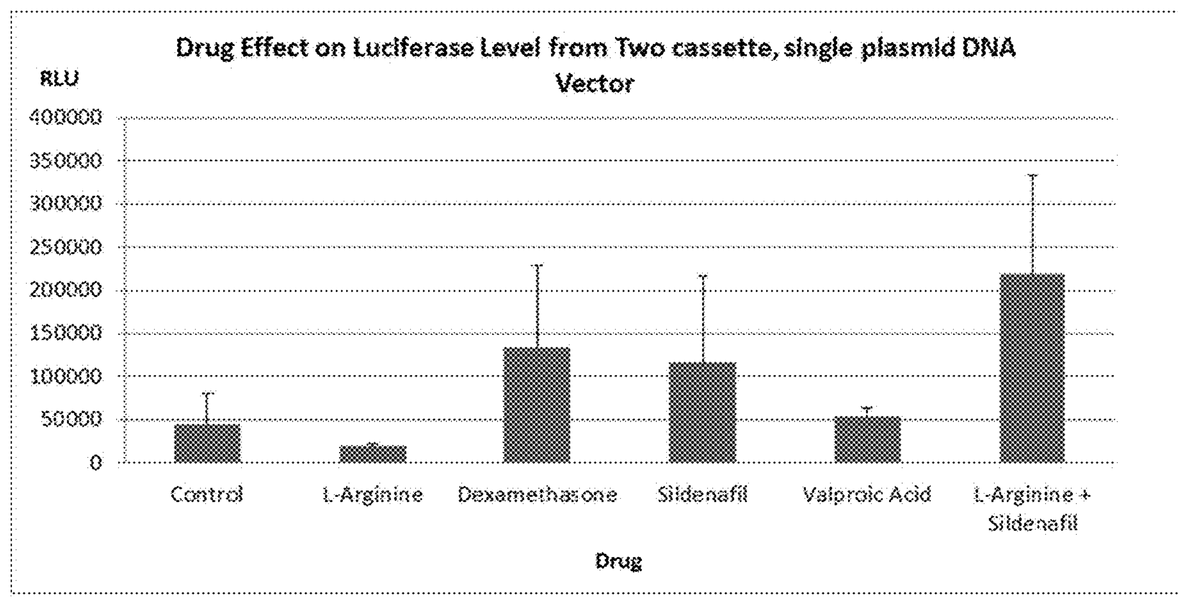
FIG. 8 shows mouse lung luciferase levels, 7 days after sequential IV injection of cationic liposomes, then dual cassette, EF1-hG-CSF-EF1-luciferase DNA alone or with certain drug(s).

Third, as described in Example 1, it was shown that co-injecting now FDA-approved drugs, singly or in selected combinations with the cationic liposomes can selectively either increase or decrease the level/duration of expression of the gene subsequently delivered by sequential IV injection in mice (FIGS. 7 and 8).

Figure 11:
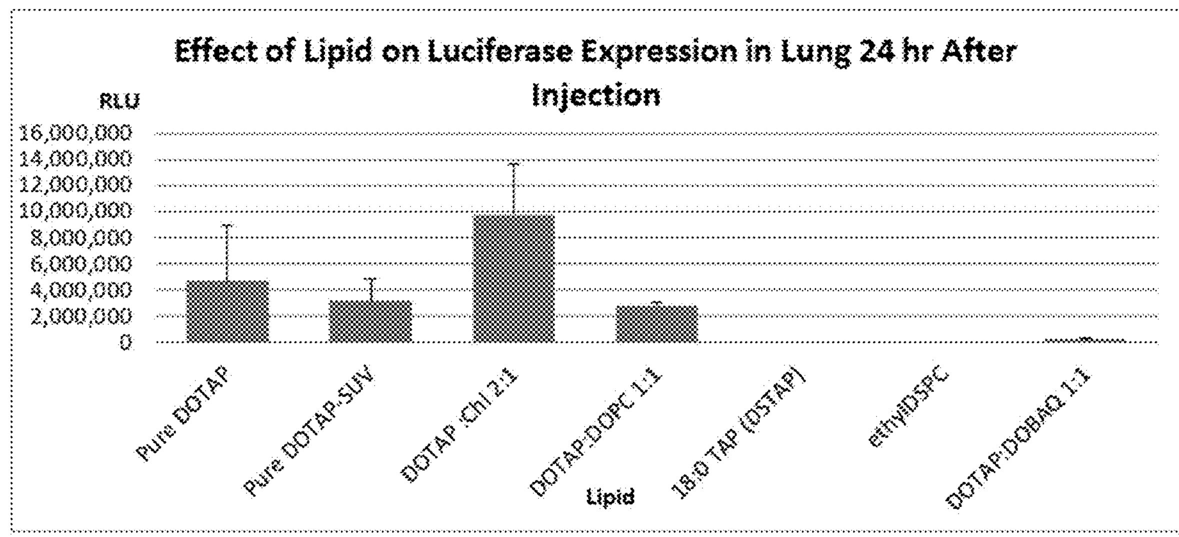
FIG. 11 shows mouse lung luciferase levels, 1 day after sequential IV injection of one of seven different cationic liposome formulations, then single cassette, EF1-luciferase DNA.

Fourth, as demonstrated in Example 1, varying the cationic liposome size, as well as the lipid composition can also control the level and duration of expression of genes delivered by sequential cationic liposome then DNA injection (FIG. 11).

Figure 14:
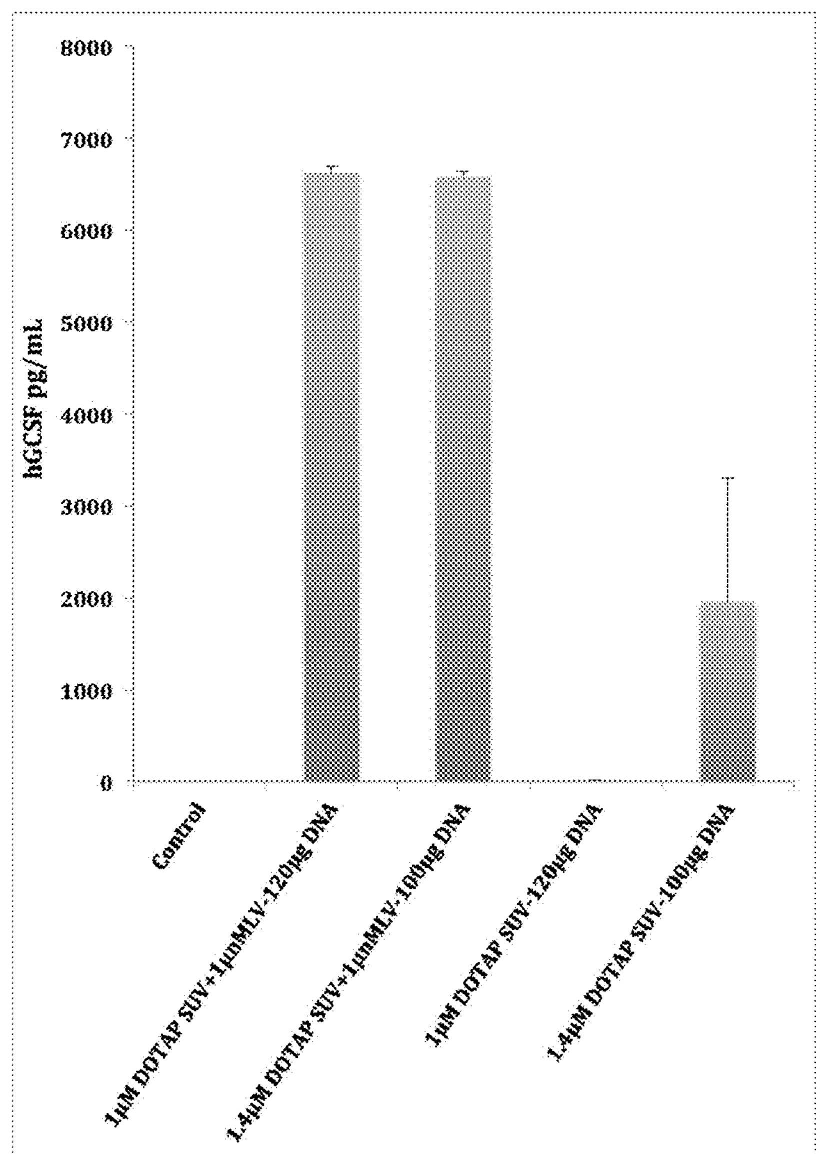
FIG. 14 shows serum human G-CSF levels produced in mice, 1 day after sequential, IV cationic liposome injection, with or without co-injection of neutral liposomes, followed by IV injection of a dual cassette, single plasmid vector.
Figure 15:
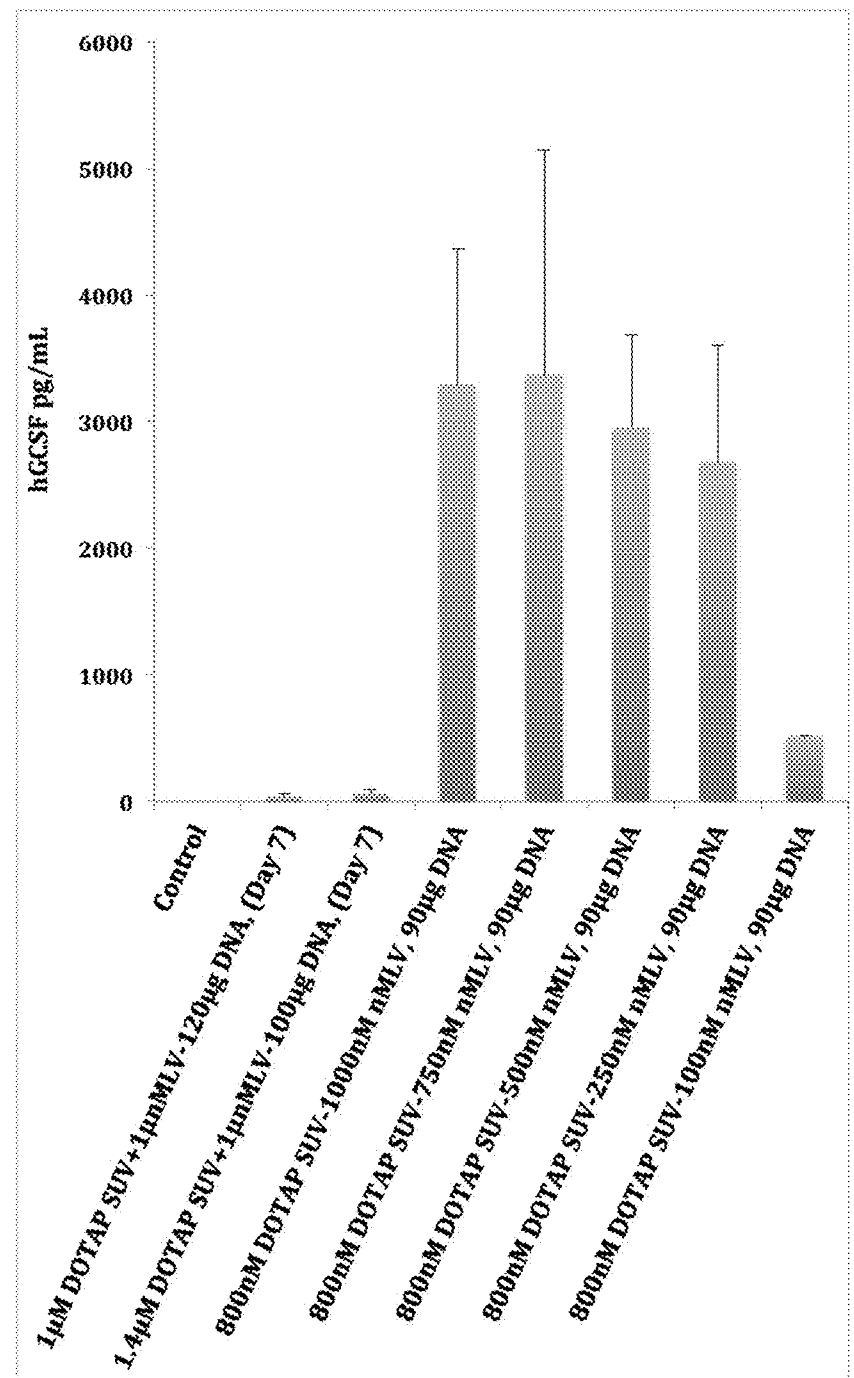
FIG. 15 shows serum human G-CSF levels produced in mice, 1 or 7 days after sequential, IV cationic liposome co-injection with neutral liposomes, followed by IV injection of a dual cassette plasmid vector.
Figure 26:
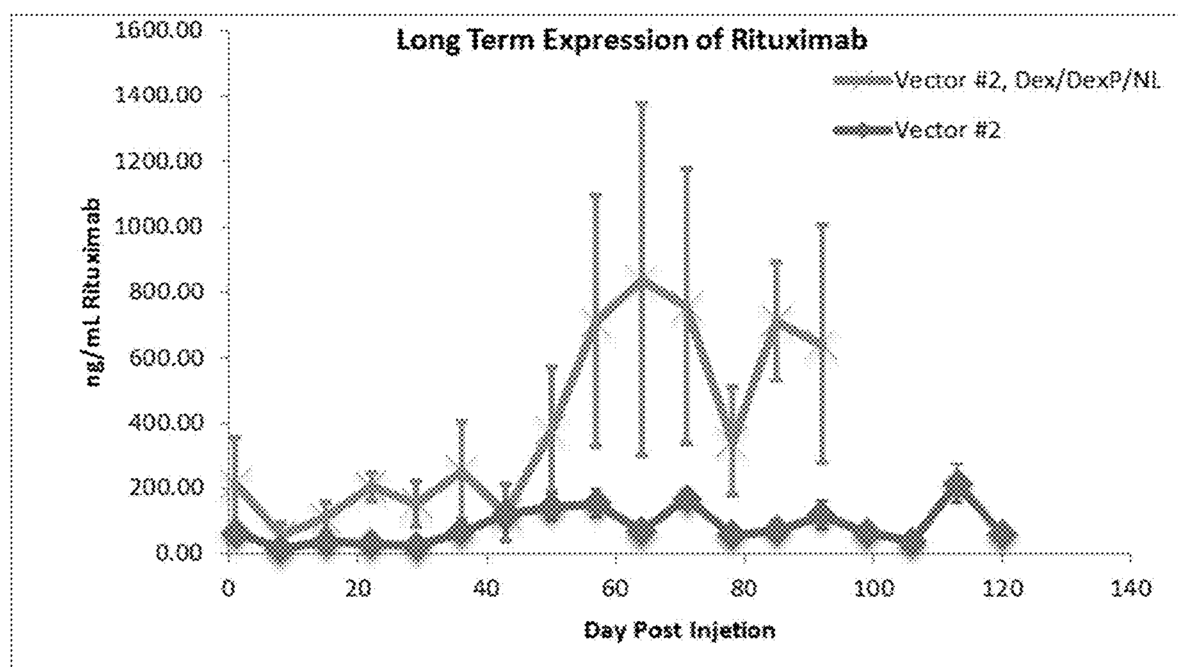
FIG. 26 shows dexamethasone pre-injection followed by one IV sequential injection of DexP cationic liposomes plus neutral lipid then a dual cassette, single plasmid DNA vector encoding Rituximab produces extended serum levels of fully functional Rituximab protein in mice.
Figure 29:
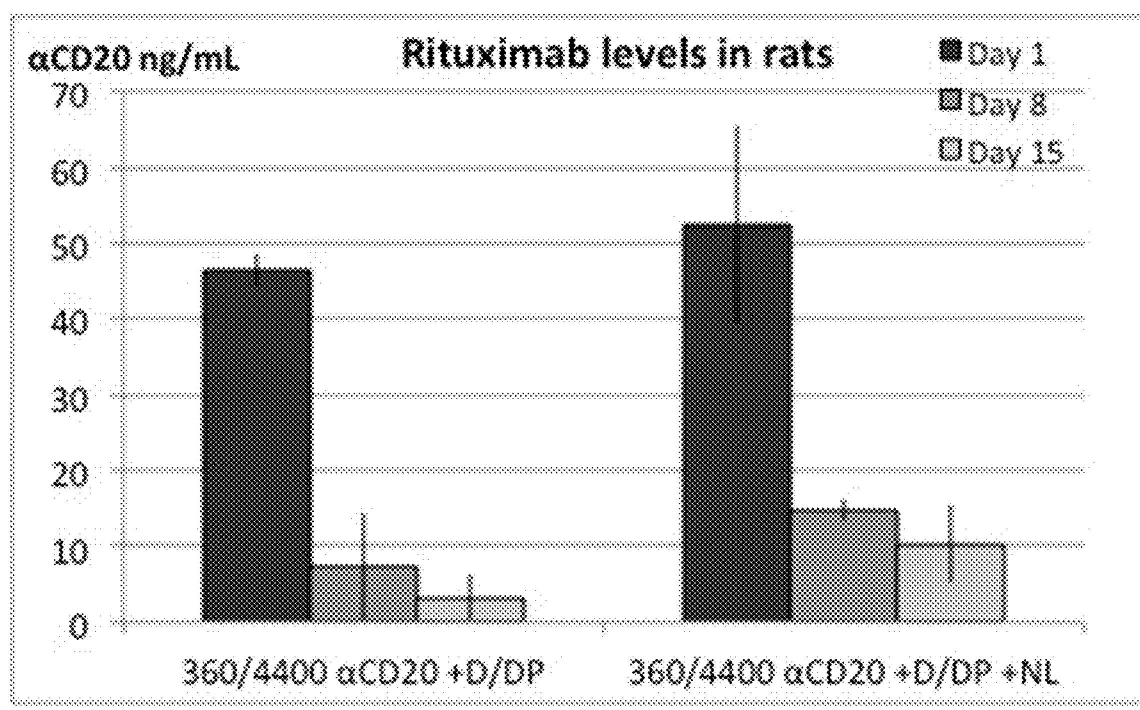
FIG. 29 shows IP pre-injection of dexamethasone, then neutral lipid plus 2.5 mole % dexamethsone palmitate in DOTAP liposomes increases serum Rituximab levels over time in rats.

Fifth, as demonstrated in example 14, the addition of neutral lipids together with dexamethasone and dexamethasone palmitate can increase the duration of gene expression (FIGS. 26 and 29). In contrast, the administration of neutral lipid alone can decrease the duration of gene expression (FIGS. 14 and 15).

Figure 9:
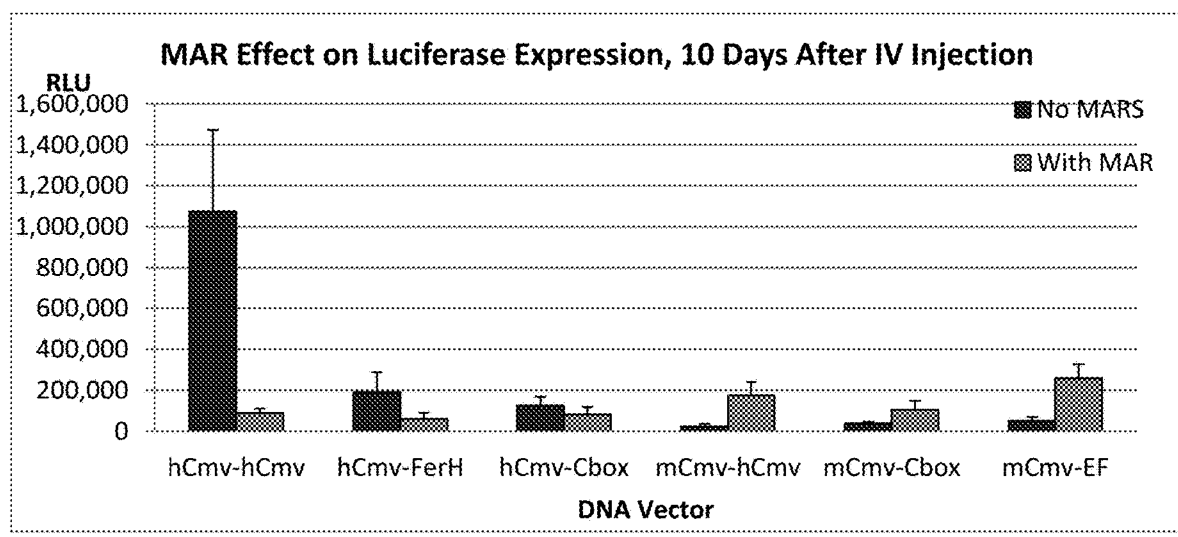
FIG. 9 shows mouse lung luciferase levels, 10 days after sequential IV injection of cationic liposomes, then a DNA vector containing one of a series of different promoter-enhancer combinations, each either with or without MARs, and all linked to the luciferase gene.

In addition, some literature also describes that matrix attachment regions (MAR) should be incorporated into DNA vectors in order to produce prolonged expression following their IV injection (Argyros et al., J Mol Med (2011) 89:515-529, herein incorporated by reference in its entirety). In contrast, work conducted during development of embodiments of the present disclosure indicate that the presence of such MAR elements do not increase, and in some vectors decrease the duration of gene expression produced by IV, sequential injection of cationic liposomes followed by CPG-free plasmid DNA (FIG. 9).

In certain embodiments, the present disclosure employs polycationic structures (e.g., empty cationic liposomes, empty cationic micelles, or empty cationic emulsions) not containing vector DNA, which are administered to a subject prior to vector administration. In certain embodiments, the polycationic structures are cationic lipids and/or are provided as an emulsion. The present disclosure is not limited to the cationic lipids employed, which can be composed, in some embodiments, of one or more of the following: DDAB, dimethyldioctadecyl ammonium bromide; DPTAP (1,2-dipalmitoyl 3-trimethylammonium propane); DHA; prostaglandin, N-[1-(2,3-Dioloyloxy)propyl]-N,N,N-trimethylammonium methyl sulfate; 1,2-diacyl-3-trimethylammonium-propanes, (including but not limited to, dioleoyl (DOTAP), dimyristoyl, dipalmitoyl, disearoyl); 1,2-diacyl-3-dimethylammonium-propanes, (including but not limited to, dioleoyl, dimyristoyl, dipalmitoyl, disearoyl) DOTMA, N-[1-[2,3-bis(oleoyloxy)]propyl]-N,N,N-trimethylammoniu-m chloride; DOGS, dioctadecylamidoglycylspermine; DC-cholesterol, 3.beta.-[N-(N',N'-dimethylaminoethane) carbamoyl]cholesterol; DOSPA, 2,3-dioleoyloxy-N-(2(sperminecarboxamido)-ethyl)-N,N-dimethyl-1-propanami-nium trifluoroacetate; 1,2-diacyl-sn-glycero-3-ethylphosphocholines (including but not limited to dioleoyl (DOEPC), dilauroyl, dimyristoyl, dipalmitoyl, distearoyl, palmitoyl-oleoyl); beta-alanyl cholesterol; CTAB, cetyl trimethyl ammonium bromide; diC14-amidine, N-t-butyl-N'-tetradecyl-3-tetradecylaminopropionamidine; 14Dea2, O,O'-ditetradecanolyl-N-(trimethylammonioacetyl) diethanolamine chloride; DOSPER, 1,3-dioleoyloxy-2-(6-carboxy-spermyl)-propylamide; N,N,N',N'-tetramethyl-N,N'-bis(2-hydroxylethyl)-2,3-dioleoyloxy-1,4-butan-ediammonium iodide; 1[2-acyloxy)ethyl]2-alkyl (alkenyl)-3-(2-hydroxyethyl-) imidazolinium chloride derivatives such as 1-[2-(9 (Z)-octadecenoyloxy)eth-yl]-2-(8(Z)-heptadecenyl-3-(2-hydroxyethyl)imidazolinium chloride (DOTIM), 1-[2-(hexadecanoyloxy)ethyl]-2-pentadecyl-3-(2-hydroxyethyl) imidazolinium chloride (DPTIM); 1-[2-tetradecanoyloxy) ethyl]-2-tridecyl-3-(2-hydroxyeth-yl)imidazolium chloride (DMTIM) (e.g., as described in Solodin et al. (1995) Biochem. 43:13537-13544, herein incorporated by reference); 2,3-dialkyloxypropyl quaternary ammonium compound derivates, containing a hydroxyalkyl moiety on the quaternary amine, such as 1,2-dioleoyl-3-dimethyl-hydroxyethyl ammonium bromide (DORI); 1,2-dioleyloxypropyl-3-dimethyl-hydroxyethyl ammonium bromide (DORIE); 1,2-dioleyloxypropyl-3-dimethyl-hydroxypropyl ammonium bromide (DORIE-HP), 1,2-dioleyloxypropyl-3-dimethyl-hydroxybutyl ammonium bromide (DORIE-HB); 1,2-dioleyloxypropyl-3-dimethyl-hydroxypentyl ammonium bromide (DORIE-HPe); 1,2-dimyristyloxypropyl-3-dimethyl-hydroxylethyl ammonium bromide (DMRIE); 1,2-dipalmityloxypropyl-3-dimethyl-hydroxyethyl ammonium bromide (DPRIE); 1,2-disteryloxypropyl-3-dimethyl-hydroxyethyl ammonium bromide (DSRIE) (e.g., as described in Felgner et al. (1994) J. Biol. Chem. 269:2550-2561, herein incorporated by reference in its entirety). Many of the above-mentioned lipids are available commercially from, e.g., Avanti Polar Lipids, Inc.; Sigma Chemical Co.; Molecular Probes, Inc.; Northern Lipids, Inc.; Roche Molecular Biochemicals; and Promega Corp.

In certain embodiments, the present disclosure employs CpG-reduced or CpG-free expression vectors. An initial sequence that contains CpG dinucleotides (e.g., wild-type version of human G-CSF), may be modified to remove CpG dinucleotides by altering the nucleic acid sequence. FIG. 2 shows a CpG-free version of human G-CSF, with sequences that have been changed to removed CpGs underlined. Such CpG di-nucleotides can be suitably reduced or eliminated not just in a coding sequence, but also in the non-coding sequences, including, e.g., 5' and 3' untranslated regions (UTRs), promoter, enhancer, polyA, ITRs, introns, and any other sequences present in the nucleic acid molecule or vector. CpG di-nucleotides may be located within a codon triplet for a selected amino acid. There are five amino acids (serine, proline, threonine, alanine, and arginine) which have one or more codon triplets that contain a CpG di-nucleotide. All five of these amino acids have alternative codons not containing a CpG di-nucleotide that can be changed to, to avoid the CpG but still code for the same amino acid as shown in Table 1 below. Therefore, the CpG di-nucleotides allocated within a codon triplet for a selected amino acid may be changed to a codon triplet for the same amino acid lacking a CpG di-nucleotide.

TABLE 1

| Amino Acid | DNA Codons Containing CpG | DNA Codons Lacking CpG |
|---|---|---|
| Serine (Ser or S) | TCG | TCT, TCC, TCA, AGT, AGC |
| Proline (Pro or P) | CCG | CCT, CCC, CCA, |
| Threonine (Thr or T) | ACG | ACA, ACT, ACC |
| Alanine (Ala or A) | GCG | GCT, GCC, GCA |
| Arginine (Arg or R) | CGT, CGC, CGA, CGG | AGA, AGG |

In addition, within the coding region, the interface between triplets should be taken into consideration. For example, if an amino acid triplet ends in a C-nucleotide which is then followed by an amino acid triplet which can start only with a G-nucleotide (e.g., Valine, Glycine, Glutamic Acid, Alanine, Aspartic Acid), then the triplet for the first amino acid triplet is changed to one which does not end in a C-nucleotide. Methods for making CpG sequences are shown, for example, in U.S. Pat. No. 7,244,609, which is herein incorporated by reference. A commercial service provided by INVIVOGEN is also available to produce CpG free (or reduced) nucleic acid sequences and vectors.

Provided below in Table 2 are exemplary promoters and enhancers that may be used in the vectors described herein. Such promoters, and other promoters known in the art, may be used alone or with any of the enhancers, or enhancers, known in the art. Additionally, when multiple proteins or biologically active nucleic acid molecules (e.g., two, three, four, or more) are expressed from the same vector, the same or different promoters may be used in conjunction with the subject nucleic acid sequence.

TABLE 2

| Promoter | Enhancer |
|---|---|
| CMV | human CMV |
| EF1α | mouse CMV |
| Ferritin (Heavy/Light) Chain | SV40 |
| GRP94 | Ubc |
| U1 | AP1 |
| UbC | hr3 |
| Beta Actin | IE2 |
| PGK1 | IE6 |
| GRP78 | E2-RS |
| CAG | MEF2 |
| SV40 | C/EBP |
| TRE | HNF-1 |

The present disclosure is not limited by the type of therapeutic proteins that is expressed. In certain embodiments, the therapeutic protein comprises an antibody or antibody fragments (e.g., F(ab) or F(ab')2). In other embodiments, the therapeutic protein is selected from the group consisting of an anti-inflammatory protein, coagulation protein, anti-cancer protein, anti-sepsis protein, etc.

EXAMPLES

Example 1

In Vivo Protein Expression Using Sequential Injection of Cationic Liposomes Followed by CPG-Free Expression Vectors This example describes various work using in vivo protein expression using sequential injection of cationic liposomes followed closely in time by CPG-free expression vectors.

Methods

Liposome Preparation

Pure DOTAP lipid as a lyophilized powder was purchased from Avanti polar lipids. Pure DOTAP cationic liposomes were prepared by re-suspending the lyophilized powder in a solution of 5% dextrose in water at a lipid concentration of 20 millimolar. The solution was then vortexed for 15 minutes to form multi-lamellar vesicles (MLV), mean particle size 350 nm, as measured by laser light scattering. Small uni-lamellar vesicles (SUV), mean particle size 75 nm, were then formed from MLV by sonication in a bath sonicator.

Plasmid Construction

General schematics for the vectors employed are provided in FIG. 1. In general, a CpG free DNA plasmid vector is typically composed of the following elements: enhancer/promoter/5'UTR of either mCMV/EF1/I126 (851 bp) or hCMV/hCMV/HTLV (873 bp), linked to a gene of interest (such as h-GCSF (615 bp) or soLux (1653 bp)), minimal polyA (63 bp), MARs derived from either βGlobin (434 bp), 21q21 (1055 bp) or IFN (820 bp) and an R6K Ori/Kan$^r$ (Kanamycin antibiotic resistant) expression cassette (1206 bp). R6KOri/Kan$^r$ DNA was designed as a base vector containing three endonuclease restriction enzyme sites, DraIII, EcoRI and NheI. It was assembled from gBlock four DNA fragments (IDT, IA) using the Gibson Assembly technique (NEB, MA). For MAR containing plasmids, a βGlobin MAR was inserted into the base vector at DraIII-EcoRI sites. The CpG-free nucleic acid sequence for h-GCSF is shown in FIG. 2.

The expression cassette was constructed using the puc19 plasmid backbone by sequentially inserting each DNA element between EcoRI and XbaI. Enhancer/Promoter elements containing 5' EcoRI and NheI sites were ligated to the 5'UTR, gene, pA or pA-MAR, as well as puc19 at EcoRI, EcoRV, BstEII, BglII and XbaI sites, respectively. The expression cassette was then digested with EcoRI-XbaI and inserted into the base vector at EcoRI-NheI, producing an expression plasmid containing restriction sites that can be used to insert a second expression cassette insertion. Dual (Luc- and GCSF) cassette expression plasmids were then constructed by inserting the hG-CSF expression cassette into the base vector at EcoRI-NheI. The second, Luc expression cassette was subsequently inserted into the G-CSF expression plasmid at EcoRI-NheI, producing a dual cassette, Luc and GCSF containing, single plasmid vector.

Plasmid Purification

Endotoxin-free plasmids were purified on 5'Prime Endo-free Maxi columns as follows. Briefly, 200 ml of bacteria containing the plasmid are grown overnight at 37C and then collected. Bacterial cells are lysed per the manufacturer's protocol. Endotoxin is removed using an EndoFree filter CS. Isopropanol is added to the lysate and then loaded onto a column. After successive washes, the column is centrifuged and air-dried for 10 min to ensure residual ethanol is removed. DNA is then eluted from the column with 1 ml of Lactated Ringers.

Mice 21 g female, CD-1 mice were purchased from Charles River. Housing, care and all procedures were performed according to IACUC approved guidelines.

Sequential Injection of Cationic Liposomes, then Plasmid DNA in Mice

Three to five mice were injected per group. Each mouse received a single IV injection of cationic liposomes (MLV or SUV), followed two minutes later by a single IV injection of a CPG-free, plasmid DNA vector.

Obtaining and Then Analyzing Mouse Serum for Human G-CSF Levels

Each mouse was anesthetized and then bled via the submandibular vein. Serum was then isolated from whole blood and human G-CSF levels measured in pg/ml, as performed strictly according to the manufacturer's specifications, using an R and D systems human G-CSF ELISA.

Obtaining and Then Analyzing Mouse Tissue for Luciferase Activity

Lung was homogenized with 500 ul of 1× Lysis buffer (Promega, Wis.). The homogenate was centrifuged at 3000×g at 4C for 10 min. and the supernatant collected. Luciferase activity was assayed using 20 μl of supernatant and 100 μl of Luciferase reagent for 10 seconds using a GloMax® Luminometer (Promega, Wis.).

Results/Description

Serum Human G-CSF Levels Produced in Mice by Sequential, IV Cationic Liposome Injection Followed by IV DNA Vector Injection Five mice were injected per group. Each mouse received a single IV injection of 800 nmoles of pure DOTAP cationic liposomes (MLV or SUV), followed two minutes later by a single IV injection of 80 μg of an mCMV-EF1-hGCSF, an hCMV-hCMV-hGCSF or an mCMV-EF1-luciferase, CPG-free, plasmid DNA vector. Serum hG-CSF levels were assessed beginning at day seven after IV injection, and at seven-day intervals thereafter.

Figure 3:
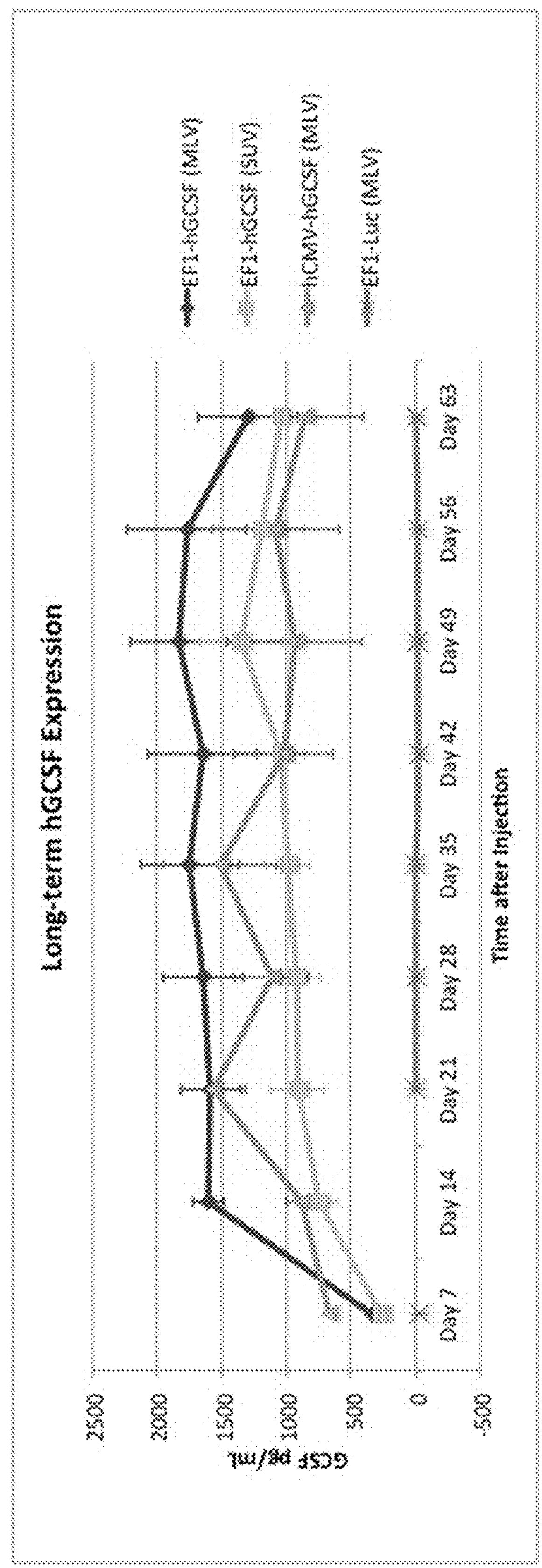
FIG. 3 shows a graph of serum human G-CSF levels produced in mice by sequential, IV cationic liposome injection followed by IV DNA vector injection.
Figure 4:
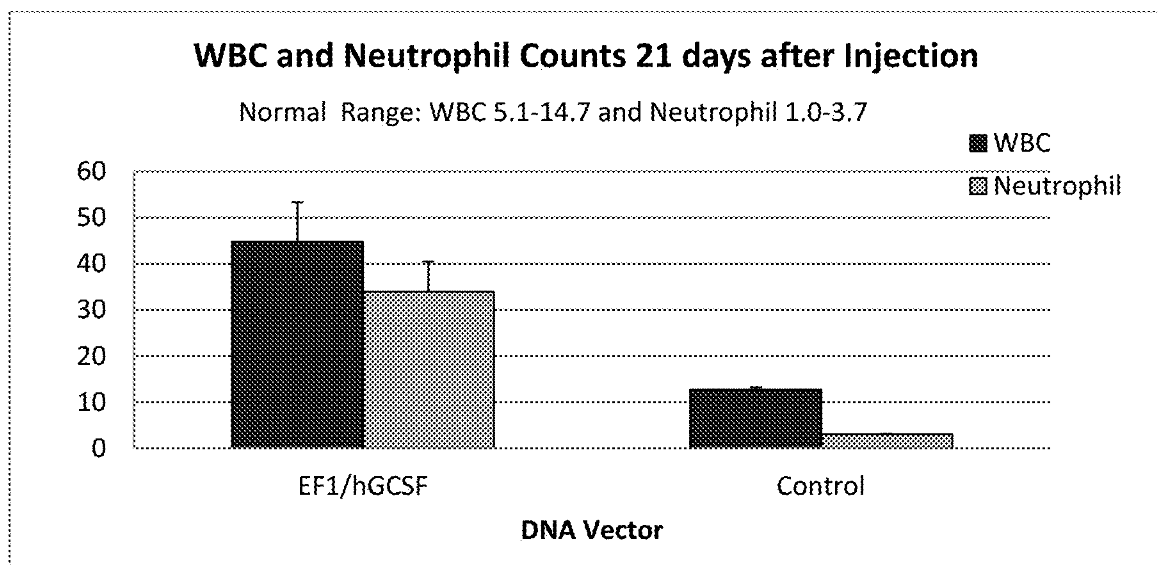
FIG. 4 shows a histogram of WBC and absolute neutrophil counts, 21 days after sequential, IV cationic liposome then DNA vector injection.

As shown in FIG. 3, all three DNA vectors containing the hG-CSF gene produced supra-therapeutic hG-CSF levels (≥100 pg/ml is required to increase neutrophil levels), at day seven after injection. Thereafter, hG-CSF levels rose progressively until day 21, and then remained stable until day 63, the last time point analyzed. In contrast, hG-CSF levels produced by identical, IV sequential injection of the EF1-luciferase DNA vector were undetectable throughout the course of the experiment.

WBC and Absolute Neutrophil Counts, 21 Days After Sequential, IV Cationic Liposome Then DNA Vector Injection Whole blood was collected from groups of 4 mice at day 21 following sequential, IV injection of DOTAP MLV, followed two minutes later by a single IV injection of either an EF1-hGCSF or an EF-1 luciferase-containing, CPG-free plasmid DNA vector. Blood from each mouse was then analyzed, in a blinded fashion, for total WBC, as well as absolute neutrophil counts by the University of California Davis veterinary diagnostics laboratory.

As shown in FIG. 4, one sequential IV injection of DOTAP cationic liposomes followed by IV injection of EF1-hG-CSF DNA increased absolute neutrophil counts approximately 10 fold and total WBC approximately 4 fold, 21 days following injection when compared to mock-injected control mice receiving sequential injection of an EF1-luciferase, plasmid DNA vector. These results document that the hG-CSF gene encoded protein product was fully functional in treated mice. Taken together, the high-level increases in absolute neutrophil counts produced by the EF1-hG-CSF DNA vector, coupled with the 10 to 15 fold above therapeutic hG-CSF protein levels produced at day 21 (see FIG. 3) demonstrate that a single, sequential IV injection of a cationic liposomes followed by a CPG-free DNA vector can produce prolonged therapeutic effects of a now FDA-approved recombinant human protein therapy.

Serum Human G-CSF Levels Produced in Mice by Sequential IV Injection of Either Single or Dual Cassette, hG-CSF Single Plasmid Vectors Sera were collected from groups of four mice at either day 6 or 14 following sequential, IV injection of 800 nmoles of pure DOTAP MLV cationic liposomes, followed two minutes later by IV injection of 40 μg either an EF1-luciferase—EF1-hGCSF (2 expression cassette) or an EF1-hGCSF (1 expression cassette), CPG-free, single plasmid DNA vector.

As shown in FIG. 5, the single as well as dual cassette DNA vectors containing the hG-CSF gene each produced supra-therapeutic serum hG-CSF levels (≥100 pg/ml required to increase neutrophil counts) at day six after injection, 951 and 423 pg/ml, respectively. The single cassette vector produced even higher therapeutic levels, 1941 pg/ml, at day 14. In contrast, hG-CSF levels produced at day 14 by the dual cassette, single plasmid DNA vector had fallen to a sub-therapeutic level (93 pg/ml), as hG-CSF protein levels below 100 pg/ml are sub-therapeutic. Thus, adding a second expression cassette can control the duration of expression of the gene contained in the first cassette.

Serum hG-CSF Levels in Mice, 21 Days After IV Injection of Cationic Liposomes, then DNA Containing Different Promoter-enhancer Combinations Linked to the hG-CSF Gene Sera were collected from groups of four mice, 21 days following sequential, IV injection of 800 nmoles of pure DOTAP MLV cationic liposomes, followed two minutes later by IV injection of 60 μg of the hG-CSF gene, linked to one of the following enhancer-promoter combinations, mCMV-EF1, hCMV-hCMV, hCMV-hferritin light chain, hCMV-hferritin heavy chain, hCMV-glucose-regulated protein 78 or mCMV-hferritin light chain, each in a CPG-free, single cassette, DNA vector.

As shown in FIG. 6, a range of supra-therapeutic, hG-CSF serum levels were produced at day 21 by the mCMV-EF-1 (2120 pg/ml), hCMV-hCMV (1516 pg/ml), hCMV-FerL (699 pg/ml), hCMV-Grp78 (343 pg/ml) and mCMV-FerL (303 pg/ml)-driven DNA vectors, each linked to the hG-CSF gene. In contrast, the hCMV-FerH-hG-CSF DNA vector (52 pg/ml) produced a sub-therapeutic hG-CSF level. Taken together, these results reveal that changing the promoter-enhancer combination can produce a range of different hG-CSF protein levels, from more than 20 fold above therapeutic to sub therapeutic, 21 days after a single injection. (hG-CSF protein levels ≥100 pg/ml are required to increase neutrophil counts).

Mouse Lung Luciferase Levels, 7 Days After Sequential IV Injection of Cationic Liposomes, then Single Cassette, EF1-luciferase DNA Alone or Together with a Drug Lungs were collected from groups of four mice, 7 days following sequential, IV injection of 800 nmoles of pure DOTAP MLV cationic liposomes alone, or containing 2 mg/kg of L-arginine, 0.01 mg/kg of colchicine or 1 mg/kg of dexamethasone. In each case, cationic liposome injection was followed two minutes later by IV injection of 40 μg of an mCMV-EF1-luciferase, CPG-free, single cassette, DNA vector.

As shown in FIG. 7, when compared to mice receiving sequential injection of DOTAP MLV alone (control), mice receiving either colchicine or dexamethasone together with the liposomes showed higher luciferase activity in the lung. In contrast, mice receiving L-arginine together with liposomes failed to increase gene expression levels. Thus, co-injecting selected drugs together with the liposomes can increase the level and duration of expression of genes delivered by sequential cationic liposome then DNA injection.

Mouse Lung Luciferase Levels, 7 Days After Sequential IV Injection of Cationic Liposomes, Then Dual Cassette, EF1-hG-CSF-EF1-luciferase DNA Alone or With Drug(s)

Lungs were collected from groups of four mice, 7 days following sequential, IV injection of 800 nmoles of pure DOTAP MLV cationic liposomes alone, or containing 2 mg/kg of L-arginine, 1 mg/kg of dexamethasone, 0.02 mg/kg of sildenafil, 0.1 mg/kg of valproic acid or 2 mg/kg of L-arginine plus 0.02 mg/kg of sildenafil (VIAGRA). In each case, cationic liposome injection was followed two minutes later by IV injection of 40 μg of EF1-luciferase—EF1-hGCSF, a 2 expression cassette, CPG-free single plasmid DNA vector.

As shown in FIG. 8, when compared to mice receiving sequential injection of DOTAP MLV alone (control), mice receiving dexamethasone, valproic acid or sildenafil alone, or L-arginine plus sildenafil together with the liposomes showed higher luciferase activity in the lung. In contrast, mice receiving either L-arginine or valproic acid together with liposomes were either lower than or comparable to controls. Thus, depending on the drug co-injected, expression levels of the delivered gene can be increased or reduced.

Mouse Lung Luciferase Levels, 10 Days After Sequential IV Injection of Cationic Liposomes, Then a DNA Vector Containing One of a Series of Different Promoter-Enhancer Combinations, Each Either With or Without MARs and all Linked to the Luciferase Gene Lungs were collected from groups of three mice, 10 days following sequential, IV injection of 800 nmoles of pure DOTAP MLV cationic liposomes, followed two minutes later by IV injection of 40 μg of the luciferase gene, linked to one of the following enhancer-promoter combinations: hCMV-hCMV, hCMV-human ferritin heavy chain, hCMV-CBOX (human Carboxypeptidase B1), mCMV-hCMV, mCMV-CBOX and mCMV-EF1, each linked to the luciferase gene in a CPG-free, single cassette, DNA vector.

FIG. 9 shows that DNA vectors lacking MARs, and containing the hCMV enhancer linked to the hCMV, ferritin heavy chain or CBOX promoters produced higher lung luciferase levels than the corresponding vectors containing MAR elements. In contrast, DNA vectors containing both MARs and the mCMV enhancer linked to the hCMV, EF1 or CBOX promoters failed to produce lung luciferase levels as high as the corresponding vectors lacking MAR elements. Thus, CPG-free DNA vectors lacking MARs can produce more durable expression than MAR-containing vectors.

Mouse Lung Luciferase Levels, 1 or 5 Days After IV Injection of PEI:EF-1 Luc DNA Complexes or Sequential IV Injection of Cationic Liposomes, then the Identical EF-1 Luc DNA Lungs were collected from groups of three mice, 1 or 5 days following IV injection of either 12.5 μg of CPG-free EF-1-Luc DNA vector complexed to 22 kDa linear PEI at a 1:4 N:P ratio, or sequential, IV injection of 900 nmoles of pure DOTAP MLV cationic liposomes, followed two minutes later by IV injection of 40 μg of the same EF-1-Luc DNA vector.

Figure 10:
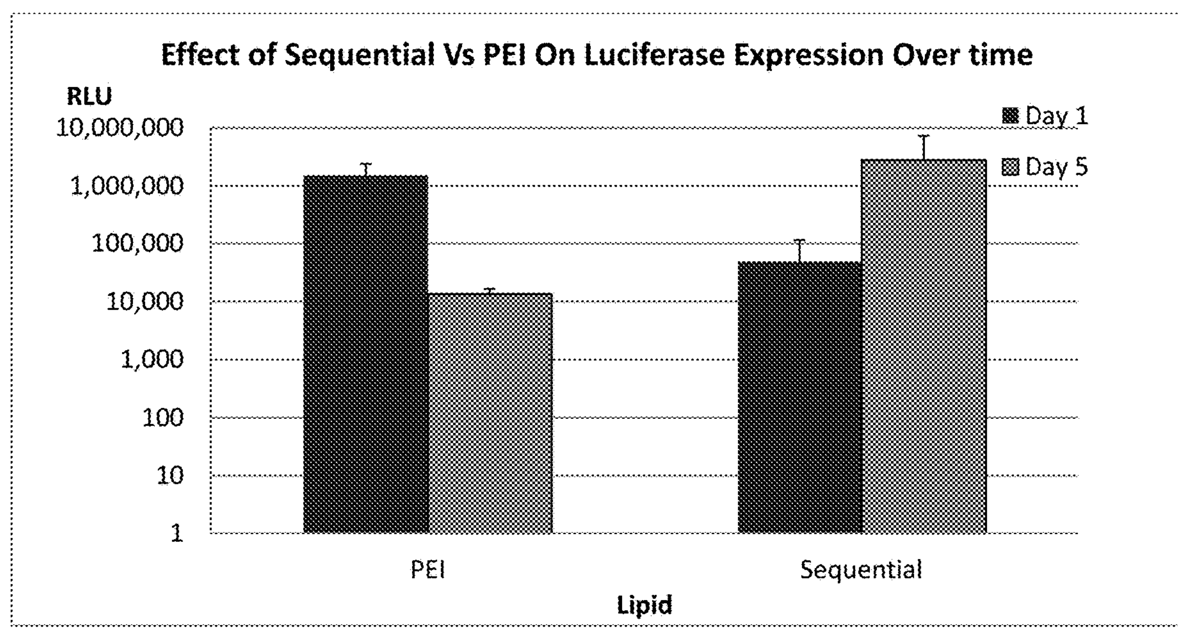
FIG. 10 shows mouse lung luciferase levels, 1 or 5 days after IV injection of PEI:EF-1 Luc DNA complexes or sequential IV injection of cationic liposomes, then the identical EF-1 Luc DNA.

FIG. 10 shows lung luciferase levels were consistently higher in the PEI:DNA injected mice than in the mice injected sequentially with cationic liposomes then DNA at day one following injection. However, lung luciferase levels had fallen approximately 100 fold in the PEI:DNA injected mice by day five. In direct contrast, lung luciferase levels from the sequentially IV injected mice had risen by day 5 after injection. Luciferase levels were up to 150 fold higher in sequentially-injected mice than those present in PEI:DNA injected mice also sacrificed at day 5. Thus, sequential cationic liposome then DNA injection produces higher levels of gene expression at later time points when compared to the same CPG free DNA injected as a PEI:DNA complex.

Mouse Lung Luciferase Levels, 1 Day After Sequential IV Injection of One of Seven Different Cationic Liposome Formulations, Then Single Cassette, EF1-Luciferase DNA Lungs were collected from groups of four mice, 1 day following sequential, IV injection of 800 nmoles of pure DOTAP MLV, pure DOTAP SUV, DOTAP:cholesterol 2:1 MLV, DOTAP:diolelyl phosphatidylcholine (DOPC) 1:1 MLV, DSTAP MLV, ethyl DSPC MLV or DOTAP:DOBAQ 1:1 MLV cationic liposomes. In each case, cationic liposome injection was followed two minutes later by IV injection of 80 μg of an mCMV-EF1-luciferase, CPG-free, single cassette, DNA vector.

As shown in FIG. 11, when compared to lung luciferase levels in mice receiving sequential IV injection of pure DOTAP MLV, mice receiving DOTAP SUV, DOTAP:chol or DOTAP:DOPC cationic liposome formulations produced gene expression levels approximating DOTAP MLV or higher. In contrast, mice receiving DSTAP, ethyl DSPC or DOTAP:DOBAQ MLV produced either very low or nearly undetectable lung luciferase levels. That DOTAP SUV produced gene expression levels approximating DOTAP MLV was unexpected because DOTAP MLV produces more than 1700 fold higher levels of gene expression than DOTAP SUV when injected as cationic liposome:DNA complexes (see, Nature Biotechnology, 15:167-173; 1996, herein incorporated by reference in its entirety).

Mouse Spleen Luciferase Levels, 1 Day After IV Injection Of PEI:EF-1 Luc DNA Complexes Alone or Mixed With One of Four Different Drugs Spleens were collected from groups of three mice, 1 day following IV injection of 12.5 μg of CPG-free EF-1-Luc DNA vector complexed to 22 kDa linear PEI at a 1:4 N:P ratio. Mice received an intraperitoneal injection of one ml of 5% DMSO either alone, or containing 200 μg of amlexanox, 1 mg of chloroquine, 200 μg of SAHA or 300 μg of tofacitinib per mouse, two hours prior to receiving IV PEI:DNA complexes.

Figure 12:
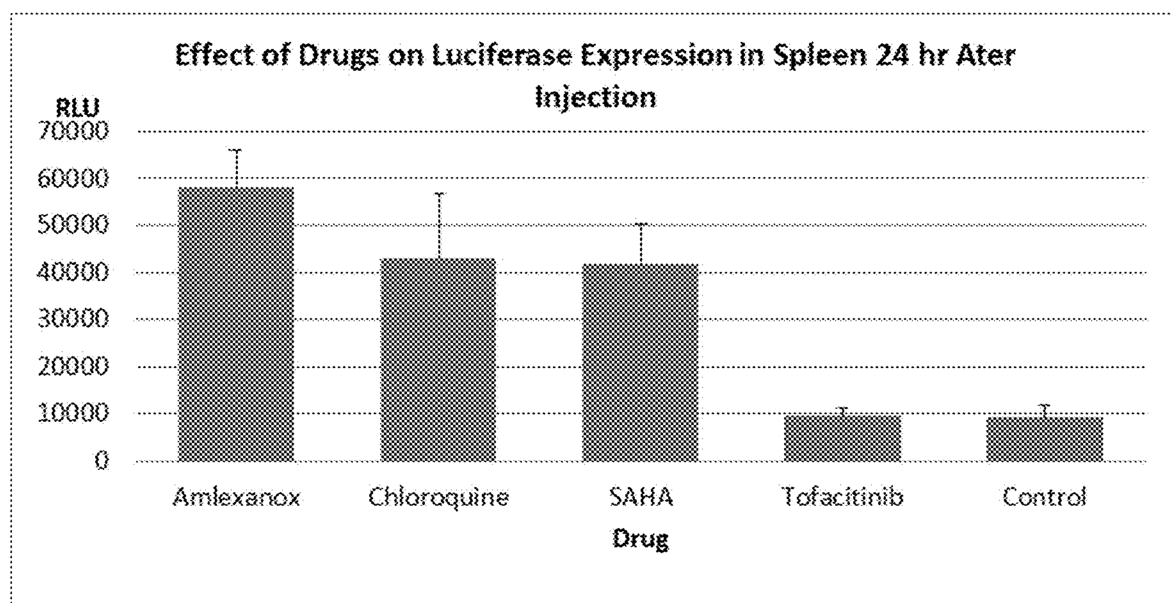
FIG. 12 shows mouse spleen luciferase levels, 1 day after IV injection of PEI:EF-1 Luc DNA complexes alone or mixed with one of four different drugs.

FIG. 12 shows pre-injection of the anti-inflammatory agents amlexanox, chloroquine or SAHA prior to injecting CPG-free DNA increased gene expression levels, whereas tofacitinib failed to increase gene expression. Amlexanox in particular, a selective inhibitor of the TBK1-induced interferon activation pathway, increased gene expression levels. Thus, pre-injection of selected anti-inflammatory agents may further increase the effectiveness of CPG-free DNA for gene therapy.

Mouse Lung Luciferase Levels, 1 or 7 Days After Sequential IV Injection of Cationic Liposomes, Then One of a Series of Dual Cassette, EF-1-Luc—hG-CSF DNA Vectors Lungs were collected from groups of four mice, 1 or 7 days following sequential, IV injection of 800 nmoles of pure DOTAP MLV cationic liposomes followed two minutes later by 40 μg of EF1-Luc—EF1-hGCSF, EF1-Luc—hCMV-hCMV-hGCSF, EF1-Luc—hCMV-hCBOX-hGCSF, EF1-Luc—hCMV-hREG1-hGCSF or EF1-Luc—mCMV-hCBOX-hGCSF 2 expression cassette, CPG-free single plasmid DNA vector.

Figure 13:
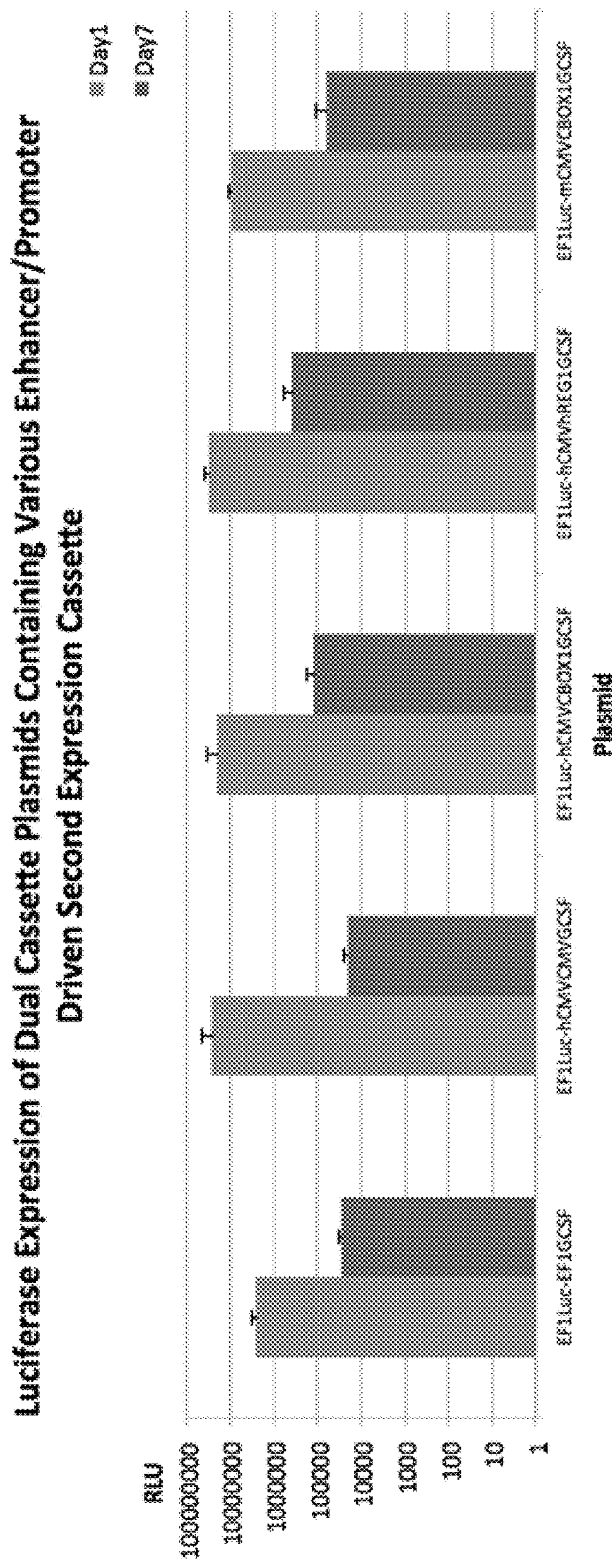
FIG. 13 shows mouse lung luciferase levels, 1 or 7 days after sequential IV injection of cationic liposomes, then one of a series of dual cassette, EF-1-Luc-hG-CSF DNA vectors.

FIG. 13 shows that when compared to mice receiving sequential injection of EF1-Luc—EF1-hGCSF dual cassette vector, containing the EF1 promoter in each cassette (control), mice receiving each of the other four dual cassette DNA vectors containing the EF1 promoter in one cassette and another promoter in the second cassette showed consistently higher luciferase activity in the lung at both day one and seven after injection. Dual cassette vectors containing a different promoter in each cassette produced lung luciferase levels up to tenfold or more higher at each time point than produced by the dual cassette vector containing the EF-1 promoter in both cassettes. Thus, using different promoter elements in different cassettes of multi-cassette vectors can significantly increase the level and duration of gene expression they produce.

Serum Human G-CSF Levels Produced in Mice, 1 Day After Sequential, IV Cationic Liposome Injection, With or Without Co-Injection of Neutral Liposomes, Followed by IV Injection of a Dual Cassette, Single Plasmid Vector Neutral MLV liposomes were prepared from Phospholipon 90H, Lipoid GmbH. The fatty acid content of this product is 15% palmitic acid, 85% stearic acid. Liposomes were prepared either by drying down the lipids in organic solvent on a rotary evaporator, then re-suspending the dried lipid film in a solution of 5% dextrose in water at a lipid concentration of 50 millimolar or by hydrating the lipid as a dry powder in 5% w/v dextrose. Both were prepared at 60 degrees C. The solution was then vortexed for 15 minutes to form MLV. Sera were collected from groups of four mice at day 1 following sequential, IV injection of buffer alone (control), 1000 nmoles of pure DOTAP SUV cationic liposomes, alone or co-injected with 1000 nmol of neutral MLV, followed two minutes later by IV injection of 120 μg an EF1-luciferase—EF1-hGCSF (2 expression cassette), CPG-free, single plasmid DNA vector or 1400 nmoles of pure DOTAP SUV cationic liposomes, alone or co-injected with 1000 nmol of neutral MLV, followed two minutes later by IV injection of 100 μg of EF1-luciferase—EF1-hGCSF DNA.

As shown in FIG. 14, serum hG-CSF levels produced one day after sequentially co-injecting pure DOTAP SUV together with neutral MLV then EF1-luciferase—EF1-hGCSF DNA were increased from 3 to 600 fold when compared to sequential injection of DOTAP SUV without neutral MLV. Thus, co-injecting neutral liposomes together with cationic liposomes can significantly increase peak levels of gene expression produced. In addition, co-injecting neutral liposomes appears to eliminate the variation in gene expression levels produced by sequentially injecting different ratios of cationic liposomes to DNA without co-injecting neutral liposomes.

Serum Human G-CSF Levels Produced in Mice, 1 or 7 Days After Sequential, IV Cationic Liposome Co-Injection with Neutral Liposomes, Followed by IV Injection of a Dual Cassette Plasmid Vector Sera were collected from groups of four mice at day 7 following sequential, IV injection of 1000 nmoles pure DOTAP SUV cationic liposomes co-injected with 1000 nmol of neutral MLV, followed two minutes later by IV injection of 120 μg of CPG-free, EF1-luciferase—EF1-hGCSF DNA or 1000 nmoles of pure DOTAP SUV cationic liposomes co-injected with 1400 nmol of neutral MLV, followed two minutes later by IV injection of 100 μg of EF1-luciferase—EF1-hGCSF DNA. Sera were also collected from groups of four mice at day 1 following sequential, IV injection of buffer only (control), 800 nmoles of pure DOTAP SUV cationic liposomes co-injected with 1000, 750, 500, 250 or 100 nmol of neutral MLV respectively, followed two minutes later by IV injection of 90 μg of EF1-luciferase—EF1-hGCSF.

As shown in FIG. 15, serum hG-CSF levels produced by co-injecting pure DOTAP SUV together with neutral MLV dropped by approximately 100 fold compared to the hG-CSF levels produced in the same mice one day after injection, (See FIG. 14 for hG-CSF levels produced at day 1 following injection of these same mice). Thus, co-injecting neutral liposomes with cationic liposomes can strongly alter both peak as well as longer-term expression of delivered genes. In addition, the ratio of neutral to cationic liposomes co-injected determines the extent to which co-injected neutral liposomes increase the expression of sequentially delivered genes.

Mouse Serum Hg-CSF Levels, 7 Day After Sequential IV Injection of Different Cationic Liposome Formulations, then Single Cassette, CPG-Free EF1-Hg-CSF DNA Sera were collected from groups of four mice, 7 days following sequential, IV injection of either 800 or 1000 nmoles of pure DOTAP SUV, or MLV cationic liposomes. Injection of each of the three cationic liposome formulations was followed two minutes later by IV injection of either 100 or 120 μg of an mCMV-EF1-h-G-CSF, CPG-free, single cassette, DNA vector. 0.1 μm extruded cationic liposomes were prepared from MLV by sequential extrusion through sized polycarbonate membranes under high argon gas pressure in a Lipex extrusion device.

Figure 16:
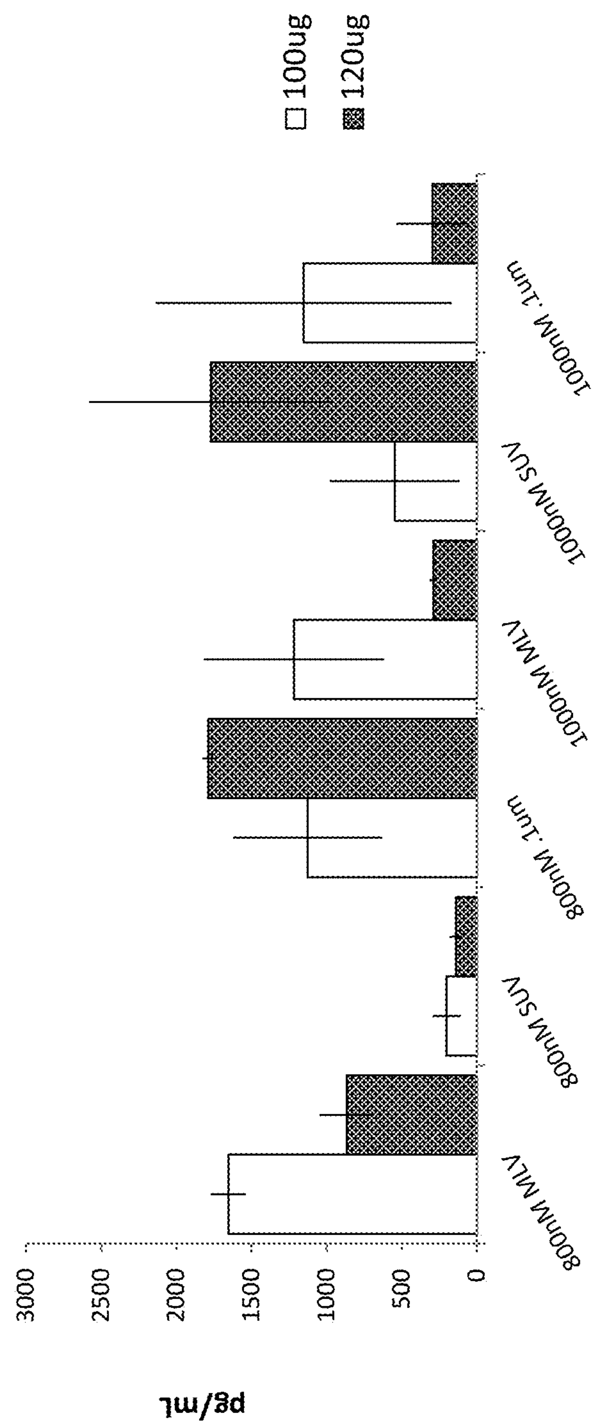
FIG. 16 shows serum human G-CSF levels produced in mice 7 days after sequential, IV cationic liposome injection with SUV, 0.1 μm extruded or MLV cationic liposomes, followed by IV injection of a EF1-hG-CSF plasmid vector.

As shown in FIG. 16, and in part depending on the ratio of nmoles cationic liposomes to μg DNA ratio injected, pure DOTAP SUV and 0.1 μm extruded cationic liposomes produced extended, high-level expression of hG-CSF as efficiently as that produced by MLV cationic liposomes. Therefore, SUV as well as 0.1 μm extruded (oligolamellar) cationic liposomes are as effective as MLV when used for sequential cationic liposome then CPG-free DNA injection.

Example 2

Long-Term Expression

Figure 17:
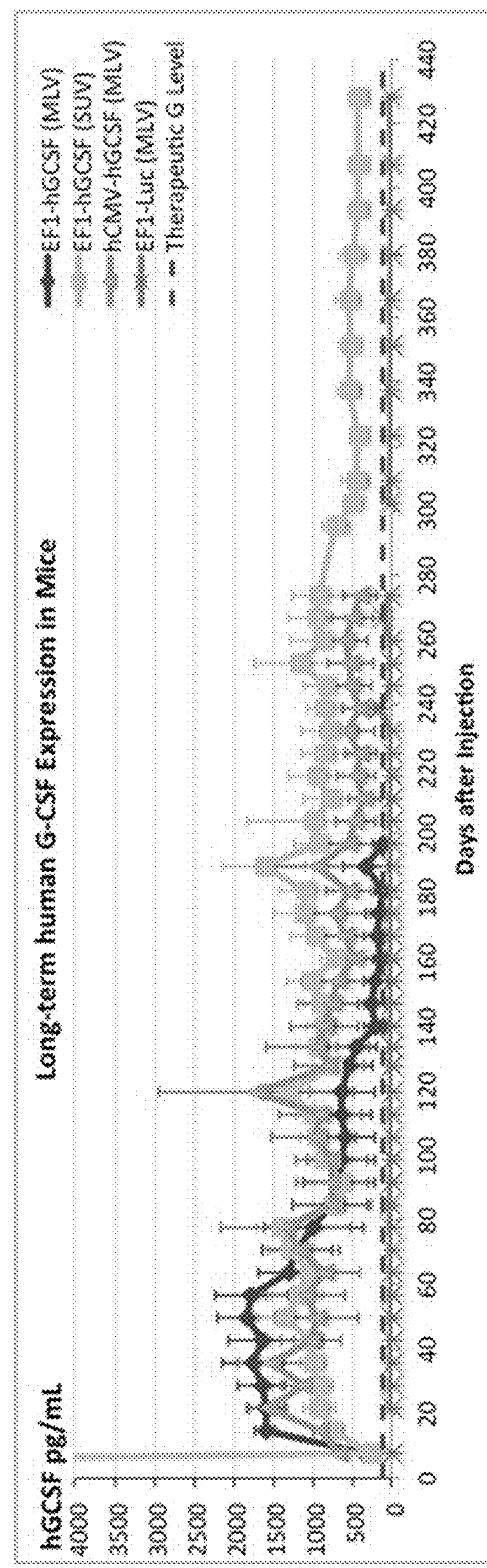
FIG. 17 shows results from Example 2, wherein one sequential IV injection of cationic liposomes followed by a CPG-free, human G-CSF DNA vector produces supra-therapeutic human G-CSF serum protein levels in mice for at least the next 428 days.

In this Example, five mice per group were sequentially injected with 800 nmol of either DOTAP MLV or SUV followed by 90 ug of a CPG-free plasmid vector containing an EF1- or hCMV-driven hG-CSF cDNA. Serum levels of human G-CSF protein were assessed at 7- or 14-day intervals for the subsequent 428 days following injection. Obtaining and analyzing mouse serum for human G-CSF levels was performed as follows. Each mouse was anesthetized and bled via submandibular vein. Serum was isolated from whole blood using serum separator tubes from BD. Human G-CSF levels were measured in pg/ml via an ELISA performed strictly according to the manufacturer's specifications, using an R&D systems human G-CSF ELISA. The results are shown in FIG. 17, and show that supra-therapeutic levels of human G-CSF protein were produced in fully immune-competent mice for at least 428 days after receiving a single IV injection of DOTAP SUV liposomes then an EF1-huG-CSF plasmid DNA vector.

Example 3

Protein Expression in Rats

Figure 18:
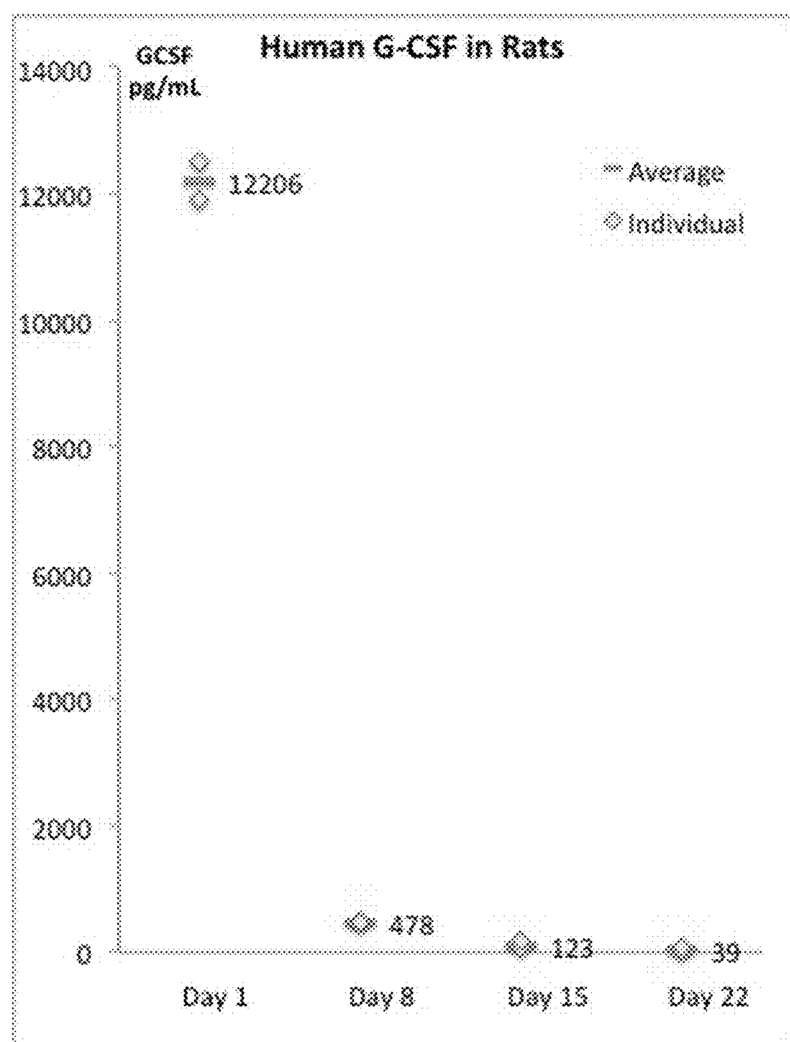
FIG. 18 shows results from Example 3, wherein it was shown that one sequential IV injection of cationic liposomes followed by a CPG-free, human G-CSF DNA vector produces supra-therapeutic human G-CSF serum protein, WBC and ANC levels, with normal ALT (alanine aminotransferase) and AST (aspartate aminotransferase) in rats.

In this Example, 250 gm Sprague-Dawley female rats #22 and 23 were sequentially injected with 6000 nmol of DOTAP SUV then 300 ug of a CPG-free plasmid vector containing an EF1-driven hG-CSF DNA vector. Serum levels of human G-CSF protein, WBC and absolute neutrophil counts (ANC) were assessed at 7-day intervals following injection. Serum ALT and AST levels were assessed at day 1 only. All were assessed by the UC Davis Comparative Pathology lab. As shown in FIG. 18, and Table 3 below, supra-therapeutic levels of hG-CSF protein, as well as significantly elevated WBC and ANC, were produced in EF1-huG-CSF injected rats for at least 22 days following a single IV injection. ALT and AST measured at day 1 after injection were comparable to background control levels in un-injected rats.

TABLE 3

| WBC | Day 1 | Day 8 | Day 15 | Day 22 | | | ALT | Day 1 | | |
|---|---|---|---|---|---|---|---|---|---|---|
| #22 | 6.56 | 27.36 | 23.68 | 27.20 | Ctrl | 4.57 | #22 | 30.30 | Ctrl | 12-67 |
| #23 | 11.04 | 15.74 | 12.90 | 20.08 | SEM | 0.27 | #23 | 29.40 | | |
| **ANC** | **Day 1** | **Day 8** | **Day 15** | **Day 22** | | | **AST** | **Day 1** | | |
| #22 | 4.99 | 17.31 | 12.32 | 15.69 | Ctrl | 1.39 | #22 | 89.80 | Ctrl | 14-113 |
| #23 | 5.07 | 8.07 | 6.68 | 10.57 | SEM | 0.13 | #23 | 74.00 | | |

Example 4

DPTAP Liposomes

Figure 19:
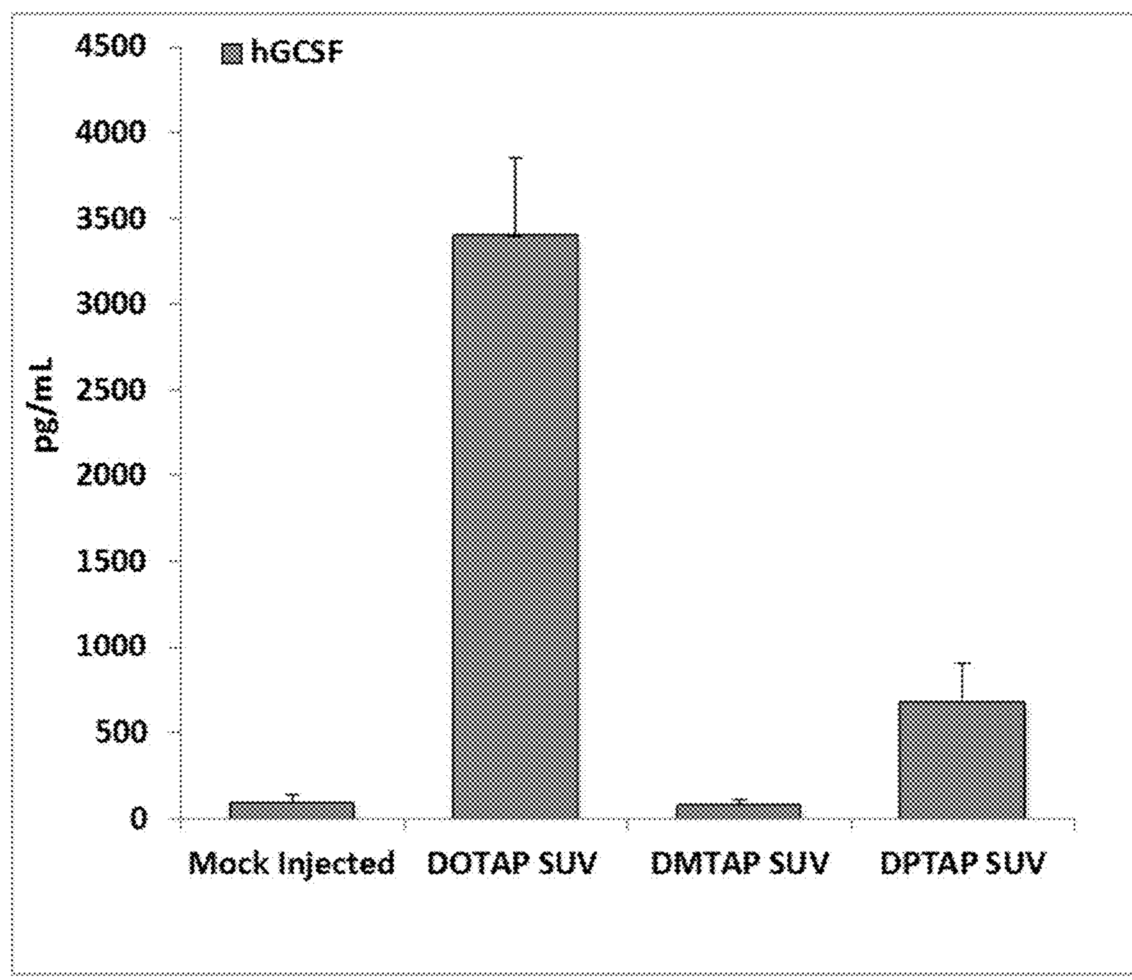
FIG. 19 shows results from Example 3, where it was shown that cationic liposomes generated from DPTAP mediate in vivo transfection.

In this Example, three mice were injected per group. Each mouse received a single IV injection of 900 nmoles of DOTAP, DMTAP, or DPTAP (1,2-dipalmitoyl 3-trimethylammonium propane) SUV liposomes followed two minutes later by a single IV injection of 70 ug of an EF-1 plasmid DNA vector encoding hG-CSF. Serum levels of hG-CSF were determined by ELISA 24 hours following injection. FIG. 19 shows that HuG-CSF protein was present in serum from mice treated with DOTAP or DPTAP but not DMTAP. These data indicate that multiple cationic lipids can mediate transfection in vivo, and that level of protein production can be controlled by selection of the lipid carrier.

Example 5

Toxicity Resolves Within 48 Hours

Figure 20:
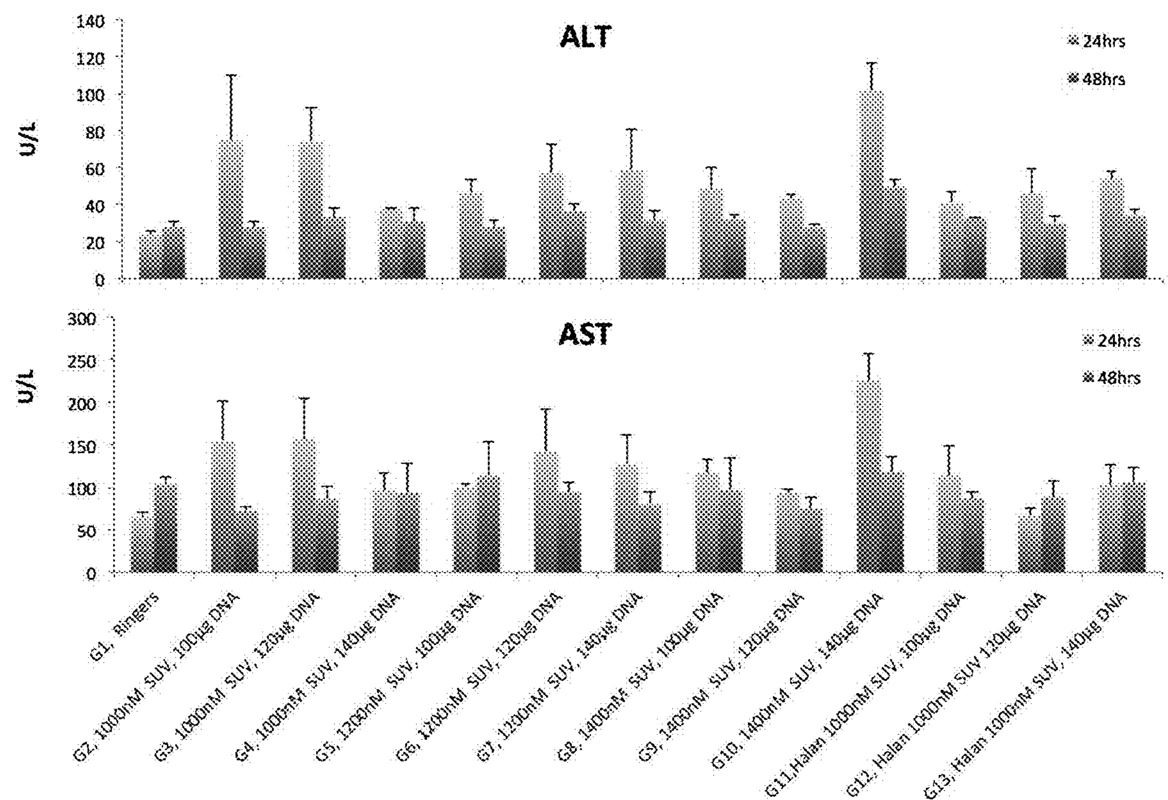
FIG. 20 shows that toxicity as measured by serum levels of alanine aminotransferase (ALT) and aspartate aminotransferase (AST) are elevated 2 to 5 fold at 24 hrs and return to control levels by 48 hours after sequential injection of cationic liposomes then plasmid DNA.

In this Example, three mice were injected per group. Mice were purchased from Charles River Labs. Each mouse received a single IV injection of 1000 nmoles, 1200 nmoles, or 1400 nmoles of DOTAP SUV liposomes as indicated, followed two minutes later by a single IV injection of 100 μg, 120 μg, or 140 μg of a CPG-free EF-1 driven plasmid DNA vector encoding luciferase. Serum was collected at 24 hrs or 48 hrs after injection. ALT and AST measurements were assayed at the UC Davis Comparative Pathology lab. As shown in FIG. 20, at 24 hours following sequential injection, serum levels of ALT and AST were elevated from two to five fold in all lipid then DNA groups. At 48 hours, serum ALT and AST levels returned to control (background) levels (shown by the mock-injected group). These data indicate that toxicity as measured by ALT/AST is acute (present within 24 hrs of injection) and transient (gone by 48 hrs).

Example 6

Liposomes with DexP

Figure 21:
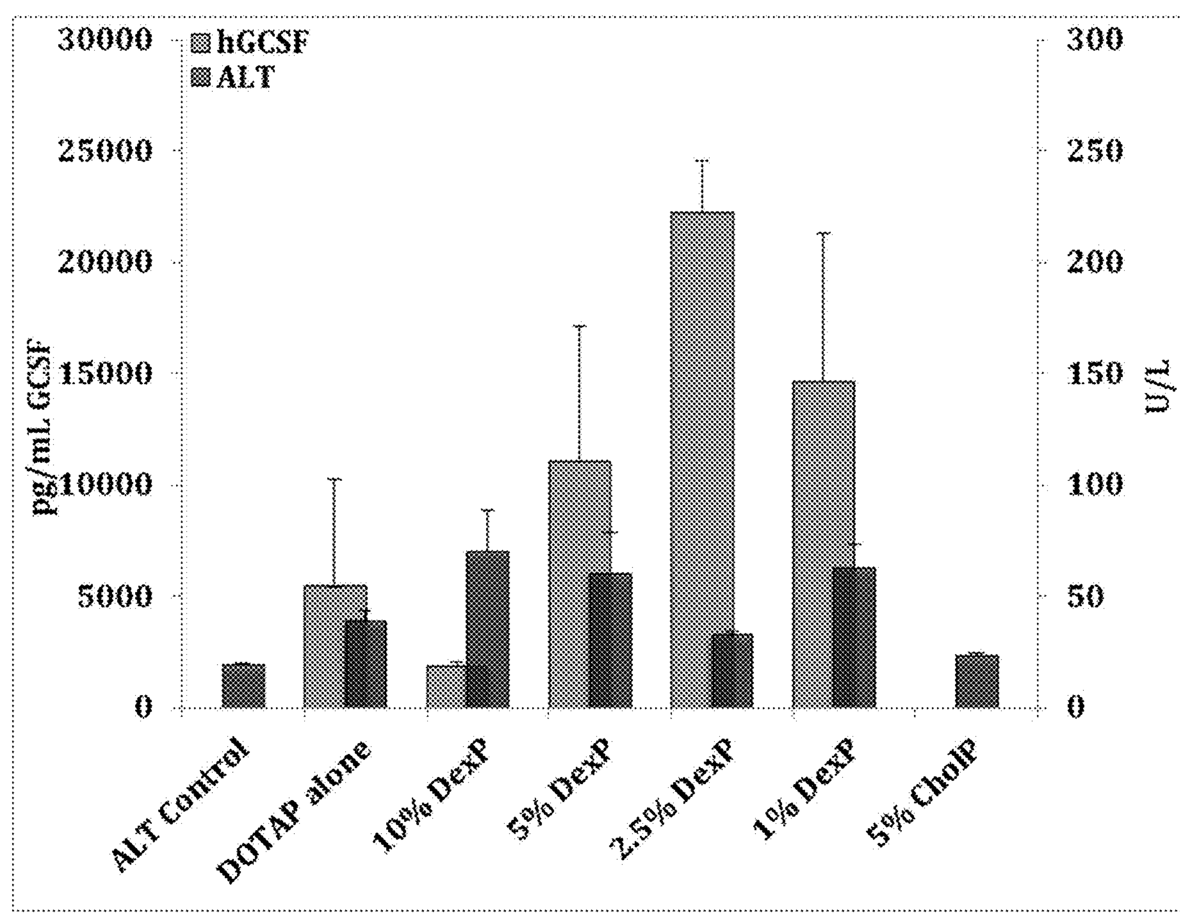
FIG. 21 shows incorporation of 2.5 mole % dexamethsone palmitate (DexP) into cationic DOTAP liposomes increases expression of hG-CSF at 24 hours after sequential IV injection while simultaneously reducing toxicity, as measured by ALT levels to close to background levels.

In this Example, three mice were injected per group. Each mouse received a single IV injection of 900 nmoles of either pure DOTAP SUV liposomes or each mouse received a single IV injection of 900 nmoles of either pure DOTAP SUV liposomes or liposomes containing indicated mole % s of dexamethasone covalently linked to palmitate (DexP) incorporated into the liposome bilayer. Incorporation of 5% cholesteryl palmitate (CholP) into the liposome bilayer served as a control. This was followed two minutes later by a single IV injection of 90 ug of plasmid DNA encoding hG-CSF. Serum levels of hG-CSF were determined by ELISA 24 hours following injection and ALT measurements were assayed at the UC Davis Comparative Pathology lab. As shown in FIG. 21, at 24 hours following sequential injection, toxicity as measured by ALT levels is 2-3 fold higher than seen in animals that were mock injected with lactated ringer's solution only (ALT Control). Incorporation of 2.5% dexamethasone palmitate (DexP) into the liposome bilayer produced a dual effect of increasing peak expression of hG-CSF as well as reducing ALT levels to within 1.5 fold of background (normal) levels at 24 hours.

Example 7

DexP Reduces Toxicity and Increases Expression

Figure 22:
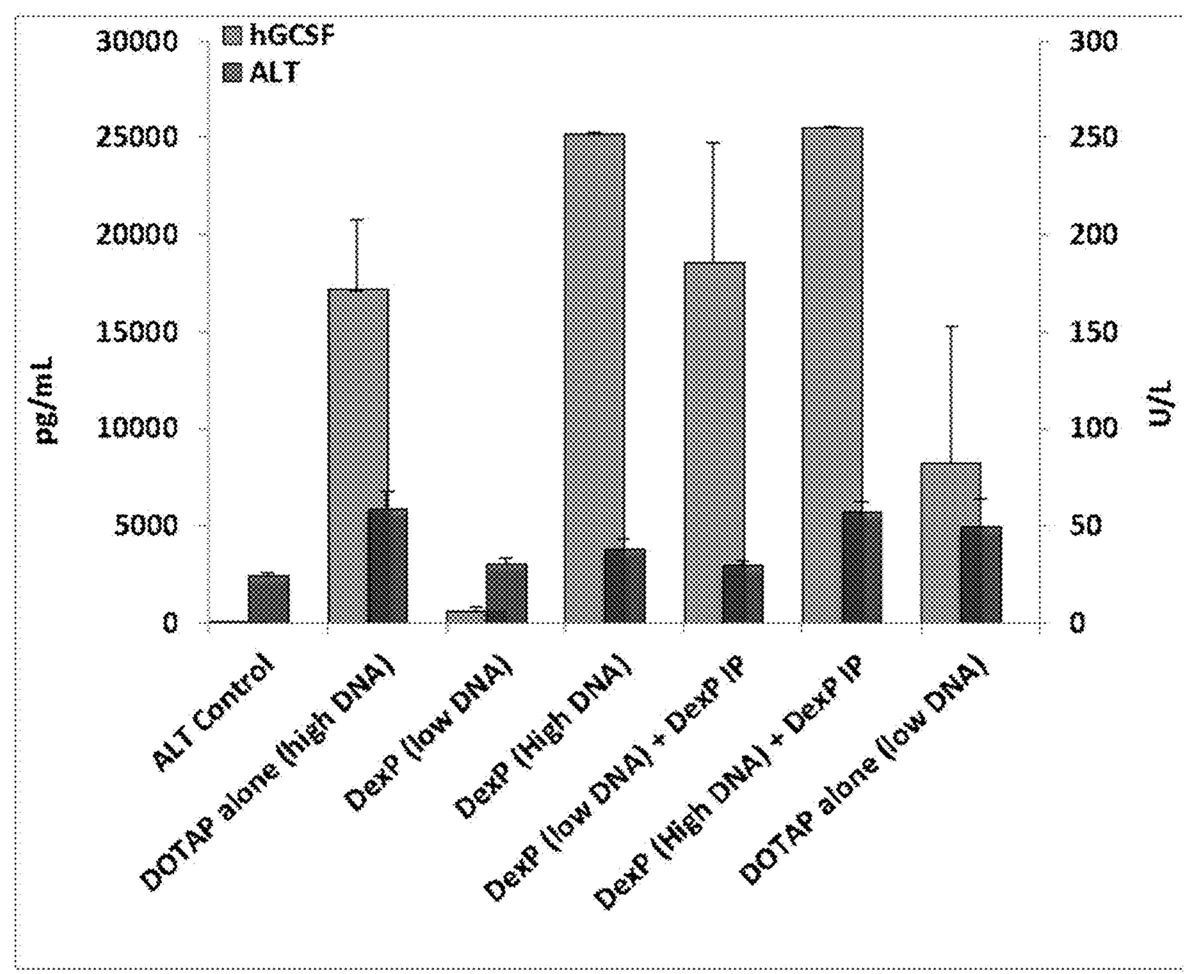
FIG. 22 shows that IV injection of DOTAP liposomes containing 2.5% dexamethasone palmitate reduces toxicity, as measured by ALT levels to background levels while significantly increasing human G-CSF protein levels.

In this Example, three mice were injected per group. Each mouse received a single IV injection of 900 nmoles of either pure DOTAP SUV liposomes or liposomes containing 2.5 mole % of dexamethasone covalently linked to palmitate (DexP) incorporated into the liposome bilayer of DOTAP liposomes. This was followed two minutes later by a single IV injection of either 130 ug (high) or 40 ug (low) of an EF-1 driven plasmid DNA vector encoding hG-CSF. Two groups were treated two hours prior to IV injection with an IP injection of 1 umole of dexamethasone palmitate. Serum levels of hG-CSF were determined by ELISA 24 hours following injection and ALT measurements were assayed at 24 hours by the UC Davis Comparative Pathology lab. As shown in FIG. 22, sequential injection of 130 ug of DNA produced significantly higher hG-CSF protein levels than 40 ug of DNA 24 hours later. Inclusion of 2.5 mole % dexamethasone palmitate in the liposomes at either DNA dose further increased hG-CSF protein levels. In addition, incorporation of dexamethasone palmitate in liposomes reduced ALT levels to within 1.5 fold of background (normal) levels, even at the much higher DNA dose.

Example 8

Pre and Post Dex Injection

Figure 23:
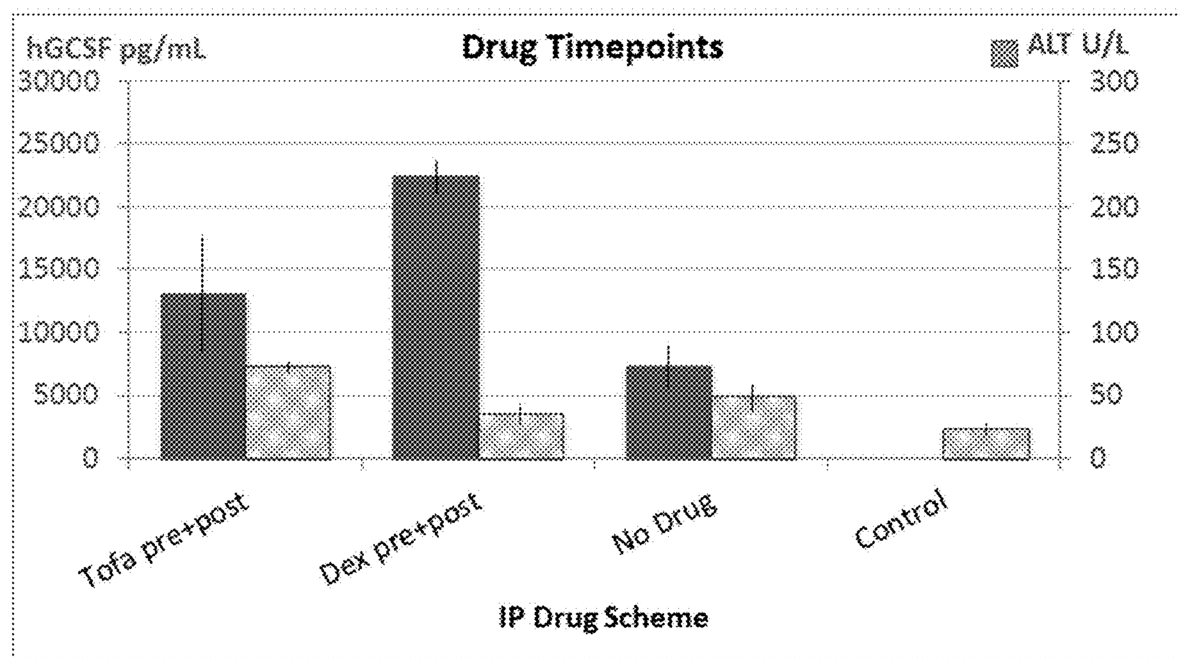
FIG. 23 shows pre- and post-injection of Dexamethasone significantly increases hG-CSF protein levels while reducing toxicity, as measured by ALT levels to close to background levels.

In this Example, mice were pre-injected IP with 15 mg/kg of Tofacitinib or 40 mg/kg of Dexamethasone, followed 2 hours later by sequential IV injections of 900 nmol DOTAP SUV, then 70 ug of a CPG-free, EF-1 driven hG-CSF plasmid vector. Another IP injection of Tofacitinib or Dexamethasone was administered 2 hours after injection of DNA. As shown in FIG. 23, administration of dexamethasone prior to, as well as following, sequential cationic liposome then DNA injection both significantly increased HuG-CSF protein levels while concurrently reducing toxicity within 1.5 fold of background (normal) levels. In contrast, pre- and post-injection of the immunosuppressive agent Tofacitinib did neither.

Example 9

Lipid to DNA Ratio

Figure 24:
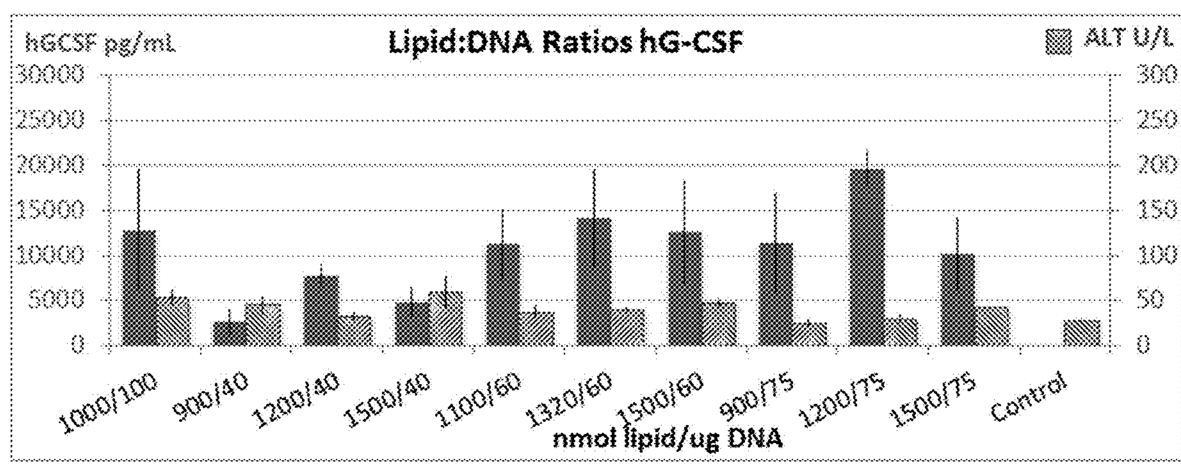
FIG. 24 shows manipulating Lipid:DNA Ratios increases hG-CSF levels while reducing toxicity, as measured by ALT levels to background levels.

In this Example, three mice per group were given IV injections of 900, 1000, 1200, or 1500 nmols of DOTAP SUV liposomes containing 2.5 mole % of dexamethasone covalently linked to palmitate (DexP) incorporated into the liposome bilayer of DOTAP liposomes, suspended in Lactated Ringer's (LR) to a final volume of 100 uL per injection, followed 2 minutes later by 40, 60, or 75 ug of a CPG-free, EF-1 driven, hG-CSF plasmid vector at 100 μL per injection. Mock-injected mice received LR only without lipid or DNA. Serum levels of hG-CSF protein and ALT were assayed 24 hours later. As shown in FIG. 24, hG-CSF protein and ALT levels of mice sequentially injected with DOTAP SUV lipid to plasmid DNA (nmole lipid:mg DNA) ratios lower than 26:1 produced significantly higher hG-CSF protein levels while preventing toxicity, as documented by producing ALT levels either within 1.5 fold of or equal to background (normal) levels in control mice that received neither lipid nor DNA injection.

Example 10

Rituximab Expression

Figure 25:
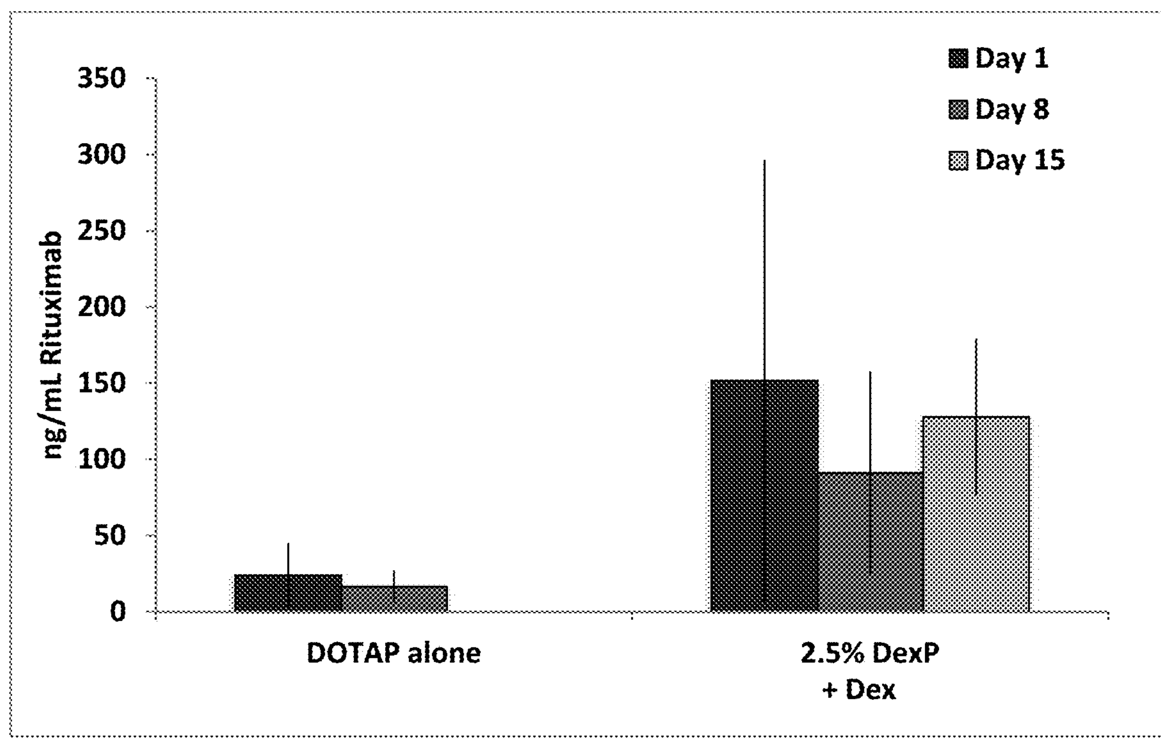
FIG. 25 shows that IP pre-injection of dexamethasone, followed by 2.5 mole % dexamethsone palmitate in cationic DOTAP liposomes then a dual cassette, single plasmid DNA vector encoding Rituximab significantly increases serum Rituximab levels over time in mice.

In this Example, three mice were injected per group. Each mouse received a single IV injection of 1000 nmoles of either pure DOTAP cationic liposomes or liposomes containing 2.5 mole % of dexamethasone covalently linked to palmitate (DexP) incorporated into the liposome bilayer of DOTAP liposomes. This was followed two minutes later by a single IV injection of 100 ug of a dual cassette, single plasmid DNA vector encoding the Rituximab heavy and light chains (see constructs in FIGS. 36, 40, and 41). Serum Rituximab levels were determined by ELISA 24 hours following injection and then at 7-day intervals. Mice were bled and serum isolated as for G-CSF. Rituximab levels were measured using an Immunoguide ELISA obtained from Eagle Biosciences, and performed according to instructions. As shown in FIG. 25, IP dexamethasone pretreatment plus incorporation of 2.5 mole % dexamethasone palmitate in DOTAP liposomes increases serum Rituximab levels by more than five fold for at least three weeks after injection.

Example 11

Rituximab Expression

In this Example, three mice were injected per group. Each mouse received a single IV injection of 1000 nmoles of either pure DOTAP cationic liposomes or liposomes containing 2.5 mole % of dexamethasone covalently linked to palmitate (DexP) incorporated into the liposome bilayer of DOTAP liposomes. This was followed two minutes later by a single IV injection of 100 ug of an EF-1-driven, dual cassette, single plasmid DNA vector encoding Rituximab (see constructs in FIGS. 36, 40, and 41). One group was treated two hours prior to IV injection with an IP injection of 40 mg/kg dexamethasone (Dex) and 1000 nmoles the neutral lipid (NL), DMPC. Serum Rituximab levels injected mice were determined by ELISA 24 hours following injection and at 7-day intervals thereafter. As shown in FIG. 26, all mice produced significant levels of serum Rituximab protein for at least 12 weeks following one injection. Mice receiving the combination of Dex, DexP and NL produced significantly higher serum Rituximab levels over time. These data show that a single sequential injection of a dual cassette Rituximab plasmid DNA vector can produce significant levels of serum Rituximab protein in animals for greater than 90 days.

Example 12

Dual Cassette, Single Plasmid Rituximab Expression

In this Example, Raji cells (1 million/sample) were incubated with mouse serum samples or recombinant Rituximab (50 ng/ml) for 1 hr at 4C, in FACS binding buffer containing EDTA and 0.5% BSA. Following washes, samples were incubated with fluorescently labeled secondary antibody (anti-human IgG-PE) for 30 min, washed and analyzed using an Accuri flow cytometer. Between 3500-5000 events were recorded for each sample. The experiment was repeated twice with similar results.

Figure 27:
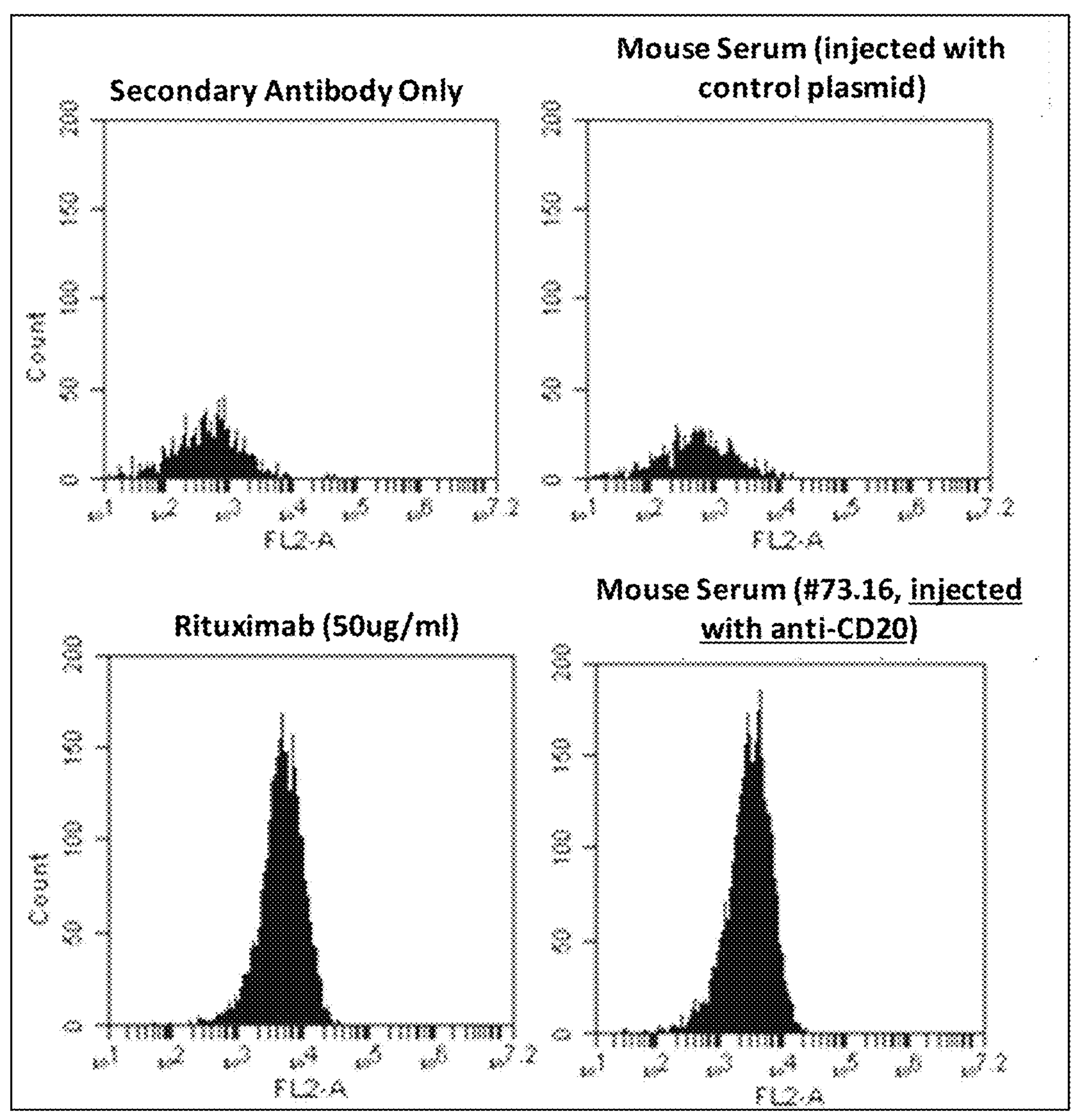
FIG. 27 shows mouse serum tested at 6 weeks following IV sequential injection of a dual cassette, single plasmid Rituximab DNA vector binds target CD20+ human B lymphoma (Raji) cells similarly to recombinant Rituximab protein.

FIG. 27 shows a FACS plots display fluorescence intensity for four experimental conditions. The upper panels show samples containing mouse serum from control (HuG-CSF) DNA plasmid vector injected mice or secondary antibody alone, which display low, background levels of fluorescence in the PE channel (~300). The lower two panels show recombinant Rituximab protein (left panel) and mouse serum following Rituximab plasmid DNA vector administration (right panel). Both samples show fluorescence intensities over 10 fold higher than the background as shown in Table 4 below, demonstrating that Rituximab present in the mouse serum binds to target CD20-expressing human Raji B cells to an extent similar to recombinant Rituximab protein. Thus, the Rituximab present in mouse serum six weeks after injection of a dual cassette, single plasmid Rituximab DNA vector binds CD20+ target human B cells in a fully functional manner.

TABLE 4

| Sample designation | Mean Fluorescence Intensity |
|---|---|
| Secondary antibody alone | 331.86 |
| Mouse Serum (injected with control plasmid) | 279.32 |
| Recombinant Rituximab (50 ug/ml) | 5781.87 |
| Mouse Serum (injected with anti-CD20 plasmid) | 3532.40 |

Example 13

Functional Rituximab is Expressed

Figure 28:
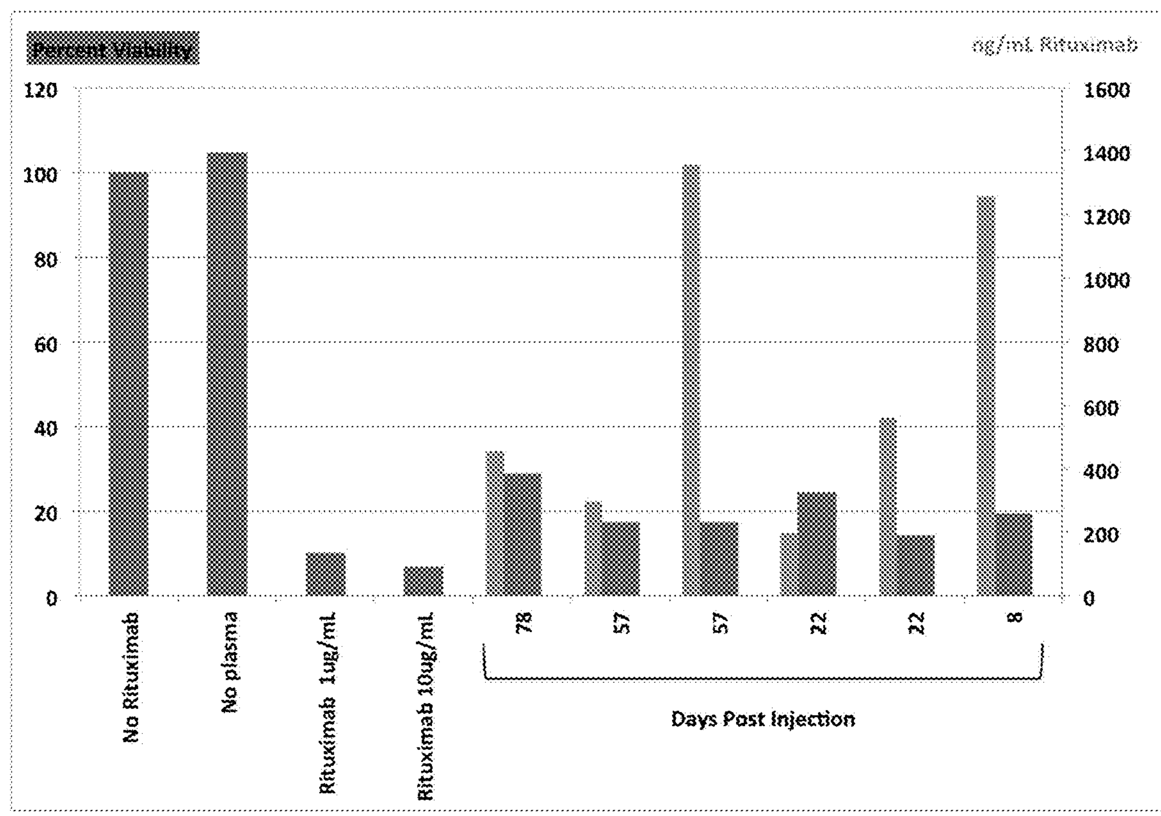
FIG. 28 Rituximab protein in serum from Rituximab DNA vector-injected mice induces lysis of Raji CD20+ human B cells at levels similar to recombinant Rituximab.

In this Example, Raji cells ($5\times10^4$ cells/well) were plated in 96 well plates using RPMI+10% FBS medium. Next day cells were incubated with Rituximab (1, 10 ug/ml) or mouse serum samples (20 μl/well) for 1 hour at room temperature. Twenty ul of pooled normal human plasma (Innovative Research) was then added to all wells (except the Rituximab control condition) and the plates incubated for another 12 h at 37C. Cell viability was measured using the Promega Cell titer glo reagent according to the manufacturer's instructions. In FIG. 28, values are shown as percentage change from the control conditions in which serum from mice injected with a huG-CSF DNA plasmid DNA vector was used. Individual mouse sera were tested from five different mouse groups that received a single sequential injection of a dual cassette, single plasmid Rituximab DNA vector from 8 to 78 days prior to serum collection.

Results of this Example are shown in FIG. 28. Sera from mice previously injected with a dual cassette, single plasmid Rituximab DNA vector were analyzed first by ELISA to quantitate serum Rituximab concentrations. Adding these Rituximab-containing sera in a cell lysis assay then showed that they lyse CD-20+ human Raji B cells in a manner comparable to recombinant Rituximab (Invivogen). Moreover, functional serum Rituximab protein with documented lytic activity was isolated from animals across five separate injection experiments over a eleven-week period, demonstrating its reproducible lytic efficacy over time.

Example 14

Enhanced Expression of Rituximab

Figure 36:
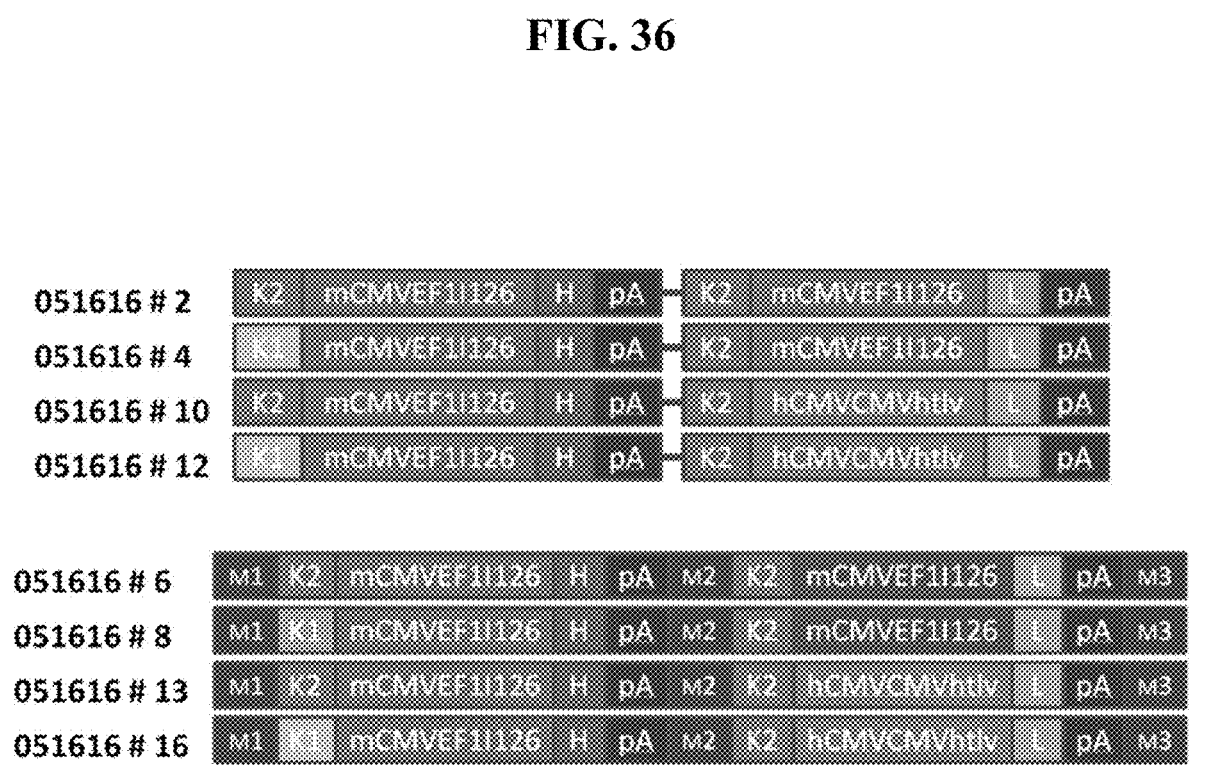

In this Example, two, 250 gm Sprague-Dawley female rats per group were were first pre-injected with 40 mg/kg dexamethasone, then sequentially injected with 4400 nmol of DOTAP SUV liposomes containing 2.5 mole % of dexamethasone covalently linked to palmitate (DexP) incorporated into the liposome bilayer, with or without 4400 nmol of neutral DMPC lipid, then 360 μg of a dual cassette, single plasmid DNA vector containing an EF1-driven Rituximab cDNA (see constructs in FIGS. 36, 40, and 41). Serum levels of human Rituximab protein were assessed at 7-day intervals following injection. FIG. 29 shows significantly higher levels of serum Rituximab protein were produced in rats also receiving neutral lipid for at least 15 days following a single IV injection.

Example 15

Codon-Optimized Rituximab Expression

Figure 30:
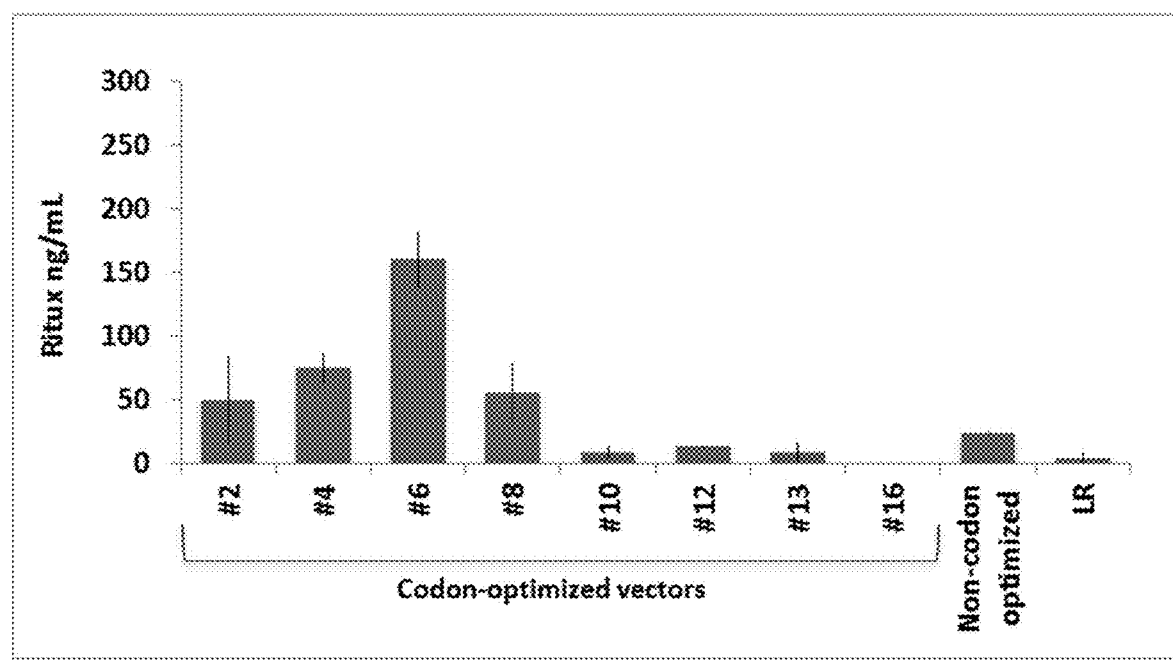
FIG. 30 shows codon-optimization of Rituximab dual cassette, single plasmid DNA vectors further increases serum Rituximab levels 24 hours after sequential IV injection.

In this Example, three mice were injected per group. Each mouse received a single IV injection of 1000 nmoles of liposomes containing 2.5 mole % of dexamethasone covalently linked to palmitate (DexP) incorporated into the liposome bilayer of DOTAP liposomes. This was followed two minutes later by a single IV injection of 100 ug of dual cassette, single plasmid EF-1-driven DNA vector encoding Rituximab (see constructs in FIGS. 36, 42, and 43). Numbered plasmids (in FIG. 30) were codon-optimized versions of the original, CpG-free but not codon optimized Rituximab DNA sequence. Serum levels of Rituximab were determined by ELISA 24 hours following injection. FIG. 30 shows that at 24 hours following sequential injection, codon-optimized DMA vector 6 produced significantly higher levels of serum Rituximab protein than non-codon optimized rituximab DNA vectors.

Example 16

Codon-Optimized Rituximab Expression

Figure 31:
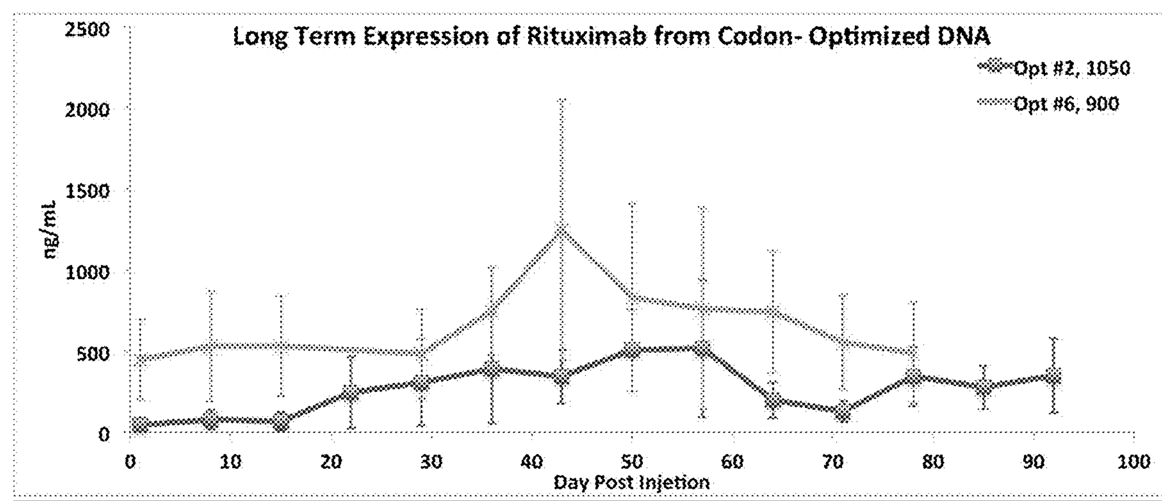
FIG. 31 shows that one sequential, IV cationic liposome injection of codon-optimized dual cassette, single plasmid Rituximab DNA vectors produces extended serum Rituximab levels.

In this Example, three mice were injected per group. Each mouse received a single IV injection of DOTAP cationic liposomes (900 nmoles or 1050 nmoles as indicated) containing 2.5 mole % of dexamethasone covalently linked to palmitate (DexP) incorporated into the liposome bilayer. This was followed two minutes later by a single IV injection of 75 ug of a dual cassette, codon-optimized single plasmid DNA encoding Rituximab (see constructs in FIGS. 36, 42, and 43). Both groups were treated two hours prior to IV injection with an IP injection of 40 mg/kg dexamethasone. Serum levels of Rituximab were determined by ELISA 24 hours following injection and at 7-day intervals thereafter. FIG. 31 shows that one sequential IV injection of codon-optimized dual cassette, single plasmid Rituximab DNA vectors produces extended serum Rituximab levels for at least the next 60 days. Serum Rituximab levels rise over time after a single IV sequential injection.

Example 17

Valproic Acid and Theophylline Increase Protein Expression

Figure 32:
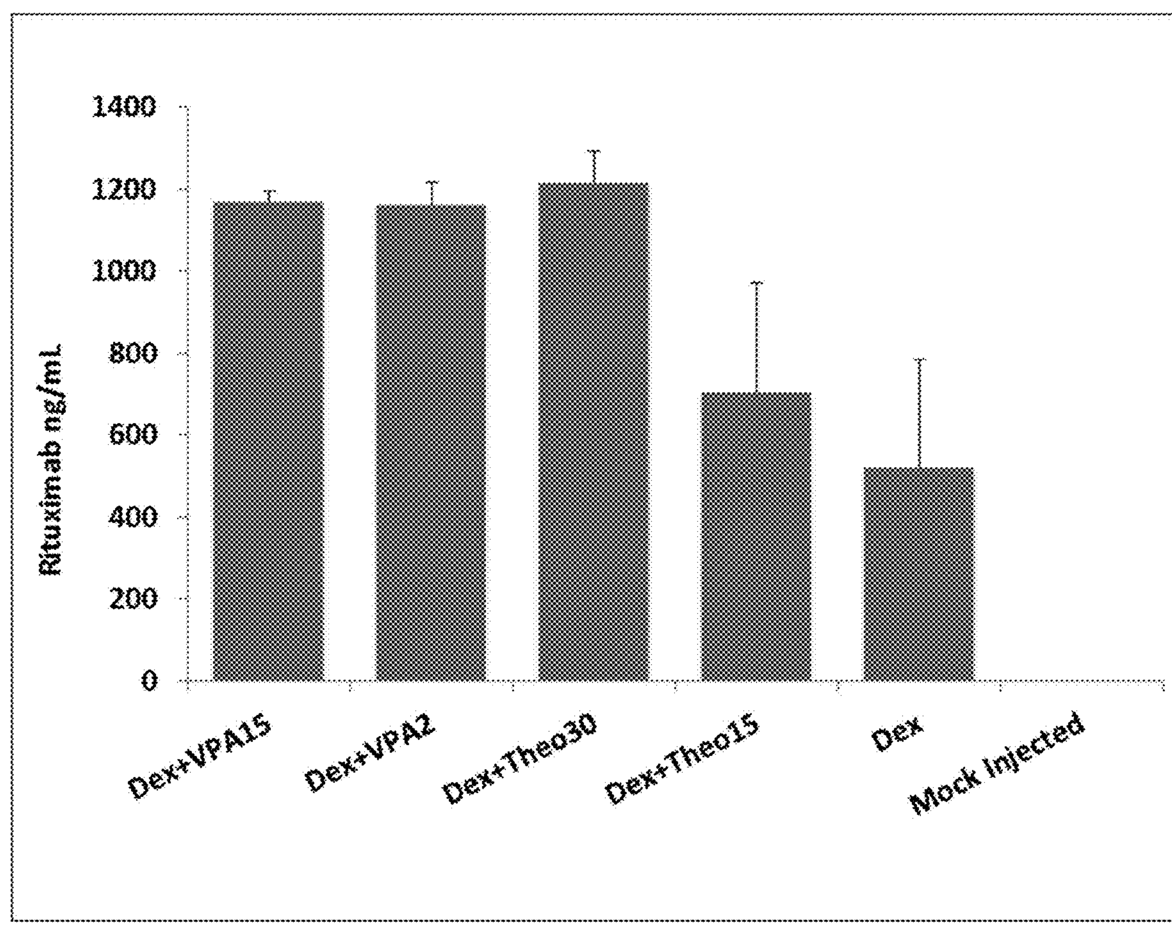
FIG. 32 shows that pre-injection of selected drugs significantly increases serum Rituximab levels produced by sequential IV, cationic liposome injection of a codon-optimized dual cassette, single plasmid Rituximab DNA vector.

In this Example, three mice were injected per group. Each mouse received a single IV injection of 1050 nmoles of liposomes containing 2.5 mole % of dexamethasone covalently linked to palmitate (DexP) incorporated into the liposome bilayer of DOTAP liposomes. This was followed two minutes later by a single IV injection of 75 ug of dual cassette plasmid DNA encoding Rituximab. All groups were treated two hours prior to IV injection with an IP injection of 40 mg/kg dexamethasone. Where indicated in FIG. 32, animals were also pretreated by IP injection of 15 mg/kg Valproic Acid (VPA), 2 mg/kg VPA, 30 mg/kg Theophylline (Theo) or 15 mg/kg Theo. Serum Rituximab levels were determined by ELISA 24 hours following injection. FIG. 32 shows serum Rituximab levels produced were significantly increased by pre-treatment with the drugs Valproic Acid or Theophylline, thus providing a framework for further enhancing protein levels without altering the dose of lipid or DNA.

Example 18

Dual or Single Cassette Rituximab Expression

Figure 33:
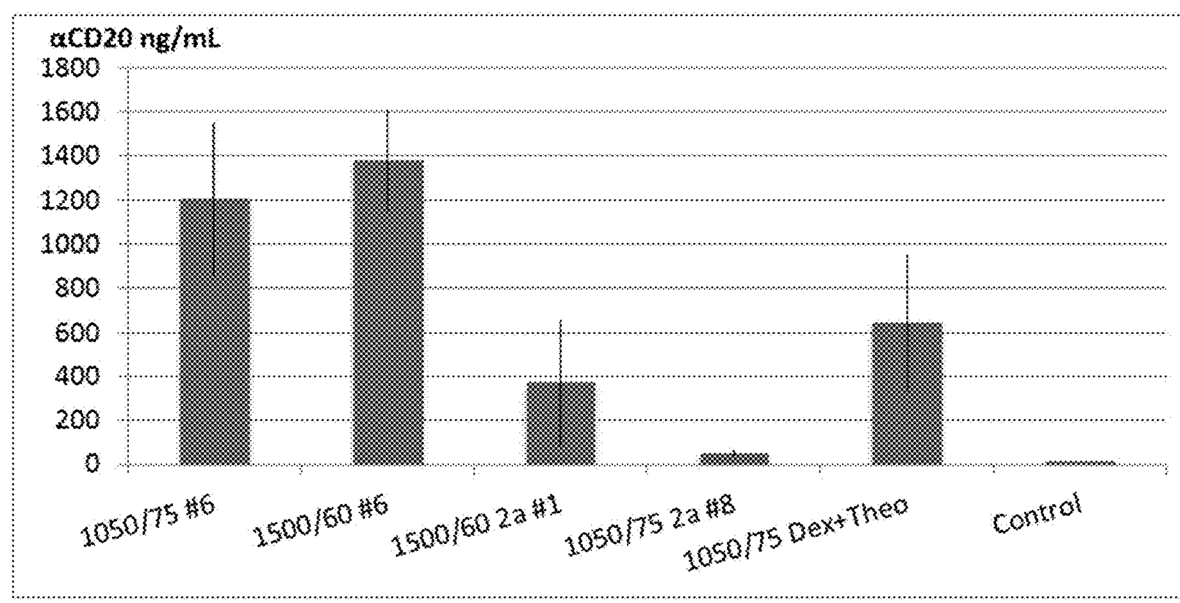
FIG. 33 shows sequential IV injection of a single cassette DNA vector encoding the Rituximab heavy and light chains separated by a 2A self cleaving peptide sequence produces significant serum Rituximab protein levels.
Figure 37:
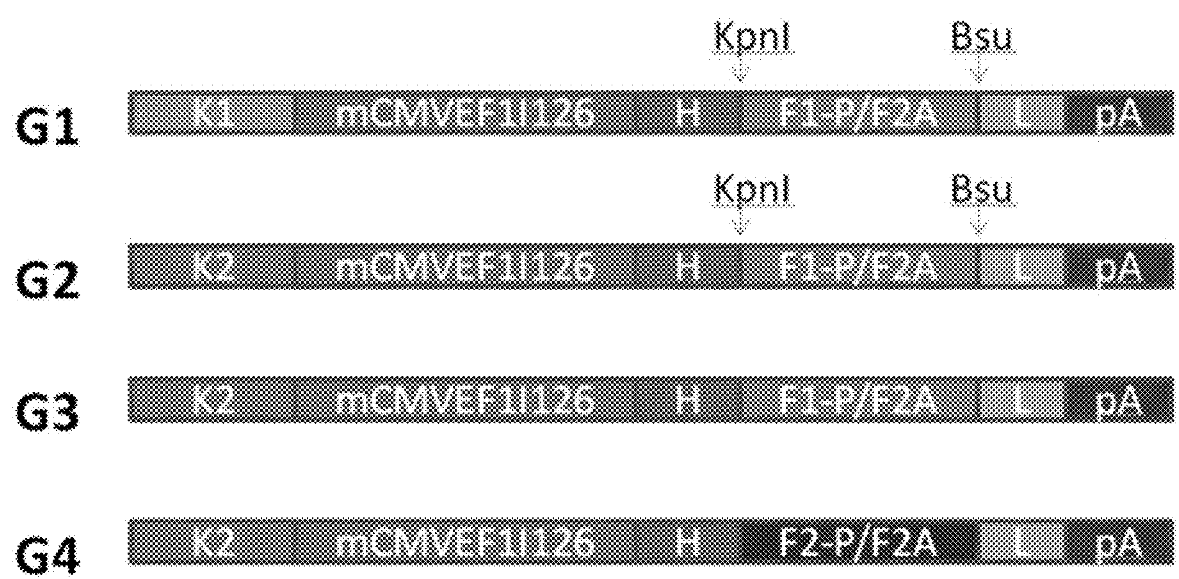
FIG. 37 shows the arrangement of the Rituximab (anti-CD20) single (bisicontronic) plasmid used in the Examples. In this figure, the following abbreviations apply: K: Kozak Sequence (K1:AAGCTTTCC K2, SEQ ID NO:3; AAGCCACC, SEQ ID NO:4); Enhancer: mCMV or hCMV; Promoter: CMV or EF1; 5'UTR: 1126 or htlv H: Chimeric Heavy Chain cDNA; L: Chimeric Light Chain cDNA; F: Furin (F1: RHQR; F2: RAKR); 2A Peptide: P2A or F2A; and pA: polyA.

In this Example, mice were pre-injected with 40 mg/kg Dexamethasone IP. Two hours later, they were sequentially injected with either 1050 or 1500 nmols of DOTAP SUV liposomes containing 2.5 mole % of dexamethasone covalently linked to palmitate (DexP) incorporated into the liposome bilayer, followed by 60 μg or 75 μg of plasmid DNA. Plasmid DNA constructs injected were either codon optimized, double-cassette, single plasmid DNA vectors (see constructs in FIGS. 36, 42, and 43) or codon optimized single-cassette plasmids (see constructs in FIGS. 36, 37, and 39) containing Rituximab heavy and light chain sequences separated by a 2A self-cleaving peptide DNA sequence. Serum Rituximab levels were determined by ELISA 24 hours following injection. FIG. 33 shows that at 24 hours following sequential injection, mice that received 2A peptide containing single cassette vectors encoding Rituximab produced serum levels approaching 400 ng/ml, approximately one-third the level produced by the dual cassette vector. Thus, significant Rituximab serum levels can be produced by either dual- or single-cassette, 2A peptide-containing DNA vectors.

Example 19

Lipid to DNA Ratio and Rituximab Expression

Figure 34:
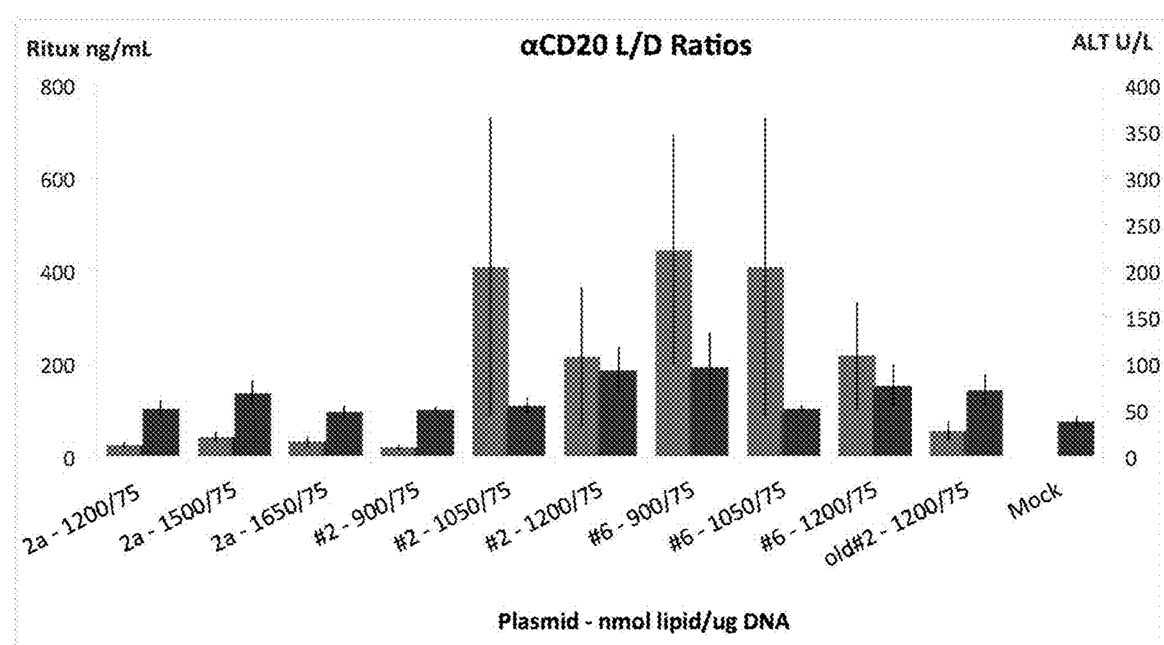
FIG. 34 shows that manipulating Lipid:DNA Ratios increases serum Rituximab levels while reducing toxicity, as measured by ALT levels to close to background levels.

In this Example, three mice per group were given IV injections of 900, 1050, 1200, 1500 or 1650 nmols of DOTAP SUV liposomes containing 2.5 mole % of dexamethasone covalently linked to palmitate (DexP) incorporated into the liposome bilayer, suspended in Lactated Ringer's (LR) to a final volume of 100 uL per injection, followed 2 minutes later by 75 ug of a CPG-free, dual cassette, single plasmid Rituximab vector at 100 uL per injection. Mock-injected mice received LR only without lipid or DNA. Serum levels of Rituximab protein and ALT were assayed 24 hrs later. FIG. 34 shows Rituximab protein and ALT levels of mice sequentially injected with DOTAP SUV lipid to plasmid DNA (nmole lipid:mg DNA) ratios lower than 15:1 produced significantly higher Rituximab protein levels while producing serum ALT levels within 1.5 fold of background (normal) ALT levels in control mice that received neither lipid nor DNA injection.

Example 20

Factor IX Expression with Valproic Acid or Theophylline

Figure 35:
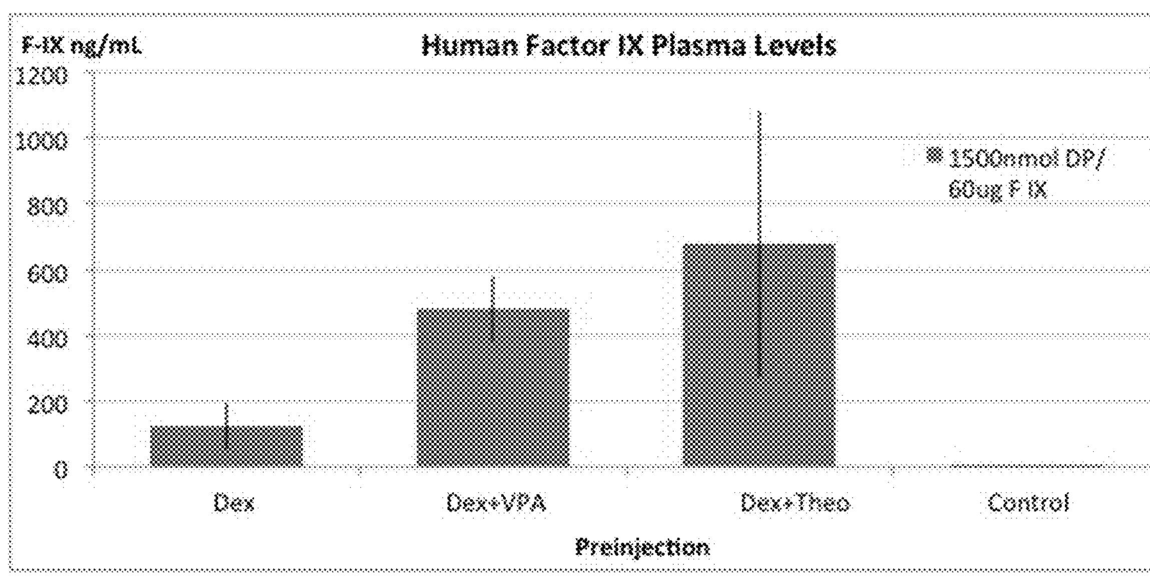
FIG. 35 shows that pretreatment with either valproic acid or theophylline significantly increases serum human factor nine levels produced by sequential IV, cationic liposome injection of a codon-optimized, EF-1-driven plasmid vector encoding a human factor IX cDNA.
Figure 38:
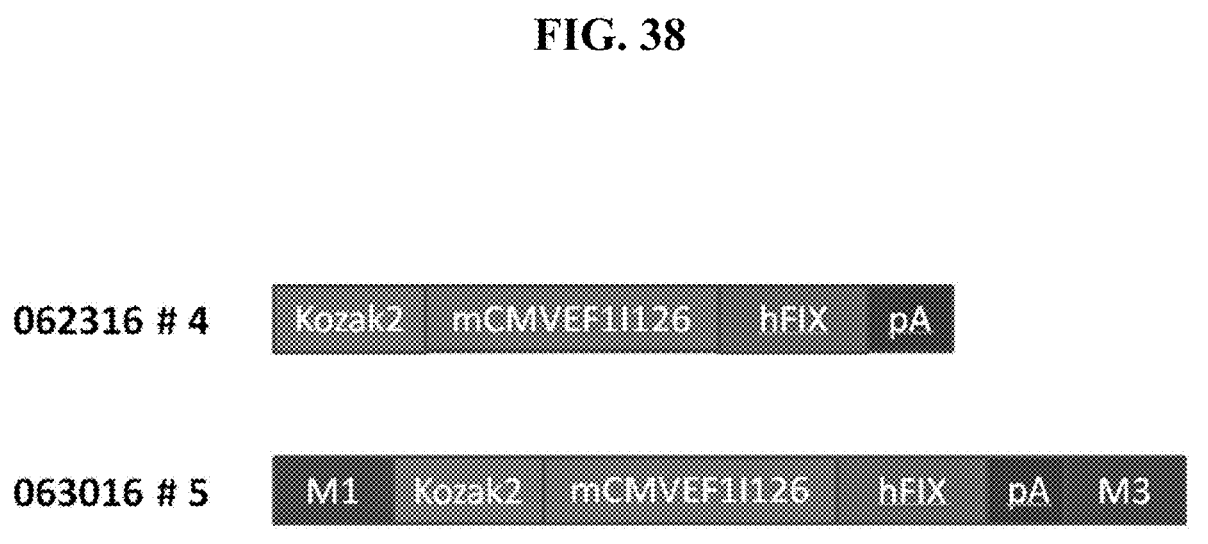

In this Example, three mice were injected per group. Each mouse received a single IV injection of 1500 nmoles of DOTAP SUV liposomes containing 2.5 mole % of dexamethasone covalently linked to palmitate (DexP) incorporated into the liposome bilayer. This was followed two minutes later by a single IV injection of 60 ug of a codon optimized, EF-1-driven single cassette DNA vector encoding the human factor IX cDNA (see constructs in FIGS. 38 and 44). All groups were treated two hours prior to IV injection with an IP injection of 40 mg/kg dexamethasone. Where indicated, animals were also pretreated by IP injection of 2 mg/kg Valproic Acid (VPA) or 30 mg/kg Theophylline (Theo). Serum human factor IX levels were determined by ELISA 24 hours following injection. Each mouse was bled as for G-CSF. Blood was collected into tubes containing Potassium EDTA or Sodium Citrate to prevent coagulation and centrifuged to obtain plasma. An AssayPro ELISA specific to human Factor IX was used according to manufacturer's instructions to measure Factor IX expression. FIG. 35 shows serum human factor IX levels produced at 24 hrs were significantly higher in mice receiving the human factor IX DNA vector plus pre-treatment with either Valproic Acid or Theophylline.

Example 21

Size Determination of Liposomes

In this Example, the sizes of various liposomes were determined. In particular, the liposomes in Table 5 were prepared in 5% w/w glucose, and the size was determined using quasi elastic laser light scattering. The Z-Average particle size of these DOTAP liposomes is shown in Table 5.

TABLE 5

| Liposome Type | Z-Average Particle Size (nm) |
|---|---|
| DOTAP Multilamellar Liposomes (MLV) | 339 |
| DOTAP 0.1 micron Extruded MLV | 146 |
| DOTAP Sonicated Liposomes (SUV) | 74 |

All publications and patents mentioned in the present application are herein incorporated by reference. Various modification and variation of the described methods and compositions of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the following claims.

We claim:

1. A method of expressing an antibody light chain and/or heavy chain in a subject comprising:

a) administering intravenously a first composition to a subject, wherein said first composition comprises a first amount of polycationic structures, and wherein said first composition is free, or essentially free, of nucleic acid molecules; and b) administering intravenously a second composition to said subject within about 300 minutes of administering said first composition, wherein said second composition comprises non-viral expression vectors, wherein said non-viral expression vectors are CpG-free or CpG-reduced, wherein said non-viral expression vectors each comprise a first nucleic acid sequence encoding an antibody light chain and/or heavy chain, wherein the ratio of said first amount of said polycationic structures to said non-viral expression vectors is 5:1 to 25:1, and wherein, as a result of said administering said first composition and said administering said second composition, said antibody light chain and/or heavy chain is expressed in said subject at a level of at least 50 pg/ml in serum for at least 7 consecutive days; and c) administering intravenously a drug agent, in said first and/or second composition, or present in a third composition, wherein said drug agent increases or decreases said expression level of said antibody light chain and/or heavy chain and/or the length of time of said expression compared to when said drug agent is not administered to said subject.

2. The method of claim 1, wherein said polycationic structures comprise empty liposomes.

3. The method of claim 2, wherein said empty liposomes present in said first composition have a z-average diameter of about 20-85 nm.

4. The method of claim 1, wherein: A) said ratio is 10:1 to 18:1; and/or B) 2.0% to 6.0% of said first composition comprises dexamethasone or dexamethasone palmitate.

5. The method of claim 1, wherein each of said non-viral expression vectors each comprise only a single expression cassette, wherein said single expression cassette comprises said first nucleic acid sequence encoding said antibody light chain, and a second nucleic acid sequence encoding said antibody heavy chain.

6. The method of claim 1, wherein said drug agent is selected from colchicine, dexamethasone, dexamethasone palmitate, neutral lipids, valproic acid, theophylline, sildenafil, amlexanox, chloroquine, suberanilohydroxamic acid (SAHA), and L-arginine+sildenafil.

7. The method of claim 1, wherein said first amount of polycationic structures in said first composition comprises a mixture of cationic lipid and neutral lipid that reduces the expression of said antibody light and/or heavy chain compared to such expression when only said cationic lipid is employed in said method.

8. The method of claim 1, wherein said antibody light and/or heavy chain is expressed at said level in said subject for at least 21 consecutive days.

9. The method of claim 1, wherein said antibody light chain comprises a Rituximab light chain.

10. The method of claim 1, wherein said antibody heavy chain comprises a Rituximab heavy chain.

11. The method of claim 1, wherein said antibody light chain and/or heavy chain comprises said antibody light chain.

12. The method of claim 1, wherein said antibody light chain and/or heavy chain comprises said heavy chain.

13. The method of claim 1, wherein said antibody light chain and/or heavy chain comprises both said antibody light chain and heavy chain.

14. The method claim 13, wherein said first nucleic acid sequence further encodes a self-cleaving peptide between said antibody light chain and heavy chain.

15. The method of claim 1, wherein said non-viral expression vectors are CpG-free.

16. The method of claim 1, wherein said non-viral expression vectors are CpG-reduced.

17. The method of claim 1, wherein said second composition is administered to said subject between about 2 and 10 minutes after administering of said first composition.

18. The method of claim 1, wherein there are no detectable polycationic structures present in said second composition.

19. The method of claim 1, wherein said polycationic structures comprise liposomes, wherein said liposomes comprise 1,2-Dioleoyl-3-trimethylammonium propane (DOTAP).

20. The method of claim 1, wherein said subject is intravenously administered said third composition, wherein said third composition comprises dexamethasone and/or dexamethasone palmitate.

21. The method of claim 1, wherein said drug agent is in said first composition.

22. A method of expressing an antibody light chain and/or heavy chain in a subject comprising:

a) administering intravenously a first composition to a subject, wherein said first composition comprises a first amount of polycationic structures, and wherein said first composition is free, or essentially free, of nucleic acid molecules; and b) administering intravenously a second composition to said subject within about 300 minutes of administering said first composition, wherein said second composition comprises non-viral expression vectors, wherein said non-viral expression vectors are CpG-free or CpG-reduced, wherein said non-viral expression vectors each comprise a first nucleic acid sequence encoding an antibody light chain and/or heavy chain, and c) administering intravenously dexamethasone, dexamethasone palmitate, and/or neutral lipids to said subject, either in said first and/or second composition, or present in a third composition, wherein, as a result of said administering said first composition, said administering said second composition, and said administering of said dexamethasone, dexamethasone palmitate, and/or neutral lipid, said antibody light chain and/or heavy chain is expressed in said subject at a level of at least 50 pg/ml in serum for at least 7 consecutive days.

23. The method of claim 22, wherein said antibody light and/or heavy chain is expressed at said level in said subject for at least 21 consecutive days.

24. The method of claim 22, wherein said second composition is administered to said subject between about 2 and 10 minutes after administering of said first composition.

25. The method of claim 22, wherein there are no detectable polycationic structures present in said second composition.

26. The method of claim 22, wherein said polycationic structures comprise liposomes, wherein said liposomes comprise 1,2-Dioleoyl-3-trimethylammonium propane (DOTAP).

27. The method of claim 22, wherein said subject is intravenously administered said third composition, wherein said third composition comprises dexamethasone and/or dexamethasone palmitate.

28. The method of claim 22, wherein said drug agent is in said first composition.

* * * * *

SEQUENCE LISTING

<160> NUMBER OF SEQ ID NOS: 10

<210> SEQ ID NO 1
<211> LENGTH: 615
<212> TYPE: DNA
<213> ORGANISM: Homo sapiens

<400> SEQUENCE: 1

```
atggctggac ctgccaccca gagccccatg aagctgatgg ccctgcagct gctgctgtgg     60

cacagtgcac tctggacagt gcaggaagcc accccctgg gccctgccag ctccctgccc    120

cagagcttcc tgctcaagtg cttagagcaa gtgaggaaga tccaggggga tggggcagct    180

ctccaggaga agctgtgtgc cacctacaag ctgtgccacc ctgaggagct ggtgctgctg    240

ggacactctc tgggcatccc ctgggctccc ctgagcagct gccccagcca ggccctgcag    300

ctggcaggct gcttgagcca actccatagt ggccttttcc tctaccaggg gctcctgcag    360

gccctggaag ggatctcccc tgagttgggt cccaccttgg acacactgca gctggatgtt    420

gctgactttg ccaccaccat ctggcagcag atggaagaac tgggaatggc ccctgccctg    480

cagcccaccc agggtgccat gcctgccttt gcctctgctt tccagagaag ggcaggaggg    540

gtcctggttg cctcccatct gcagagcttc ctggaggtgt cctacagagt tctaagacac    600

cttgcccagc cctga                                                    615
```

<210> SEQ ID NO 2
<211> LENGTH: 207
<212> TYPE: PRT
<213> ORGANISM: Artificial sequence
<220> FEATURE:
<223> OTHER INFORMATION: synthetic

<400> SEQUENCE: 2

```
Met Ala Gly Pro Ala Thr Gln Ser Pro Met Lys Leu Met Ala Leu Gln
1               5                   10                  15

Leu Leu Leu Trp His Ser Ala Leu Trp Thr Val Gln Glu Ala Thr Pro
            20                  25                  30

Leu Gly Pro Ala Ser Ser Leu Pro Gln Ser Phe Leu Leu Lys Cys Leu
        35                  40                  45

Glu Gln Val Arg Lys Ile Gln Gly Asp Gly Ala Ala Leu Gln Glu Lys
    50                  55                  60

Leu Val Ser Glu Cys Ala Thr Tyr Lys Leu Cys His Pro Glu Glu Leu
65                  70                  75                  80

Val Leu Leu Gly His Ser Leu Gly Ile Pro Trp Ala Pro Leu Ser Ser
                85                  90                  95

Cys Pro Ser Gln Ala Leu Gln Leu Ala Gly Cys Leu Ser Gln Leu His
            100                 105                 110

Ser Gly Leu Phe Leu Tyr Gln Gly Leu Leu Gln Ala Leu Glu Gly Ile
        115                 120                 125

Ser Pro Glu Leu Gly Pro Thr Leu Asp Thr Leu Gln Leu Asp Val Ala
    130                 135                 140

Asp Phe Ala Thr Thr Ile Trp Gln Gln Met Glu Glu Leu Gly Met Ala
145                 150                 155                 160

Pro Ala Leu Gln Pro Thr Gln Gly Ala Met Pro Ala Phe Ala Ser Ala
                165                 170                 175

Phe Gln Arg Arg Ala Gly Gly Val Leu Val Ala Ser His Leu Gln Ser
            180                 185                 190

Phe Leu Glu Val Ser Tyr Arg Val Leu Arg His Leu Ala Gln Pro
```

195 200 205

<210> SEQ ID NO 3
<211> LENGTH: 9
<212> TYPE: DNA
<213> ORGANISM: Artificial sequence
<220> FEATURE:
<223> OTHER INFORMATION: synthetic

<400> SEQUENCE: 3 aagctttcc 9

<210> SEQ ID NO 4
<211> LENGTH: 8
<212> TYPE: RNA
<213> ORGANISM: Artificial sequence
<220> FEATURE:
<223> OTHER INFORMATION: synthetic

<400> SEQUENCE: 4 aagccacc 8

<210> SEQ ID NO 5
<211> LENGTH: 4308
<212> TYPE: DNA
<213> ORGANISM: Artificial sequence
<220> FEATURE:
<223> OTHER INFORMATION: synthetic

<400> SEQUENCE: 5
cactatgtgg acatgaattc aattggctag caggagtcaa tgggaaaaac ccattggagc 60
caagtacact gactcaatag ggactttcca ttgggttttg cccagtacat aaggtcaata 120
gggggtgagt caacaggaaa gtcccattgg agccaagtac attgagtcaa tagggacttt 180
ccaatgggtt ttgcccagta cataaggtca atgggaggta agccaatggg tttttcccat 240
tactgacatg tatactgagt cattagggac tttccaatgg gttttgccca gtacataagg 300
tcaatagggg tgaatcaaca ggaaagtccc attggagcca agtacactga gtcaataggg 360
actttccatt gggttttgcc cagtacaaaa ggtcaatagg gggtgagtca atgggttttt 420
cccattattg gcacatacat aaggtcaata ggggtgacta gtggagaaga gcatgcttga 480
gggctgagtg cccctcagtg ggcagagagc acatggccca cagtccctga gaagttgggg 540
ggaggggtgg gcaattgaac tggtgcctag agaaggtggg gcttgggtaa actgggaaag 600
tgatgtggtg tactggctcc acctttttcc ccagggtggg ggagaaccat atataagtgc 660
agtagtctct gtgaacattc aagcttctgc cttctccctc ctgtgagttt ggtaagtcac 720
tgactgtcta tgcctgggaa agggtgggca ggagatgggg cagtgcagga aaagtggcac 780
tatgaaccct gcagccctag acaattgtac taaccttctt ctctttcctc tcctgacagg 840
ttggtaacca agccaccatg ggctggtccc tgatcctgct gttcctggtg gctgtggcca 900
ccagagtgct gagccaggtg cagctgcagc agcctggggc tgagcttgtg aaacctgggg 960
cctctgtgaa gatgagctgc aaggcctctg gctacacctt caccagctac aacatgcact 1020
gggtcaagca gacccctggc agaggcctgg aatggattgg agccatctac cctggcaatg 1080
gggacacctc ctacaaccag aagttcaagg gcaaggccac cctgacagct gacaagagca 1140
gcagcacagc ctacatgcag ctgtccagcc tgacctctga ggactctgct gtgtactact 1200
gtgccaggtc cacctactat gggggagact ggtacttcaa tgtgtgggga gctggcacca 1260
cagtgacagt gtctgctgcc agcaccaagg gcccctctgt gtttcctctg gcccccagca 1320

```
gcaagagcac ctctggggga acagctgccc tgggctgcct tgtgaaggac tacttccctg   1380
agcctgtgac tgtgtcctgg aactctgggg ccctgacatc tggggtgcac accttccctg   1440
cagtgctgca gtccagtggc ctgtactccc tgtcctctgt tgtgacagtg cccagctcca   1500
gcctgggcac ccagacctac atctgcaatg tgaaccacaa gcccagcaac accaaggtgg   1560
acaagaaggc tgagcccaag agctgtgaca agacccacac ctgtcccccc tgtcctgccc   1620
ctgaactgct gggaggacct tctgtgttcc tgttcccacc caagcccaag gataccctga   1680
tgatcagcag aacccctgaa gtgacctgtg tggtggtgga tgtgtcccat gaggacccag   1740
aagtgaagtt caattggtat gtggatgggg tggaagtgca caatgccaag accaagccca   1800
gagaggaaca gtacaacagc acctacagag tggtgtctgt gctgactgtg ctgcaccagg   1860
actggctgaa tggcaaagag tacaagtgca aggtgtccaa caaggccctg ccagccccca   1920
ttgagaaaac catcagcaag gccaagggcc agcctagaga accccaggtg tacacactgc   1980
cccctagcag ggatgagctg accaagaacc aggtgtccct gacatgcctt gtgaaaggct   2040
tctacccctc tgacattgct gtggaatggg agagcaatgg acagcctgag aacaactaca   2100
agaccacccc ccctgtgctg gactctgatg gctcattctt cctgtacagc aagctgacag   2160
tggacaagtc cagatggcag cagggcaatg tgttcagctg ctctgtgatg catgaggccc   2220
tgcacaacca ctacacccag aaaagcctgt ccctgtcccc tggcaagaga gcaaagaggg   2280
caccagtgaa acagactttg aattttgacc ttctcaagtt ggcaggagat gtggagtcca   2340
accctggacc tatggacttc caggtgcaga tcatcagctt tctgctgatc tctgcctctg   2400
tgatcatgag cagaggccag attgtgctga gccagagccc tgccatcctg tctgcaagcc   2460
ctggggagaa agtgaccatg acctgcagag ccagcagctc tgtgtcctac atccactggt   2520
tccagcagaa gcctggcagc agccccaagc cttggatcta tgccaccagc aacctggcat   2580
ctggggtgcc agtcagattc tctggctctg gatctggcac cagctacagc ctgaccatca   2640
gcagagtgga agctgaggat gctgccacct actactgcca gcagtggacc agcaatcccc   2700
ccacctttgg agggggcacc aagctggaaa tcaagagaac agtggctgcc ccctctgtgt   2760
tcatcttccc accctctgat gagcagctga agtctggaac agcctctgtt gtgtgcctgc   2820
tgaacaactt ctaccccaga gaagccaagg tgcagtggaa ggtggacaat gccctgcagt   2880
ctggcaactc ccaggaatct gtgacagagc aggacagcaa ggactccacc tactccctga   2940
gcagcaccct gaccctgagc aaggctgact atgagaagca caaagtgtat gcctgtgaag   3000
tgacccacca gggcctgtcc agccctgtga ccaagagctt caacagaggg gagagctgaa   3060
gatctacttc tggctaataa aagatcagag ctctagtgat ctgtgtgttg gttttttgtg   3120
tctgcattct agctctagtg atcagcagtt caacctgttg atagtatgta ctaagctctc   3180
atgtttaatg tactaagctc tcatgtttaa tgaactaaac cctcatggct aatgtactaa   3240
gctctcatgg ctaatgtact aagctctcat gtttcatgta ctaagctctc atgtttgaac   3300
aataaaatta atataaatca gcaacttaaa tagcctctaa ggttttaagt tttataagaa   3360
aaaaaagaat atataaggct tttaaaggtt ttaaggtttc ctaggttatc ctcatatgag   3420
ctcttagaaa aactcatcca gcatcaaatg aaactgcaat ttattcatat caggattatc   3480
aataccatat ttttgaaaaa gtcttttctg taatgaagga gaaaactcac ccaggcagtt   3540
ccataggatg gcaagatcct ggtatctgtc tgcaattcca actcttccaa catcaataca   3600
acctattaat ttcccctcat caaaaataag gttatcaagt gagaaatcac catgagtgac   3660
```

```
cactgaatct ggtgagaatg gcaaaagatt atgcatttct ttccagactt gttcaacagg   3720
ccagccattt ctctcatcat caaaatcact ggcatcaacc aaaccattat tcattcttga   3780
ttgggcctga gccagtctaa atactctatc agagttaaaa ggacaattac aaacaggaat   3840
ggaatgcaat cttctcagga acactgccag ggcatcaaca atattttcac ctgaatcagg   3900
atattcttcc aatacctgga atgctgtttt ccctgggatg gcagtggtga gtaaccatgc   3960
atcatcagga gttctgataa aatgcttgat ggttggaaga ggcataaatt cagtcagcca   4020
gtttagtctg accatctcat ctgtaacatc attggcaaca gaacctttgc catgtttcag   4080
aaacaactct ggggcatctg gcttcccata caatctatag attgtggcac ctgattgccc   4140
aacattatct ctagcccatt tatacccata taaatcagca tccatgttgg aatttaatct   4200
tggcctggag caagaggttt ctctttgaat atggctcata catgtgcacc tcctatagtg   4260
agttgtatta tactatgcag atatactatg ccaatgttta attgtcag               4308
```

<210> SEQ ID NO 6
<211> LENGTH: 5131
<212> TYPE: DNA
<213> ORGANISM: Artificial sequence
<220> FEATURE:
<223> OTHER INFORMATION: synthetic

<400> SEQUENCE: 6

```
cactatgtgg acatgaattc aattggctag caggagtcaa tgggaaaaac ccattggagc     60
caagtacact gactcaatag ggactttcca ttgggttttg cccagtacat aaggtcaata    120
gggggtgagt caacaggaaa gtcccattgg agccaagtac attgagtcaa tagggacttt    180
ccaatgggtt ttgcccagta cataaggtca atgggaggta agccaatggg tttttcccat    240
tactgacatg tatactgagt cattagggac tttccaatgg gttttgccca gtacataagg    300
tcaatagggg tgaatcaaca ggaaagtccc attggagcca agtacactga gtcaataggg    360
actttccatt gggttttgcc cagtacaaaa ggtcaatagg gggtgagtca atgggttttt    420
cccattattg gcacatacat aaggtcaata ggggtgacta gtggagaaga gcatgcttga    480
gggctgagtg cccctcagtg ggcagagagc acatggccca cagtccctga gaagttgggg    540
ggaggggtgg gcaattgaac tggtgcctag agaaggtggg gcttgggtaa actgggaaag    600
tgatgtggtg tactggctcc accttttttcc ccagggtggg ggagaaccat atataagtgc    660
agtagtctct gtgaacattc aagcttctgc cttctccctc ctgtgagttt ggtaagtcac    720
tgactgtcta tgcctgggaa agggtgggca ggagatgggg cagtgcagga aaagtggcac    780
tatgaaccct gcagccctag acaattgtac taaccttctt ctctttcctc tcctgacagg    840
ttggtaacca agctttccat gggttggagc ctcatcttgc tcttccttgt agctgttgct    900
actagagtcc tgtcccaggt acaactgcag cagcctgggg ctgagctggt gaagcctggg    960
gcctcagtga agatgtcctg caaggcttct ggctacacat ttaccagtta caatatgcac   1020
tgggtaaaac agacacctgg taggggcctg gaatggattg gagctattta tcctggaaat   1080
ggtgatactt cctacaatca gaagttcaaa ggcaaggcca cattgactgc agacaaatcc   1140
tccagcacag cctacatgca gctcagcagc ctgacatctg aggactctgc agtctattac   1200
tgtgcaagat caacttacta tggtggtgac tggtacttca atgtctgggg tgcagggacc   1260
acagtcacag tctctgcagc aagcaccaag ggcccatctg tcttcccccct ggcaccctcc   1320
tccaagagca cctctggggg cacagctgcc ctgggctgcc tggtcaagga ctacttccct   1380
gaacctgtga cagtgtcatg gaactcagga gccctgacca gtggtgtgca caccttccct   1440
```

```
gctgtcctac agtcctcagg actctactcc ctcagcagtg tggtgactgt gccctccagc   1500
agcttgggca cccagaccta catctgcaat gtgaatcaca agcccagcaa caccaaggtg   1560
gacaagaaag cagagcccaa atcttgtgac aaaactcaca catgcccacc ttgcccagca   1620
cctgaactcc tggggggacc ttcagtcttc ctcttccccc caaaacccaa ggacaccctc   1680
atgatctcca ggacccctga ggtcacatgt gtggtggtgg atgtgagcca tgaagaccct   1740
gaggtcaagt tcaactggta tgtggatggt gtggaggtgc ataatgccaa gacaaagcca   1800
agggaggagc agtacaacag cacttacaga gtggtcagtg tcctcactgt cctgcaccag   1860
gactggctga atggcaagga gtacaagtgc aaggtctcca acaaagccct cccagccccc   1920
atagagaaaa ccatctccaa agccaaaggg cagcccagag aaccacaggt gtacaccctg   1980
cccccatcca gggatgagct gaccaagaac caggtcagcc tgacctgcct ggtcaaaggc   2040
ttctatccca gtgacattgc tgtggagtgg gagagcaatg ggcagcctga gaacaactac   2100
aagaccactc ctcctgtgct ggactctgat ggctccttct tcctctacag caagctcaca   2160
gtggacaaga gcaggtggca gcaggggaat gtcttctcat gctcagtcat gcatgaggct   2220
ctgcacaacc actacacaca gaagagcctc tccctgtctc caggtaaatg atagatctac   2280
ttctggctaa taaaagatca gagctctagt gatctgtgtg ttggtttttt gtgtctgcat   2340
tctagcagga gtcaatggga aaaacccatt ggagccaagt acactgactc aatagggact   2400
ttccattggg ttttgcccag tacataaggt caataggggg tgagtcaaca ggaaagtccc   2460
attggagcca agtacattga gtcaataggg actttccaat gggttttgcc cagtacataa   2520
ggtcaatggg aggtaagcca atgggttttt cccattactg acatgtatac tgagtcatta   2580
gggactttcc aatgggtttt gcccagtaca taaggtcaat aggggtgaat caacaggaaa   2640
gtcccattgg agccaagtac actgagtcaa tagggacttt ccattgggtt ttgcccagta   2700
caaaaggtca ataggggtg agtcaatggg tttttcccat tattggcaca tacataaggt   2760
caataggggt gactagtgga gaagagcatg cttgagggct gagtgcccct cagtgggcag   2820
agagcacatg gcccacagtc cctgagaagt tggggggagg ggtgggcaat tgaactggtg   2880
cctagagaag gtggggcttg ggtaaactgg gaaagtgatg tggtgtactg gctccacctt   2940
tttccccagg gtgggggaga accatatata agtgcagtag tctctgtgaa cattcaagct   3000
tctgccttct ccctcctgtg agtttggtaa gtcactgact gtctatgcct gggaaagggt   3060
gggcaggaga tggggcagtg caggaaaagt ggcactatga accctgcagc cctagacaat   3120
tgtactaacc ttcttctctt tcctctcctg acaggttggt aaccaagctt tccatggatt   3180
ttcaggtgca gattatcagc ttcctcctaa tcagtgcttc agtcataatg tccagaggac   3240
aaattgttct ctcccagtct ccagcaatcc tgtctgcatc tccaggggag aaggtcacaa   3300
tgacttgcag ggccagctca agtgtaagtt acatccactg gttccagcag aagccaggat   3360
cctcccccaa accctggatt tatgccacat ccaacctggc ttctggagtc cctgttagat   3420
tcagtggcag tgggtctggg acttcttact ctctcaccat cagcagagtg gaggctgaag   3480
atgctgccac ttattactgc cagcagtgga ctagtaaccc acccactttt ggagggggga   3540
ccaagctgga aatcaaaaga acagtggctg caccatctgt cttcatcttc cctccatctg   3600
atgagcagtt gaaatctgga actgcctctg ttgtgtgcct gctgaataac ttctatccca   3660
gagaggccaa agtacagtgg aaggtggata atgccctcca atcaggtaac tcccaggaga   3720
gtgtcacaga gcaggacagc aaggacagca cctacagcct cagcagcacc ctgacactga   3780
```

```
gcaaagcaga ctatgagaaa cacaaagtct atgcctgtga agtcacccat cagggcctga   3840
gctctcctgt cacaaagagc ttcaacaggg gagagtcttg atagatctac ttctggctaa   3900
taaaagatca gagctctagt gatctgtgtg ttggtttttt gtgtctgcat tctagctcta   3960
gtgatcagca gttcaacctg ttgatagtat gtactaagct ctcatgttta atgtactaag   4020
ctctcatgtt taatgaacta aaccctcatg gctaatgtac taagctctca tggctaatgt   4080
actaagctct catgtttcat gtactaagct ctcatgtttg aacaataaaa ttaatataaa   4140
tcagcaactt aaatagcctc taaggtttta agttttataa gaaaaaaaag aatatataag   4200
gcttttaaag gttttaaggt ttcctaggtt atcctcatat gagctcttag aaaaactcat   4260
ccagcatcaa atgaaactgc aatttattca tatcaggatt atcaatacca tatttttgaa   4320
aaagtctttt ctgtaatgaa ggagaaaact cacccaggca gttccatagg atggcaagat   4380
cctggtatct gtctgcaatt ccaactcttc caacatcaat acaacctatt aatttcccct   4440
catcaaaaat aaggttatca agtgagaaat caccatgagt gaccactgaa tctggtgaga   4500
atggcaaaag attatgcatt tctttccaga cttgttcaac aggccagcca tttctctcat   4560
catcaaaatc actggcatca accaaaccat tattcattct tgattgggcc tgagccagtc   4620
taaatactct atcagagtta aaaggacaat tacaaacagg aatggaatgc aatcttctca   4680
ggaacactgc cagggcatca acaatatttt cacctgaatc aggatattct tccaatacct   4740
ggaatgctgt tttccctggg atggcagtgg tgagtaacca tgcatcatca ggagttctga   4800
taaaatgctt gatggttgga agaggcataa attcagtcag ccagtttagt ctgaccatct   4860
catctgtaac atcattggca acagaacctt tgccatgttt cagaaacaac tctggggcat   4920
ctggcttccc atacaatcta tagattgtgg cacctgattg cccaacatta tctctagccc   4980
atttataccc atataaatca gcatccatgt tggaatttaa tcttggcctg gagcaagagg   5040
tttctctttg aatatggctc atacatgtgc acctcctata gtgagttgta ttatactatg   5100
cagatatact atgccaatgt ttaattgtca g                                  5131
```

<210> SEQ ID NO 7
<211> LENGTH: 5147
<212> TYPE: DNA
<213> ORGANISM: Artificial sequence
<220> FEATURE:
<223> OTHER INFORMATION: synthetic

<400> SEQUENCE: 7

```
cactatgtgg acatgaattc aattggctag caggagtcaa tgggaaaaac ccattggagc     60
caagtacact gactcaatag ggactttcca ttgggttttg cccagtacat aaggtcaata    120
gggggtgagt caacaggaaa gtcccattgg agccaagtac attgagtcaa tagggacttt    180
ccaatgggtt ttgcccagta cataaggtca atgggaggta agccaatggg tttttcccat    240
tactgacatg tatactgagt cattagggac tttccaatgg gttttgccca gtacataagg    300
tcaatagggg tgaatcaaca ggaaagtccc attggagcca agtacactga gtcaataggg    360
actttccatt gggttttgcc cagtacaaaa ggtcaatagg gggtgagtca atgggttttt    420
cccattattg gcacatacat aaggtcaata ggggtgacta gtggagaaga gcatgcttga    480
gggctgagtg cccctcagtg ggcagagagc acatggccca cagtccctga gaagttgggg    540
ggaggggtgg gcaattgaac tggtgcctag agaaggtggg gcttgggtaa actgggaaag    600
tgatgtggtg tactggctcc accttttttcc ccagggtggg ggagaaccat atataagtgc    660
agtagtctct gtgaacattc aagcttctgc cttctccctc ctgtgagttt ggtaagtcac    720
```

```
tgactgtcta tgcctgggaa agggtgggca ggagatgggg cagtgcagga aaagtggcac    780
tatgaaccct gcagccctag acaattgtac taaccttctt ctctttcctc tcctgacagg    840
ttggtaacct gacaggttgg taaccaagct ttccatgggt tggagcctca tcttgctctt    900
ccttgtcgct gttgctacgc gtgtcctgtc ccaggtacaa ctgcagcagc ctggggctga    960
gctggtgaag cctggggcct cagtgaagat gtcctgcaag gcttctggct acacatttac   1020
cagttacaat atgcactggg taaaacagac acctggtcgg ggcctggaat ggattggagc   1080
tatttatccc ggaaatggtg atacttccta caatcagaag ttcaaaggca aggccacatt   1140
gactgcagac aaatcctcca gcacagccta catgcagctc agcagcctga catctgagga   1200
ctctgcggtc tattactgtg caagatcgac ttactacggc ggtgactggt acttcaatgt   1260
ctggggcgca gggaccacgg tcaccgtctc tgcagctagc accaagggcc catcggtctt   1320
ccccctggca ccctcctcca agagcacctc tgggggcaca gcggccctgg gctgcctggt   1380
caaggactac ttccccgaac cggtgacggt gtcgtggaac tcaggcgccc tgaccagcgg   1440
cgtgcacacc ttcccggctg tcctacagtc ctcaggactc tactccctca gcagcgtggt   1500
gaccgtgccc tccagcagct tgggcaccca gacctacatc tgcaacgtga atcacaagcc   1560
cagcaacacc aaggtggaca agaaagcaga gcccaaatct tgtgacaaaa ctcacacatg   1620
cccaccgtgc ccagcacctg aactcctggg gggaccgtca gtcttcctct tccccccaaa   1680
acccaaggac accctcatga tctcccggac ccctgaggtc acatgcgtgg tggtggacgt   1740
gagccacgaa gaccctgagg tcaagttcaa ctggtacgtg gacggcgtgg aggtgcataa   1800
tgccaagaca aagccgcggg aggagcagta caacagcacg taccgtgtgg tcagcgtcct   1860
caccgtcctg caccaggact ggctgaatgg caaggagtac aagtgcaagg tctccaacaa   1920
agccctccca gcccccatcg agaaaaccat ctccaaagcc aaagggcagc cccgagaacc   1980
acaggtgtac accctgcccc catcccggga tgagctgacc aagaaccagg tcagcctgac   2040
ctgcctggtc aaaggcttct atcccagcga catcgccgtg gagtgggaga gcaatgggca   2100
gccggagaac aactacaaga ccacgcctcc cgtgctggac tccgacggct ccttcttcct   2160
ctacagcaag ctcaccgtgg acaagagcag gtggcagcag gggaacgtct tctcatgctc   2220
cgtcatgcat gaggctctgc acaaccacta cacgcagaag agcctctccc tgtctccggg   2280
taaatgatag atctacttct ggctaataaa agatcagagc tctagtgatc tgtgtgttgg   2340
tttttgtgt ctgcattcta gcaggagtca atgggaaaaa cccattggag ccaagtacac   2400
tgactcaata gggactttcc attgggtttt gcccagtaca taaggtcaat agggggtgag   2460
tcaacaggaa agtcccattg gagccaagta cattgagtca atagggactt tccaatgggt   2520
tttgcccagt acataaggtc aatgggaggt aagccaatgg gtttttccca ttactgacat   2580
gtatactgag tcattaggga ctttccaatg ggttttgccc agtacataag gtcaataggg   2640
gtgaatcaac aggaaagtcc cattggagcc aagtacactg agtcaatagg gactttccat   2700
tgggttttgc ccagtacaaa aggtcaatag ggggtgagtc aatgggtttt tcccattatt   2760
ggcacataca taaggtcaat aggggtgact agtggagaag agcatgcttg agggctgagt   2820
gcccctcagt gggcagagag cacatggccc acagtccctg agaagttggg gggaggggtg   2880
ggcaattgaa ctggtgccta gagaaggtgg ggcttgggta aactgggaaa gtgatgtggt   2940
gtactggctc cacctttttc cccagggtgg gggagaacca tatataagtg cagtagtctc   3000
tgtgaacatt caagcttctg ccttctccct cctgtgagtt tggtaagtca ctgactgtct   3060
```

```
atgcctggga aagggtgggc aggagatggg gcagtgcagg aaaagtggca ctatgaaccc   3120
tgcagcccta gacaattgta ctaaccttct tctctttcct ctcctgacag gttggtaacc   3180
aagctttcca tggattttca ggtgcagatt atcagcttcc tcctaatcag tgcttcagtc   3240
ataatgtcca gaggacaaat tgttctctcc cagtctccag caatcctgtc tgcatctcca   3300
ggggagaagg tcacaatgac ttgcagggcc agctcaagtg taagttacat ccactggttc   3360
cagcagaagc caggatcctc ccccaaaccc tggatttatg ccacatccaa cctggcttct   3420
ggagtccctg ttcgcttcag tggcagtggg tctgggactt cttactctct caccatcagc   3480
agagtggagg ctgaagatgc tgccacttat tactgccagc agtggactag taacccaccc   3540
acgttcggag gggggaccaa gctggaaatc aaacgtacgg tggctgcacc atctgtcttc   3600
atcttcccgc catctgatga gcagttgaaa tctggaactg cctctgttgt gtgcctgctg   3660
aataacttct atcccagaga ggccaaagta cagtggaagg tggataacgc cctccaatcg   3720
ggtaactccc aggagagtgt cacagagcag gacagcaagg acagcaccta cagcctcagc   3780
agcaccctga cgctgagcaa agcagactac gagaaacaca aagtctacgc ctgcgaagtc   3840
acccatcagg gcctgagctc gcccgtcaca aagagcttca acaggggaga gtcttgatag   3900
atctacttct ggctaataaa agatcagagc tctagtgatc tgtgtgttgg tttttttgtgt   3960
ctgcattcta gctctagtga tcagcagttc aacctgttga tagtatgtac taagctctca   4020
tgtttaatgt actaagctct catgtttaat gaactaaacc ctcatggcta atgtactaag   4080
ctctcatggc taatgtacta agctctcatg tttcatgtac taagctctca tgtttgaaca   4140
ataaaattaa tataaatcag caacttaaat agcctctaag gttttaagtt ttataagaaa   4200
aaaaagaata tataaggctt ttaaaggttt taaggtttcc taggttatcc tcatatgagc   4260
tcttagaaaa actcatccag catcaaatga aactgcaatt tattcatatc aggattatca   4320
ataccatatt tttgaaaaag tcttttctgt aatgaaggag aaaactcacc caggcagttc   4380
cataggatgg caagatcctg gtatctgtct gcaattccaa ctcttccaac atcaatacaa   4440
cctattaatt tcccctcatc aaaaataagg ttatcaagtg agaaatcacc atgagtgacc   4500
actgaatctg gtgagaatgg caaaagatta tgcatttctt tccagacttg ttcaacaggc   4560
cagccatttc tctcatcatc aaaatcactg gcatcaacca aaccattatt cattcttgat   4620
tgggcctgag ccagtctaaa tactctatca gagttaaaag gacaattaca aacaggaatg   4680
gaatgcaatc ttctcaggaa cactgccagg gcatcaacaa tattttcacc tgaatcagga   4740
tattcttcca atacctggaa tgctgttttc cctgggatgg cagtggtgag taaccatgca   4800
tcatcaggag ttctgataaa atgcttgatg gttggaagag gcataaattc agtcagccag   4860
tttagtctga ccatctcatc tgtaacatca ttggcaacag aacctttgcc atgtttcaga   4920
aacaactctg gggcatctgg cttcccatac aatctataga ttgtggcacc tgattgccca   4980
acattatctc tagcccattt atacccatat aaatcagcat ccatgttgga atttaatctt   5040
ggcctggagc aagaggtttc tctttgaata tggctcatac atgtgcacct cctatagtga   5100
gttgtattat actatgcaga tatactatgc caatgtttaa ttgtcag                5147
```

<210> SEQ ID NO 8
<211> LENGTH: 5128
<212> TYPE: DNA
<213> ORGANISM: Artificial sequence
<220> FEATURE:
<223> OTHER INFORMATION: synthetic

<400> SEQUENCE: 8

```
cactatgtgg acatgaattc aattggctag caggagtcaa tgggaaaaac ccattggagc     60
caagtacact gactcaatag ggactttcca ttgggttttg cccagtacat aaggtcaata    120
gggggtgagt caacaggaaa gtcccattgg agccaagtac attgagtcaa tagggacttt    180
ccaatgggtt ttgcccagta cataaggtca atgggaggta agccaatggg tttttcccat    240
tactgacatg tatactgagt cattagggac tttccaatgg gttttgccca gtacataagg    300
tcaatagggg tgaatcaaca ggaaagtccc attggagcca agtacactga gtcaataggg    360
actttccatt gggttttgcc cagtacaaaa ggtcaatagg gggtgagtca atgggttttt    420
cccattattg gcacatacat aaggtcaata ggggtgacta gtggagaaga gcatgcttga    480
gggctgagtg cccctcagtg ggcagagagc acatggccca cagtccctga gaagttgggg    540
ggaggggtgg gcaattgaac tggtgcctag agaaggtggg gcttgggtaa actgggaaag    600
tgatgtggtg tactggctcc accttttttcc ccagggtggg ggagaaccat atataagtgc    660
agtagtctct gtgaacattc aagcttctgc cttctccctc ctgtgagttt ggtaagtcac    720
tgactgtcta tgcctgggaa agggtgggca ggagatgggg cagtgcagga aaagtggcac    780
tatgaaccct gcagccctag acaattgtac taaccttctt ctctttcctc tcctgacagg    840
ttggtaacca agctttccat gggctggtcc ctgatcctgc tgttcctggt ggctgtggcc    900
accagagtgc tgagccaggt gcagctgcag cagcctgggg ctgagcttgt gaaacctggg    960
gcctctgtga agatgagctg caaggcctct ggctacacct tcaccagcta caacatgcac   1020
tgggtcaagc agacccctgg cagaggcctg gaatggattg gagccatcta ccctggcaat   1080
ggggacacct cctacaacca gaagttcaag ggcaaggcca ccctgacagc tgacaagagc   1140
agcagcacag cctacatgca gctgtccagc ctgacctctg aggactctgc tgtgtactac   1200
tgtgccaggt ccacctacta tgggggagac tggtacttca atgtgtgggg agctggcacc   1260
acagtgacag tgtctgctgc cagcaccaag ggcccctctg tgtttcctct ggcccccagc   1320
agcaagagca cctctggggg aacagctgcc ctgggctgcc ttgtgaagga ctacttccct   1380
gagcctgtga ctgtgtcctg gaactctggg gccctgacat ctggggtgca caccttccct   1440
gcagtgctgc agtccagtgg cctgtactcc ctgtcctctg ttgtgacagt gcccagctcc   1500
agcctgggca cccagaccta catctgcaat gtgaaccaca agcccagcaa caccaaggtg   1560
gacaagaagg ctgagcccaa gagctgtgac aagacccaca cctgtccccc ctgtcctgcc   1620
cctgaactgc tgggaggacc ttctgtgttc ctgttcccac ccaagcccaa ggataccctg   1680
atgatcagca gaacccctga agtgacctgt gtggtggtgg atgtgtccca tgaggaccca   1740
gaagtgaagt tcaattggta tgtggatggg gtggaagtgc acaatgccaa gaccaagccc   1800
agagaggaac agtacaacag cacctacaga gtggtgtctg tgctgactgt gctgcaccag   1860
gactggctga atggcaaaga gtacaagtgc aaggtgtcca acaaggccct gccagccccc   1920
attgagaaaa ccatcagcaa ggccaagggc cagcctagag aaccccaggt gtacacactg   1980
ccccctagca gggatgagct gaccaagaac caggtgtccc tgacatgcct tgtgaaaggc   2040
ttctacccct ctgacattgc tgtggaatgg gagagcaatg gacagcctga gaacaactac   2100
aagaccaccc cccctgtgct ggactctgat ggctcattct tcctgtacag caagctgaca   2160
gtggacaagt ccagatggca gcagggcaat gtgttcagct gctctgtgat gcatgaggcc   2220
ctgcacaacc actacaccca gaaaagcctg tccctgtccc ctggcaagtg aagatctact   2280
tctggctaat aaaagatcag agctctagtg atctgtgtgt tggtttttttg tgtctgcatt   2340
```

-continued

```
ctagcaggag tcaatgggaa aaacccattg gagccaagta cactgactca atagggactt   2400
tccattgggt tttgcccagt acataaggtc aatagggggt gagtcaacag gaaagtccca   2460
ttggagccaa gtacattgag tcaataggga ctttccaatg ggttttgccc agtacataag   2520
gtcaatggga ggtaagccaa tgggtttttc ccattactga catgtatact gagtcattag   2580
ggactttcca atgggttttg cccagtacat aaggtcaata ggggtgaatc aacaggaaag   2640
tcccattgga gccaagtaca ctgagtcaat agggactttc cattgggttt tgcccagtac   2700
aaaaggtcaa taggggggtga gtcaatgggt ttttcccatt attggcacat acataaggtc   2760
aataggggtg actagtggag aagagcatgc ttgagggctg agtgcccctc agtgggcaga   2820
gagcacatgg cccacagtcc ctgagaagtt ggggggaggg gtgggcaatt gaactggtgc   2880
ctagagaagg tggggcttgg gtaaactggg aaagtgatgt ggtgtactgg ctccaccttt   2940
ttccccaggg tgggggagaa ccatatataa gtgcagtagt ctctgtgaac attcaagctt   3000
ctgccttctc cctcctgtga gtttggtaag tcactgactg tctatgcctg ggaaagggtg   3060
ggcaggagat ggggcagtgc aggaaaagtg gcactatgaa ccctgcagcc ctagacaatt   3120
gtactaacct tcttctcttt cctctcctga caggttggta accaagccac catggacttc   3180
caggtgcaga tcatcagctt tctgctgatc tctgcctctg tgatcatgag cagaggccag   3240
attgtgctga gccagagccc tgccatcctg tctgcaagcc ctggggagaa agtgaccatg   3300
acctgcagag ccagcagctc tgtgtcctac atccactggt tccagcagaa gcctggcagc   3360
agccccaagc cttggatcta tgccaccagc aacctggcat ctggggtgcc agtcagattc   3420
tctggctctg gatctggcac cagctacagc ctgaccatca gcagagtgga agctgaggat   3480
gctgccacct actactgcca gcagtggacc agcaatcccc ccacctttgg agggggcacc   3540
aagctggaaa tcaagagaac agtggctgcc ccctctgtgt tcatcttccc accctctgat   3600
gagcagctga agtctggaac agcctctgtt gtgtgcctgc tgaacaactt ctaccccaga   3660
gaagccaagg tgcagtggaa ggtggacaat gccctgcagt ctggcaactc ccaggaatct   3720
gtgacagagc aggacagcaa ggactccacc tactccctga gcagcaccct gaccctgagc   3780
aaggctgact atgagaagca caaagtgtat gcctgtgaag tgacccacca gggcctgtcc   3840
agccctgtga ccaagagctt caacagaggg gagagctgaa gatctacttc tggctaataa   3900
aagatcagag ctctagtgat ctgtgtgttg gtttttttgtg tctgcattct agctctagtg   3960
atcagcagtt caacctgttg atagtatgta ctaagctctc atgtttaatg tactaagctc   4020
tcatgtttaa tgaactaaac cctcatggct aatgtactaa gctctcatgg ctaatgtact   4080
aagctctcat gtttcatgta ctaagctctc atgtttgaac aataaaatta atataaatca   4140
gcaacttaaa tagcctctaa ggttttaagt tttataagaa aaaaaagaat atataaggct   4200
tttaaaggtt ttaaggtttc ctaggttatc ctcatatgag ctcttagaaa aactcatcca   4260
gcatcaaatg aaactgcaat ttattcatat caggattatc aataccatat ttttgaaaaa   4320
gtcttttctg taatgaagga gaaaactcac ccaggcagtt ccataggatg gcaagatcct   4380
ggtatctgtc tgcaattcca actcttccaa catcaataca acctattaat ttcccctcat   4440
caaaaataag gttatcaagt gagaaatcac catgagtgac cactgaatct ggtgagaatg   4500
gcaaaagatt atgcatttct ttccagactt gttcaacagg ccagccattt ctctcatcat   4560
caaaatcact ggcatcaacc aaaccattat tcattcttga ttgggcctga gccagtctaa   4620
atactctatc agagttaaaa ggacaattac aaacaggaat ggaatgcaat cttctcagga   4680
acactgccag ggcatcaaca atattttcac ctgaatcagg atattcttcc aatacctgga   4740
```

```
atgctgtttt ccctgggatg gcagtggtga gtaaccatgc atcatcagga gttctgataa   4800

aatgcttgat ggttggaaga ggcataaatt cagtcagcca gtttagtctg accatctcat   4860

ctgtaacatc attggcaaca gaacctttgc catgtttcag aaacaactct ggggcatctg   4920

gcttcccata caatctatag attgtggcac ctgattgccc aacattatct ctagcccatt   4980

tatacccata taaatcagca tccatgttgg aatttaatct tggcctggag caagaggttt   5040

ctctttgaat atggctcata catgtgcacc tcctatagtg agttgtatta tactatgcag   5100

atatactatg ccaatgttta attgtcag                                      5128
```

<210> SEQ ID NO 9
<211> LENGTH: 7413
<212> TYPE: DNA
<213> ORGANISM: Artificial sequence
<220> FEATURE:
<223> OTHER INFORMATION: synthetic

<400> SEQUENCE: 9

```
cactatgtgt taattaaaat tatctctaag gcatgtgaac tggctgtctt ggttttcatc     60

tgtacttcat ctgctacctc tgtgacctga aacatattta taattccatt aagctgtgca    120

tatgatagat ttatcatatg tattttcctt aaaggatttt tgtaagaact aattgaattg    180

atacctgtaa agtctttatc acactaccca ataaataata aatctctttg ttcagctctc    240

tgtttctata aatatgtacc agttttattg tttttagtgg tagtgatttt attctctttc    300

tatatatata cacacacatg tgtgcattca taaatatata caatttttat gaataaaaaa    360

ttattagcaa tcaatattga aaaccactga tttttgttta tgtgagcaaa cagcagatta    420

aaaggaattt gaattctcat agctagcagg agtcaatggg aaaaaaccat tggagccaag    480

tacactgact caatagggac tttccattgg gttttgccca gtacataagg tcaatagggg    540

gtgagtcaac aggaaagtcc cattggagcc aagtacattg agtcaatagg gactttccaa    600

tgggttttgc ccagtacata aggtcaatgg gaggtaagcc aatgggtttt tcccattact    660

gacatgtata ctgagtcatt agggactttc caatgggttt tgcccagtac ataaggtcaa    720

taggggtgaa tcaacaggaa agtcccattg gagccaagta cactgagtca atagggactt    780

tccattgggt tttgcccagt acaaaaggtc aatagggggt gagtcaatgg gtttttccca    840

ttattggcac atacataagg tcaatagggg tgactagtgg agaagagcat gcttgagggc    900

tgagtgcccc tcagtgggca gagagcacat ggcccacagt ccctgagaag ttgggggggag   960

gggtgggcaa ttgaactggt gcctagagaa ggtggggctt gggtaaactg ggaaagtgat   1020

gtggtgtact ggctccacct tttccccag ggtgggggag aaccatatat aagtgcagta   1080

gtctctgtga acattcaagc ttctgccttc tccctcctgt gagtttggta agtcactgac   1140

tgtctatgcc tgggaaaggg tgggcaggag atggggcagt gcaggaaaag tggcactatg   1200

aaccctgcag ccctagacaa ttgtactaac cttcttctct ttcctctcct gacaggttgg   1260

taaccaagcc accatgggct ggtccctgat cctgctgttc ctggtggctg tggccaccag   1320

agtgctgagc caggtgcagc tgcagcagcc tggggctgag cttgtgaaac ctggggcctc   1380

tgtgaagatg agctgcaagg cctctggcta caccttcacc agctacaaca tgcactgggt   1440

caagcagacc cctggcagag gcctggaatg gattggagcc atctaccctg gcaatgggga   1500

cacctcctac aaccagaagt tcaagggcaa ggccaccctg acagctgaca agagcagcag   1560

cacagcctac atgcagctgt ccagcctgac ctctgaggac tctgctgtgt actactgtgc   1620
```

-continued

```
caggtccacc tactatgggg gagactggta cttcaatgtg tggggagctg gcaccacagt   1680
gacagtgtct gctgccagca ccaagggccc ctctgtgttt cctctggccc ccagcagcaa   1740
gagcacctct gggggaacag ctgccctggg ctgccttgtg aaggactact tccctgagcc   1800
tgtgactgtg tcctggaact ctggggccct gacatctggg gtgcacacct tccctgcagt   1860
gctgcagtcc agtggcctgt actccctgtc ctctgttgtg acagtgccca gctccagcct   1920
gggcacccag acctacatct gcaatgtgaa ccacaagccc agcaacacca aggtggacaa   1980
gaaggctgag cccaagagct gtgacaagac ccacacctgt cccccctgtc ctgcccctga   2040
actgctggga ggaccttctg tgttcctgtt cccacccaag cccaaggata ccctgatgat   2100
cagcagaacc cctgaagtga cctgtgtggt ggtggatgtg tcccatgagg acccagaagt   2160
gaagttcaat tggtatgtgg atggggtgga agtgcacaat gccaagacca agcccagaga   2220
ggaacagtac aacagcacct acagagtggt gtctgtgctg actgtgctgc accaggactg   2280
gctgaatggc aaagagtaca agtgcaaggt gtccaacaag gccctgccag cccccattga   2340
gaaaaccatc agcaaggcca agggccagcc tagagaaccc caggtgtaca cactgccccc   2400
tagcagggat gagctgacca agaaccaggt gtccctgaca tgccttgtga aaggcttcta   2460
cccctctgac attgctgtgg aatgggagag caatggacag cctgagaaca actacaagac   2520
caccccccct gtgctggact ctgatggctc attcttcctg tacagcaagc tgacagtgga   2580
caagtccaga tggcagcagg gcaatgtgtt cagctgctct gtgatgcatg aggccctgca   2640
caaccactac acccagaaaa gcctgtccct gtcccctggc aagtgaagat ctacttctgg   2700
ctaataaaag atcagagctc tagtgatctg tgtgttggtt ttttgtgtct gcattctagc   2760
agagccccac tgtgttcatc ttacagatgg aaatactgac attcagagga gttagttaac   2820
ttgcctaggt gattcagcta ataagtgcaa gaaagatttc aatccaaggt gatttgattc   2880
tgaagcctgt gctaatcaca ttacaccaag ctacaacttc atttataaat aataagtcag   2940
ctttcaaggg cctttcaggt gtcctgcact tctacaagct gtgccattta gtgaacacaa   3000
aatgagcctt ctgatgaagt agtcttttca ttatttcaga tattagaaca ctaaaattct   3060
tagctgccag ctgattgaag gctgggacaa aattcaaaca tgcatctaca acaatatata   3120
tctcaatgtt agtctccaaa ttctattgac ttcaactcaa gagaatataa agagctagtc   3180
tttatacact ctttaaggta tgatatcatc tggaaagtaa caaaattgat gcaaatttga   3240
atgaacttta tcatggtgta tttacacaat gtgtttcttc tccctgcaat gtatttcttt   3300
ctctaattcc ttccatttga tctttcatac acaatctggt tctgatgtat gtttttttgga   3360
tgcacttttc aactccaaaa gacagagcta gttactttct tcctggtgct ccaagcactg   3420
tatttgtatc tgtattcaag ccctttgcaa tattgtactg gatcattatt tcacctctag   3480
gatggcttcc ccaggcaact tgtgttcacc cagagactac attttgtatc ttgttgacct   3540
ttgaacttcc accagtgtct aaaaataata tgtatgcaaa attacttgct atgagaatgt   3600
ataattaaac aatataaaaa ggagaagcaa ggagagaaac acaggtgtgt atttgtgttt   3660
gtgtgcttaa aaggcagtgt ggaaaaggaa gaaatgccat ttatagtgag gagacaaagt   3720
tatattacct cttatctggc ttttaaggag attttgctga gctaaaaatc ctatattcat   3780
agaaaagcct tacctgagtt gccaatacct caattcagtc tagcaggagt caatgggaaa   3840
aacccattgg agccaagtac actgactcaa tagggacttt ccattgggtt ttgcccagta   3900
cataaggtca ataggggggtg agtcaacagg aaagtcccat tggagccaag tacattgagt   3960
caatagggac tttccaatgg gttttgccca gtacataagg tcaatgggag gtaagccaat   4020
```

```
gggtttttcc cattactgac atgtatactg agtcattagg gactttccaa tgggttttgc   4080
ccagtacata aggtcaatag ggtgaatca acaggaaagt cccattggag ccaagtacac   4140
tgagtcaata gggactttcc attgggtttt gcccagtaca aaaggtcaat agggggtgag   4200
tcaatgggtt tttcccatta ttggcacata cataaggtca ataggggtga ctagtggaga   4260
agagcatgct tgagggctga gtgcccctca gtgggcagag agcacatggc ccacagtccc   4320
tgagaagttg gggggagggg tgggcaattg aactggtgcc tagagaaggt ggggcttggg   4380
taaactggga aagtgatgtg gtgtactggc tccacctttt tccccagggt gggggagaac   4440
catatataag tgcagtagtc tctgtgaaca ttcaagcttc tgccttctcc ctcctgtgag   4500
tttggtaagt cactgactgt ctatgcctgg gaaagggtgg gcaggagatg gggcagtgca   4560
ggaaaagtgg cactatgaac cctgcagccc tagacaattg tactaacctt cttctctttc   4620
ctctcctgac aggttggtaa ccaagccacc atggacttcc aggtgcagat catcagcttt   4680
ctgctgatct ctgcctctgt gatcatgagc agaggccaga ttgtgctgag ccagagccct   4740
gccatcctgt ctgcaagccc tggggagaaa gtgaccatga cctgcagagc cagcagctct   4800
gtgtcctaca tccactggtt ccagcagaag cctggcagca gccccaagcc ttggatctat   4860
gccaccagca acctggcatc tggggtgcca gtcagattct ctggctctgg atctggcacc   4920
agctacagcc tgaccatcag cagagtggaa gctgaggatg ctgccaccta ctactgccag   4980
cagtggacca gcaatccccc cacctttgga gggggcacca agctggaaat caagagaaca   5040
gtggctgccc cctctgtgtt catcttccca ccctctgatg agcagctgaa gtctggaaca   5100
gcctctgttg tgtgcctgct gaacaacttc taccccagag aagccaaggt gcagtggaag   5160
gtggacaatg ccctgcagtc tggcaactcc caggaatctg tgacagagca ggacagcaag   5220
gactccacct actccctgag cagcaccctg accctgagca aggctgacta tgagaagcac   5280
aaagtgtatg cctgtgaagt gacccaccag ggcctgtcca gccctgtgac caagagcttc   5340
aacagagggg agagctgaag atctacttct ggctaataaa agatcagagc tctagtgatc   5400
tgtgtgttgg tttttttgtgt ctgcattcta gcagtcaata tgttcacccc aaaaaagctg   5460
tttgttaact tgtcaacctc attctaaaat gtatatagaa gcccaaaaga caataacaaa   5520
aatattcttg tagaacaaaa tgggaaagaa tgttccacta aatatcaaga tttagagcaa   5580
agcatgagat gtgtggggat agacagtgag gctgataaaa tagagtagag ctcagaaaca   5640
gacccattga tatatgtaag tgacctatga aaaaaatatg gcattttaca atgggaaaat   5700
gatggtcttt ttcttttta gaaaaacagg gaaatatatt tatatgtaaa aaataaaagg   5760
gaacccatat gtcataccat acacacaaaa aaattccagt gaattataag tctaaatgga   5820
gaaggcaaaa ctttaaatct tttagaaaat aatatagaag catgccatca agacttcagt   5880
gtagagaaaa atttcttatg actcaaagtc ctaaccacaa agaaaagatt gttaattaga   5940
ttgcatgaat attaagactt atttttaaaa ttaaaaaacc attaagaaaa gtcaggccat   6000
agaatgacag aaaatatttg caacacccca gtaaagagaa ttgtaatatg cagattataa   6060
aaagaagtct tacaaatcag taaaaaataa aactagacaa aaatttgaac agatgaaaga   6120
gaaactctaa ataatcatta cacatgagaa actcaatctc agaaatcaga gaactatcat   6180
tgcatataca ctaaattaga gaaatattaa aaggctaagt aacatctgtg gctctagctc   6240
tagtgatcag cagttcaacc tgttgatagt atgtactaag ctctcatgtt taatgtacta   6300
agctctcatg tttaatgaac taaaccctca tggctaatgt actaagctct catggctaat   6360
```

```
gtactaagct ctcatgtttc atgtactaag ctctcatgtt tgaacaataa aattaatata   6420
aatcagcaac ttaaatagcc tctaaggttt taagttttat aagaaaaaaa agaatatata   6480
aggcttttaa aggttttaag gtttcctagg ttatcctcat atgagctctt agaaaaactc   6540
atccagcatc aaatgaaact gcaatttatt catatcagga ttatcaatac catatttttg   6600
aaaaagtctt ttctgtaatg aaggagaaaa ctcacccagg cagttccata ggatggcaag   6660
atcctggtat ctgtctgcaa ttccaactct tccaacatca atacaaccta ttaatttccc   6720
ctcatcaaaa ataaggttat caagtgagaa atcaccatga gtgaccactg aatctggtga   6780
gaatggcaaa agattatgca tttctttcca gacttgttca acaggccagc catttctctc   6840
atcatcaaaa tcactggcat caaccaaacc attattcatt cttgattggg cctgagccag   6900
tctaaatact ctatcagagt taaaaggaca attacaaaca ggaatggaat gcaatcttct   6960
caggaacact gccagggcat caacaatatt ttcacctgaa tcaggatatt cttccaatac   7020
ctggaatgct gttttccctg ggatggcagt ggtgagtaac catgcatcat caggagttct   7080
gataaaatgc ttgatggttg gaagaggcat aaattcagtc agccagttta gtctgaccat   7140
ctcatctgta acatcattgg caacagaacc tttgccatgt ttcagaaaca actctggggc   7200
atctggcttc ccatacaatc tatagattgt ggcacctgat tgcccaacat tatctctagc   7260
ccatttatac ccatataaat cagcatccat gttggaattt aatcttggcc tggagcaaga   7320
ggtttctctt tgaatatggc tcatacatgt gcacctccta tagtgagttg tattatacta   7380
tgcagatata ctatgccaat gtttaattgt cag                                7413
```

<210> SEQ ID NO 10
<211> LENGTH: 3492
<212> TYPE: DNA
<213> ORGANISM: Artificial sequence
<220> FEATURE:
<223> OTHER INFORMATION: synthetic

<400> SEQUENCE: 10

```
cactatgtgg acatgaattc aattggctag caggagtcaa tgggaaaaac ccattggagc     60
caagtacact gactcaatag ggactttcca ttgggttttg cccagtacat aaggtcaata    120
gggggtgagt caacaggaaa gtcccattgg agccaagtac attgagtcaa tagggacttt    180
ccaatgggtt ttgcccagta cataaggtca atgggaggta agccaatggg tttttcccat    240
tactgacatg tatactgagt cattagggac tttccaatgg gttttgccca gtacataagg    300
tcaatagggg tgaatcaaca ggaaagtccc attggagcca agtacactga gtcaataggg    360
actttccatt gggttttgcc cagtacaaaa ggtcaatagg gggtgagtca atgggttttt    420
cccattattg gcacatacat aaggtcaata ggggtgacta gtggagaaga gcatgcttga    480
gggctgagtg cccctcagtg ggcagagagc acatggccca cagtccctga gaagttgggg    540
ggaggggtgg gcaattgaac tggtgcctag agaaggtggg gcttgggtaa actgggaaag    600
tgatgtggtg tactggctcc accttttttcc ccagggtggg ggagaaccat atataagtgc    660
agtagtctct gtgaacattc aagcttctgc cttctccctc ctgtgagttt ggtaagtcac    720
tgactgtcta tgcctgggaa agggtgggca ggagatgggg cagtgcagga aaagtggcac    780
tatgaaccct gcagccctag acaattgtac taaccttctt ctctttcctc tcctgacagg    840
ttggtaacca agccaccatg cagagagtga atatgatcat ggctgagagc cctggcctga    900
tcaccatctg cctgctgggc tacctgctgt ctgctgagtg cacagtgttt ctggaccatg    960
agaatgccaa caagatcctg aacaggccca agaggtacaa ctctggcaag ctggaagagt   1020
```

-continued

```
ttgtgcaggg caacctggaa agggaatgca tggaagagaa gtgcagcttt gaagaggcca   1080

gggaagtgtt tgagaacaca gagagaacca cagagttctg gaagcagtat gtggatgggg   1140

accagtgtga aagcaacccc tgcctgaatg gggcagctg caaggatgac atcaacagct   1200

atgagtgctg gtgccccttt ggctttgagg gcaagaactg tgaactggat gtgacctgca   1260

acatcaagaa tggcagatgt gaacagttct gcaagaactc tgctgacaac aaggttgtgt   1320

gctcctgcac agagggctac agactggctg agaaccagaa aagctgtgaa cctgctgtgc   1380

ccttcccatg tggcagagtg tctgtgtccc agaccagcaa gctgaccaga gctgagacag   1440

tgttccctga tgtggactat gtgaactcca cagaggctga aaccatcctg gacaacatca   1500

cccagagcac ccagtccttc aatgacttca ccagagttgt gggaggggag gatgccaagc   1560

ctggccagtt cccatggcaa gtggtgctga atggcaaagt ggatgccttc tgtgggggct   1620

ccattgtgaa tgagaagtgg attgtgacag ctgcccactg tgtggaaact ggagtgaaga   1680

tcacagtggt ggctggggag cacaacattg aggaaacaga gcacacagag cagaaaagaa   1740

atgtgatcag gatcatcccc caccacaact acaatgctgc catcaacaag tacaaccatg   1800

acattgccct gctggaactg gatgagcccc tggtgctgaa cagctatgtg acccccatct   1860

gcattgctga caaagagtac accaacatct ttctgaagtt tggctctggc tatgtgtctg   1920

gctggggcag ggtgttccac aagggaagga gtgctctggt gctgcagtac ctgagagtgc   1980

cactggtgga cagagccacc tgtctgagaa gcaccaagtt caccatctac aacaacatgt   2040

tctgtgctgg cttccatgag gggggcagag actcctgcca gggggattct gggggccctc   2100

atgtgacaga ggtggaaggc accagctttc tgacaggcat catcagctgg ggagaggaat   2160

gtgccatgaa gggcaaatat ggcatctaca ccaaggtgtc cagatatgtg aattggatca   2220

aagaaaagac caagctgaca tgaagatcta cttctggcta ataaaagatc agagctctag   2280

tgatctgtgt gttggttttt tgtgtctgca ttctagctct agtgatcagc agttcaacct   2340

gttgatagta tgtactaagc tctcatgttt aatgtactaa gctctcatgt ttaatgaact   2400

aaaccctcat ggctaatgta ctaagctctc atggctaatg tactaagctc tcatgtttca   2460

tgtactaagc tctcatgttt gaacaataaa attaatataa atcagcaact taaatagcct   2520

ctaaggtttt aagttttata agaaaaaaaa gaatatataa ggcttttaaa ggttttaagg   2580

tttcctaggt tatcctcata tgagctctta gaaaaactca tccagcatca aatgaaactg   2640

caatttattc atatcaggat tatcaatacc atatttttga aaaagtcttt tctgtaatga   2700

aggagaaaac tcacccaggc agttccatag gatggcaaga tcctggtatc tgtctgcaat   2760

tccaactctt ccaacatcaa tacaacctat taatttcccc tcatcaaaaa taaggttatc   2820

aagtgagaaa tcaccatgag tgaccactga atctggtgag aatggcaaaa gattatgcat   2880

ttctttccag acttgttcaa caggccagcc atttctctca tcatcaaaat cactggcatc   2940

aaccaaacca ttattcattc ttgattgggc ctgagccagt ctaaatactc tatcagagtt   3000

aaaaggacaa ttacaaacag gaatggaatg caatcttctc aggaacactg ccagggcatc   3060

aacaatattt tcacctgaat caggatattc ttccaatacc tggaatgctg ttttccctgg   3120

gatggcagtg gtgagtaacc atgcatcatc aggagttctg ataaaatgct tgatggttgg   3180

aagaggcata aattcagtca gccagtttag tctgaccatc tcatctgtaa catcattggc   3240

aacagaacct ttgccatgtt tcagaaacaa ctctggggca tctggcttcc catacaatct   3300

atagattgtg gcacctgatt gcccaacatt atctctagcc catttatacc catataaatc   3360
```

-continued

```
agcatccatg ttggaattta atcttggcct ggagcaagag gtttctcttt gaatatggct   3420

catacatgtg cacctcctat agtgagttgt attatactat gcagatatac tatgccaatg   3480

tttaattgtc ag                                                       3492
```